(12) United States Patent
Ahuja et al.

(10) Patent No.: US 6,482,411 B1
(45) Date of Patent: Nov. 19, 2002

(54) METHODS OF REDUCING BONE LOSS WITH CD40 LIGAND

(75) Inventors: Seema A. Ahuja, San Antonio, TX (US); Lynda F. Bonewald, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 71 days.

(21) Appl. No.: 09/645,926

(22) Filed: Aug. 24, 2000

Related U.S. Application Data

(60) Provisional application No. 60/151,250, filed on Aug. 27, 1999.

(51) Int. Cl.[7] .................. A61K 38/17; A61K 38/19; C07K 14/435; C07K 14/52
(52) U.S. Cl. ............... 424/185.1; 424/85.1; 424/184.1; 424/192.1; 424/178.1; 514/2; 514/8; 514/12; 514/885; 530/350; 530/351
(58) Field of Search ............................. 424/85.1, 185.1, 424/278.1; 514/2, 8; 530/350

(56) References Cited

U.S. PATENT DOCUMENTS

| | | | |
|---|---|---|---|
| 5,540,926 A | 7/1996 | Aruffo et al. | 424/153.1 |
| 5,565,321 A | 10/1996 | Spriggs et al. | 435/6 |
| 5,674,492 A | 10/1997 | Armitage et al. | 424/144.1 |
| 5,716,805 A | 2/1998 | Srinivasan et al. | 435/69.1 |
| 5,811,535 A | 9/1998 | Adamou et al. | 536/23.5 |
| 6,017,527 A | 1/2000 | Maraskovsky et al. | 424/93.71 |
| 6,087,329 A | 7/2000 | Armitage et al. | 514/8 |
| 6,106,832 A | 8/2000 | Spriggs et al. | 424/134.1 |

FOREIGN PATENT DOCUMENTS

| | | |
|---|---|---|
| EP | 0 585 943 A2 | 3/1994 |
| EP | 0 823 478 A2 | 2/1998 |
| WO | WO 93/08207 | 4/1993 |

OTHER PUBLICATIONS

Bjorck et al., "Antibodies to distinct epitopes on the CD40 molecule co–operae in stimulation and can be used for the detection of soluble CD40," *Immunlolgy*, 83:430–437, 1994.
Buske et al., "In vitro activation of low–grade non–Hodgkin's lymphoma by murine fibroblasts, IL–4, anti–CD40 antibodies and the soluble CD40 ligand," *Leulemia*, 11:1862–1867, 1997.
Ledbetter et al., "Agonistic and antagonistic properties of CD40 mAb G28–5 are dependent on binding valency," *Circulatory Shock*, 44:67–72, 1995.
Ahuja, et al., "CD40 Ligand (CD40L) in an anti–apoptotic factor for bone cells," *Journal. of Bone and Mineral Research*, 14(Supp.1):S345, Sep. 1999.

*Primary Examiner*—Phillip Gambel
(74) *Attorney, Agent, or Firm*—Williams, Morgan and Amerson

(57) ABSTRACT

Provided are methods and compositions using one or more CD40 agonists, such as CD40 ligands and/or agonistic anti-CD40 antibodies, to reduce or prevent cell death, or apoptosis, in bone cells. Methods of treating or preventing bone loss, including osteoporosis, as well as methods of reducing or eliminating the bone loss associated with steroid administration are particularly provided. Further disclosed are a variety of therapeutic kits and cocktails.

34 Claims, 2 Drawing Sheets

SEQUENCE LISTING

```
<160> NUMBER OF SEQ ID NOS:   7

<210> SEQ ID NO 1
<211> LENGTH: 879
<212> TYPE: DNA
<213> ORGANISM: Homo sapiens

<400> SEQUENCE: 1
ccatttcaac tttaacacag catgatcgaa acatacaacc aaacttctcc ccgatctgcg      60
gccactggac tgcccatcag catgaaaatt tttatgtatt tacttactgt ttttcttatc    120
acccagatga ttgggtcagc acttttttgct gtgtatcttc atagaaggtt ggacaagata   180
gaagatgaaa ggaatcttca tgaagatttt gtattcatga aaacgataca gagatgcaac   240
acaggagaaa gatccttatc cttactgaac tgtgaggaga ttaaaagcca gtttgaaggc   300
tttgtgaagg atataatgtt aaacaaagag gagacgaaga aagaaaacag ctttgaaatg   360
```

```
caaaaaggtg atcagaatcc tcaaattgcg gcacatgtca taagtgaggc cagcagtaaa    420
acaacatctg tgttacagtg ggctgaaaaa ggatactaca ccatgagcaa caacttggta    480
accctggaaa atgggaaaca gctgaccgtt aaaagacaag gactctatta tatctatgcc    540
caagtcacct tctgttccaa tcgggaagct tcgagtcaag ctccatttat agccagcctc    600
tgcctaaagt cccccggtag attcgagaga atcttactca gagctgcaaa tacccacagt    660
tccgccaaac cttgcgggca acaatccatt cacttgggag gagtatttga attgcaacca    720
ggtgcttcgg tgtttgtcaa tgtgactgat ccaagccaag tgagccatgg cactggcttc    780
acgtcctttg gcttactcaa actctgaaca gtgtcacctt gcaggctgtg gtggagctga    840
cgctgggagt cttcataata cagcacaggc ttaagccca                           879
```

<210> SEQ ID NO 2
<211> LENGTH: 261
<212> TYPE: PRT
<213> ORGANISM: Homo sapiens

<400> SEQUENCE: 2

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

<210> SEQ ID NO 3
<211> LENGTH: 33
<212> TYPE: PRT
<213> ORGANISM: Unknown
<220> FEATURE:
<223> OTHER INFORMATION: Synthetic peptide

<400> SEQUENCE: 3

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 4
<211> LENGTH: 27
<212> TYPE: PRT
<213> ORGANISM: Unknown
<220> FEATURE:
<223> OTHER INFORMATION: Synthetic peptide

<400> SEQUENCE: 4

Pro Asp Val Ala Ser Leu Arg Gln Gln Val Glu Ala Leu Gln Gly Gln
1               5                   10                  15

Val Gln His Leu Gln Ala Ala Phe Ser Gln Tyr
            20                  25

<210> SEQ ID NO 5
<211> LENGTH: 1816
<212> TYPE: DNA
<213> ORGANISM: Homo sapiens

<400> SEQUENCE: 5
cttctctgcc agaagatacc atttcaactt taacacagca tgatcgaaac atacaaccaa      60
acttctcccc gatctgcggc cactggactg cccatcagca tgaaattttt tatgtattta     120
cttactgttt ttcttatcac ccagatgatt gggtcagcac ttttttgctgt gtatcttcat    180
agaaggttgg acaagataga agatgaaagg aatcttcatg aagattttgt attcatgaaa    240
acgatacaga gatgcaacac aggagaaaga tccttatcct tactgaactg tgaggagatt    300
aaaagccagt ttgaaggctt tgtgaaggat ataatgttaa caaagagga gacgaagaaa     360
gaaacagct ttgaaatgca aaaggtgat cagaatcctc aaattgcggc acatgtcata     420
agtgaggcca gcagtaaaac aacatctgtg ttacagtggg ctgaaaaagg atactacacc    480
atgagcaaca acttggtaac cctgaaaaat gggaaacagc tgaccgttaa agacaagga    540
ctctattata tctatgccca agtcaccttc tgttccaatc gggaagcttc gagtcaagct    600
ccatttatag ccagcctctg cctaaagtcc cccggtagat tcgagagaat cttactcaga    660
gctgcaaata cccacagttc cgccaaacct tgcgggcaac aatccattca cttgggagga    720
gtatttgaat tgcaaccagg tgcttcggtg tttgtcaatg tgactgatcc aagccaagtg    780
agccatggca ctggcttcac gtcctttggc ttactcaaac tctgaacagt gtcaccttgc    840
aggctgtggt ggagctgacg ctgggagtct tcataataca gcacagcggt taagcccacc    900
ccctgttaac tgcctattta taaccctagg atcctcctta tggagaacta tttattatac    960
actccaaggc atgtagaact gtaataagtg aattacaggt cacatgaaac caaaacgggc   1020
cctgctccat aagagcttat atatctgaag cagcaacccc actgatgcag acatccagag   1080
agtcctatga aaagacaagg ccattatgca caggttgaat tctgagtaaa cagcagataa   1140

-continued

```
cttgccaagt tcagttttgt ttctttgcgt gcagtgtctt tccatggata atgcatttga   1200
tttatcagtg aagatgcaga agggaaatgg ggagcctcag ctcacattca gttatggttg   1260
actctgggtt cctatggcct tgttggaggg ggccaggctc tagaacgtct aacacagtgg   1320
agaaccgaaa cccccccccc cccccccgcc accctctcgg acagttattc attctctttc   1380
aatctctctc tctccatctc tctctttcag tctctctctc tcaacctctt tcttccaatc   1440
tctctttctc aatctctctg tttcccttg tcagtctctt ccctccccca gtctctcttc   1500
tcaatccccc tttctaacac acacacacac acacacacac acacacacac acacacacac   1560
acacacacac acacacacac agagtcaggc cgttgctagt cagttctctt ctttccaccc   1620
tgtccctatc tctaccacta tagatgaggg tgaggagtag ggagtgcagc cctgagcctg   1680
cccactcctc attacgaaat gactgtattt aaaggaaatc tattgtatct acctgcagtc   1740
tccattgttt ccagagtgaa cttgtaatta tcttgttatt tatttttga ataataaaga   1800 cctcttaaca ttaaaa                                                  1816
```

<210> SEQ ID NO 6
<211> LENGTH: 2339
<212> TYPE: DNA
<213> ORGANISM: Homo sapiens

<400> SEQUENCE: 6

```
acgaaggcca cgcgcccggc gcccctgagc cggccgagcg gcgacggacc gcgagatgag    60
gaaaatgagg cccaaagaag tgatgccact tggttaaggt cccagagcag gtcagaatca   120
gacctaggat cagaaacctg gctcctggct cctgctccct actcttctaa ggatcgctgt   180
cctgacagaa gagaactcct ctttcctaaa atggagtcga gtaaaaagat ggactctcct   240
ggcgcgctgc agactaaccc gccgctaaag ctgcacactg accgcagtgc tgggacgcca   300 gttttttgtcc ctgaacaagg aggttacaag gaaaagtttg tgaagaccgt ggaggacaag   360
tacaagtgtg agaagtgcca cctggtgctg tgcagcccga agcagaccga gtgtgggcac   420
cgcttctgcg agagctgcat gcgggccctg ctgagctctt caagtccaaa atgtacagcg   480
tgtcaagaga gcatcgttaa agataaggtg tttaaggata attgctgcaa gagagaaatt   540
ctggctcttc agatctattg tcggaatgaa agcagaggtt gtgcagagca gttaatgctg   600
ggacatctgg tgcatttaaa aaatgattgc cattttgaag aacttccatg tgtgcgtcct   660
gactgcaaaa aaaaggtctt gaggaaagac ctgcagagacc acgtggagaa ggcgtgtaaa   720
taccgggaag ccacatgcag ccactgcaag agtcaggttc cgatgatcgc gctgcagaaa   780
cacgaagaca ccgactgtcc ctgcgtggtg gtgtcctgcc ctcacaagtg cagcgtccag   840
actctcctga ggagcgagtt gagtgcacac ttgtcagagt gtgtcaatgc ccccagcacc   900 tgtagttttta agcgctatgg ctgcgttttt caggggacaa accagcagat caaggcccac   960
gaggccagct ccgccgtgca gcacgtcaac ctgctgaagg agtggagcaa ctcgctcgaa  1020
aagaaggttt ccttgttgca gaatgaaagt gtagaaaaaa acaagagcat acaaagtttg  1080
cacaatcaga tatgtagctt tgaaattgaa attgagagac aaaaggaaat gcttcgaaat  1140
aatgaatcca aaatccttca tttacagcga gtgatagaca gccaagcaga gaaactgaag  1200
gagcttgaca aggagatccg gcccttccgg cagaactggg aggaagcaga cagcatgaag  1260
agcagcgtgg agtccctcca gaaccgcgtg accgagctgg agagcgtgga caagagcgcg  1320
gggcaagtgg ctcggaacac aggcctgctg gagtcccagc tgagccggca tgaccagatg  1380
ctgagtgtgc acgacatccg cctagccgac atggacctgg gcttccaggt cctggagacc  1440
```

-continued

```
gccagctaca atggagtgct catctggaag attcgcgact acaagcggcg gaagcaggag   1500
gccgtcatgg ggaagaccct gtcccttac agccagcctt tctacactgg ttactttggc   1560
tataagatgt gtgccagggt ctacctgaac ggggacggga tggggaaggg gacgcacttg   1620
tcgctgtttt ttgtcatcat gcgtggagaa tatgatgccc tgcttccttg gccgtttaag   1680
cagaaagtga cactcatgct gatggatcag gggtcctctc gacgtcattt gggagatgca   1740
ttcaagcccg accccaacag cagcagcttc aagaagccca ctggagagat gaatatcgcc   1800
tctggctgcc cagtctttgt ggcccaaact gttctagaaa atgggacata tattaaagat   1860
gatacaattt ttattaaagt catagtggat acttcggatc tgcccgatcc ctgataagta   1920
gctggggagg tggatttagc agaaggcaac tcctctgggg gatttgaacc ggtctgtctt   1980
cactgaggtc ctcgcgctca gaaaaggacc ttgtgagacg gaggaagcgg cagaaggcgg   2040
acgcgtgccg gcgggaggag ccacgcgaga gcacacctga cacgttttat aatagactag   2100
ccacacttca ctctgaagaa ttatttatcc ttcaacaaga taaatattgc tgtcagagaa   2160
ggttttcatt ttcattttta aagatctagt taattaaggt ggaaaacata tatgctaaac   2220
aaaagaaaca tgattttct tccttaaact tgaacaccaa aaaacacac acacacacac   2280 acgtggggat agctggacat gtcagcatgt taagtaaaag gagaatttat gaaatagta   2339
```

<210> SEQ ID NO 7  
<211> LENGTH: 567  
<212> TYPE: PRT  
<213> ORGANISM: Homo sapiens

<400> SEQUENCE: 7

```
Met Glu Ser Ser Lys Lys Met Asp Ser Pro Gly Ala Leu Gln Thr Asn
 1               5                  10                  15

Pro Pro Leu Lys Leu His Thr Asp Arg Ser Ala Gly Thr Pro Val Phe
            20                  25                  30

Val Pro Glu Gln Gly Gly Tyr Lys Glu Lys Phe Val Lys Thr Val Glu
        35                  40                  45

Asp Lys Tyr Lys Cys Glu Lys Cys His Leu Val Leu Cys Ser Pro Lys
    50                  55                  60

Gln Thr Glu Cys Gly His Arg Phe Cys Glu Ser Cys Met Ala Ala Leu
65                  70                  75                  80

Leu Ser Ser Ser Pro Lys Cys Thr Ala Cys Gln Glu Ser Ile Val
                85                  90                  95

Lys Asp Lys Val Phe Lys Asp Asn Cys Cys Lys Arg Glu Ile Leu Ala
            100                 105                 110

Leu Gln Ile Tyr Cys Arg Asn Glu Ser Arg Gly Cys Ala Glu Gln Leu
        115                 120                 125

Met Leu Gly His Leu Val His Leu Lys Asn Asp Cys His Phe Glu Glu
    130                 135                 140

Leu Pro Cys Val Arg Pro Asp Cys Lys Glu Lys Val Leu Arg Lys Asp
145                 150                 155                 160

Leu Arg Asp His Val Glu Lys Ala Cys Lys Tyr Arg Glu Ala Thr Cys
                165                 170                 175

Ser His Cys Lys Ser Gln Val Pro Met Ile Ala Leu Gln Lys His Glu
            180                 185                 190

Asp Thr Asp Cys Pro Cys Val Val Ser Cys Pro His Lys Cys Ser
        195                 200                 205

Val Gln Thr Leu Leu Arg Ser Glu Leu Ser Ala His Leu Ser Glu Cys
```

-continued

```
                210                215                220
Val Asn Ala Pro Ser Thr Cys Ser Phe Lys Arg Tyr Gly Cys Val Phe
225                 230                235                240

Gln Gly Thr Asn Gln Gln Ile Lys Ala His Glu Ala Ser Ser Ala Val
                245                250                255

Gln His Val Asn Leu Leu Lys Glu Trp Ser Asn Ser Leu Glu Lys Lys
                260                265                270

Val Ser Leu Leu Gln Asn Glu Ser Val Glu Lys Asn Lys Ser Ile Gln
                275                280                285

Ser Leu His Asn Gln Ile Cys Ser Phe Glu Ile Glu Ile Glu Arg Gln
290                 295                300

Lys Glu Met Leu Arg Asn Asn Glu Ser Lys Ile Leu His Leu Gln Arg
305                 310                315                320

Val Ile Asp Ser Gln Ala Glu Lys Leu Lys Glu Leu Asp Lys Glu Ile
                325                330                335

Arg Pro Phe Arg Gln Asn Trp Glu Glu Ala Asp Ser Met Lys Ser Ser
                340                345                350

Val Glu Ser Leu Gln Asn Arg Val Thr Glu Leu Glu Ser Val Asp Lys
                355                360                365

Ser Ala Gly Gln Val Ala Arg Asn Thr Gly Leu Leu Glu Ser Gln Leu
370                 375                380

Ser Arg His Asp Gln Met Leu Ser Val His Asp Ile Arg Leu Ala Asp
385                 390                395                400

Met Asp Leu Gly Phe Gln Val Leu Glu Thr Ala Ser Tyr Asn Gly Val
                405                410                415

Leu Ile Trp Lys Ile Arg Asp Tyr Lys Arg Arg Lys Gln Glu Ala Val
                420                425                430

Met Gly Lys Thr Leu Ser Leu Tyr Ser Gln Pro Phe Tyr Thr Gly Tyr
                435                440                445

Phe Gly Tyr Lys Met Cys Ala Arg Val Tyr Leu Asn Gly Asp Gly Met
450                 455                460

Gly Lys Gly Thr His Leu Ser Leu Phe Phe Val Ile Met Arg Gly Glu
465                 470                475                480

Tyr Asp Ala Leu Leu Pro Trp Pro Phe Lys Gln Lys Val Thr Leu Met
                485                490                495

Leu Met Asp Gln Gly Ser Ser Arg Arg His Leu Gly Asp Ala Phe Lys
                500                505                510

Pro Asp Pro Asn Ser Ser Ser Phe Lys Lys Pro Thr Gly Glu Met Asn
                515                520                525

Ile Ala Ser Gly Cys Pro Val Phe Val Ala Gln Thr Val Leu Glu Asn
                530                535                540

Gly Thr Tyr Ile Lys Asp Asp Thr Ile Phe Ile Lys Val Ile Val Asp
545                 550                555                560

Thr Ser Asp Leu Pro Asp Pro
                565
```

METHODS OF REDUCING BONE LOSS WITH CD40 LIGAND

The present application claims priority to U.S. provisional application Ser. No. 60/151,250, filed Aug. 27, 1999, the entire text, figures and sequences of which application is incorporated herein by reference without disclaimer.

BACKGROUND OF THE INVENTION

1. Field of the Invention

The present invention relates generally to the fields of cell biology and bone metabolism. More particularly, it concerns the use of compositions containing one or more CD40 agonists, such as CD40 ligands and/or agonistic anti-CD40 antibodies, to reduce or prevent cell death or apoptosis, in bone cells, such as osteocytes and osteoblasts. Methods of treating or preventing bone loss, including osteoporosis, and methods of reducing or eliminating the bone loss associated with steroid administration are also included. Further provided are a variety of therapeutic kits and cocktails.

2. Description of Related Art

In the body, bone is remodeled continuously through the process of resorption by osteoclasts, followed by bone formation by osteoblasts. Normally, the activity of these two types of cells is balanced through the action of hormones and other signaling mechanisms. During the resorption phase, sites for remodeling are targeted by osteoclasts that form pits in bone, releasing organic matrix and minerals into the circulation. Resorption at a single site can last as long as about three weeks. As resorption progresses, osteoblasts begin filling in the resorbed region with new mineralized bone.

Peak bone mass is reached at about age 30. After pe tne mass is reached, there is a gradual age-related loss of bone mass in both males and females due to a slight imbalance in resorption and formation. However, as estrogen production declines in women around the time of menopause, bone resorption increases dramatically, which can lead to rapid bone loss. Premenopausal women have been shown to turnover bone at a rate of about one-third to one-half gram of bone per day, while the turnover is double to triple that in early postmenopausal women. Although bone loss can be especially elevated in the five to seven years immediately following menopause, this process continues throughout life. The rate of bone loss can vary dramatically from woman to woman.

Several studies have documented this dramatic increase in bone turnover levels at menopause (Ebeling et al., 1996; Garnero et al., 1996; Prestwood et al., 1994). The results showed that the increase in both the mean and the range of bone resorption values stayed high for more than 20 years beyond menopause, a pattern consistent with bone mass changes over a woman's lifetime. These studies demonstrated an inverse correlation between bone turnover and bone mass, with high turnover associated with low bone mass.

Postmenopausal bone loss may be due to increased production of cytokines such as TNFα and interleukin 1 and/or increased osteocyte apoptosis. Estrogen has been shown to be a viability factor for osteocytes in both humans and rats (Tomkinson et al., 1997, 1998). Human bone removed from female patients being treated with gonadotropin releasing hormone showed a higher increase in the proportion of dead osteocytes compared to controls. The same was shown to be true for ovariectamized rates compared to controls (Rickard et al., 1992). Estrogen has been reported to modulate TNFα production by human osteoblast and peripheral monocytes from women who have undergone ovariectomy and produce increased levels of TNFα (Pacifici et al., 1991). Delivering both IL-1 receptor antagonist and the soluble TNF receptor completely blocked bone loss due to ovariectomy in mice (Kimble et al., 1995). Therefore, a lack of estrogen can lead to increased production of cytokines responsible for bone loss (Lorenzo, 1996).

In addition to bone loss due to aging and estrogen deficiency, patients of all ages, both sexes, and all races are susceptible to steroid-induced bone loss. Administration of glucocorticoids and steroids is the third most common cause of osteoporosis. Steroid-induced bone loss usually affects the cortical and cancellous bone of the axial skeleton. Between 30% and 50% of individuals taking steroids for more than 6 months will develop osteoporosis. The rate of bone loss is very rapid in the initial year of therapy, with as much as 20% of the bone lost in the first year. Doses exceeding 7.5 mg/day of prednisone can cause significant loss of trabecular bone in most people.

Studies in mice administered glucocorticoids suggests that steroid-induced bone loss is due to decreased bone formation which results from higher numbers of apoptotic/dead osteoclasts and osteoblasts. Lesser numbers of these cells could account for changes seen with glucocorticoid-induced bone disease. A decrease in osteoblast and osteocyte cell number due to death/apoptosis has also been demonstrated in patients who have glucocorticoid-induced osteoporosis (Weinstein et al., 1998).

Despite the current understanding and the considerable amount of research in this area, bone loss and osteoporosis remain significant medical and economic problems. Therefore, methods of reducing or preventing bone loss, for example by reducing or preventing apoptosis of osteocytes and osteoblasts, would represent a significant advance in the art.

SUMMARY OF THE INVENTION

The present invention overcomes one or more of these and other shortcomings in the art by providing a range of new treatments by which to reduce bone cell death and bone loss. The invention is broadly based upon the surprising finding that CD40 is expressed on bone cells and that CD40 agonists dramatically reduce bone cell death. The invention thus provides methods, compositions and uses of one or more CD40 agonists, such as CD40 ligands and/or agonistic anti-CD40 antibodies, to reduce or prevent bone cell death or apoptosis, thereby providing new treatments for bone loss associated with a variety of diseases and clinical conditions.

The invention therefore provides methods, compositions and uses in reducing or preventing bone cell death and/or apoptosis, comprising contacting a bone cell, a population of bone cells or a cell population comprising bone cells, with a biologically effective amount of at least a first composition comprising at least a first CD40 agonist, such as a CD40 ligand and/or agonistic anti-CD40 antibody.

The bone cells to be treated by the invention include, but are not limited to, osteoblasts and osteocytes. The CD40 ligands and/or agonists may induce the apoptosis of osteoclasts, inhibit the apoptosis of osteoclasts, or exert no detectable effects on osteoclasts, so long as the overall effect of the CD40 ligand and/or agonist inhibits the apoptosis of osteocytes and/or osteoblasts to a greater extent than osteoclasts, or otherwise produces a net beneficial effect on bone mass, bone density, bone cell number or other parameter indicative of health bone tissue.

All CD40 agonists are suitable for use in the invention, so long as they bind to and activate one or more CD40 receptors on a bone cell. A CD40 agonist that "binds to and activates" a CD40 receptor a bone cell is a biological or chemical component or agent that stimulates cell signaling via CD40 in such cells. "Cell signaling" via a CD40 receptor is indicated by the capacity to "transduce" a signal, i.e., transmit a biological effect, to the intracellular environment by binding of an agent to an extracellular portion of the receptor. Most preferably, CD40 agonists bind to and activate a CD40 receptor on a bone cell, thereby creating a cell signal that reduces cell death and/or apoptosis in the cell.

Agents that "stimulate" cell signaling via CD40 receptors may do so directly or indirectly. Although agents that act directly are generally preferred, agents that indirectly stimulate or activate CD40 receptors may be used, including accessory signaling molecules, co-stimulators and the like, and agents that remove, inactivate or downregulate inhibitors of the CD40 signaling process. Included within this group of CD40 agonists are agents that stimulate or "upregulate" the expression of the CD40 receptor on bone cells. Such components will therefore increase the amount of the receptor expressed at the cell surface and available for binding to the natural biological ligand counterpart or exogenously added CD40 ligands.

CD40 agonists that directly stimulate or activate CD40 receptors include the biological ligand counterparts to the receptor. Therefore, in preferred embodiments, the at least a first composition comprises at least a first CD40 ligand. As used herein, the term "CD40 ligand" will be understood to include any peptide, polypeptide or protein, or a nucleic acid encoding a peptide, polypeptide or protein, that can bind to and activate one or more CD40 receptors on a bone cell. Thus, CD40 ligands for use in the present invention include, but are not limited to, gp39 peptides, polypeptides, proteins or nucleic acids.

Although human CD40 ligands will be preferred for use in human therapy, CD40 ligands from any species may be used in the invention. For use in other animal species, such as in veterinary embodiments, a species of CD40 ligand matched to the animal being treated will be preferred. Therefore, among the gp39 peptides, polypeptides, proteins or nucleic acids contemplated for use in the present invention are the human, murine, canine, bovine, feline and rat gp39 sequences, as well as other CD40 binding proteins, known in the art and disclosed herein. Exemplary CD40 ligands are those of SEQ ID NO:2, as encoded by SEQ ID NO:1 and the related nucleic acid sequence of SEQ ID NO:5; and those of SEQ ID NO:7, as encoded by SEQ ID NO:6. In preferred aspects of the invention, the at least a first CD40 ligand is at least a first human gp39 peptide, protein or nucleic acid.

A CD40 ligand "protein, polypeptide or peptide", as used herein, refers to a proteinaceous CD40 ligand component that has sufficient biological activity to be biologically effective. Accordingly, "CD40 ligands" include full-length CD40 ligand proteins and polypeptides and also CD40 ligands that have been subject to non-native processing or biological modification. Such modifications include truncations, extensions, active domains or fragments, fusion proteins, mutants with substantial or sufficient biological activity, peptidomimetics and the like.

Any form of CD40 ligand may be used in the invention, including those isolated and purified from natural sources. CD40 ligands prepared by recombinant expression will often be preferred, i.e., those obtained by expressing a CD40 ligand nucleic acid in a recombinant host cell and collecting the expressed CD40 ligand protein. CD40 ligands prepared by automated peptide synthesis are also included.

In certain embodiments, the CD40 ligand is a soluble gp39 peptide, polypeptide or protein, or at least a first nucleic acid encoding a soluble gp39 peptide, polypeptide or protein.

In preferred embodiments, the at least a first CD40 ligand is at least a first soluble gp39 protein that comprises all, substantially all or most of the extracellular domain. In particular aspects, the extracellular domain of the gp39 protein comprises the human sequence from between about amino acid 47–50 to about amino acid 261 of SEQ ID NO:2 or the corresponding bovine sequence. Sequences of from between about amino acid 47–50 to about amino acid 260 of the corresponding murine, canine, feline or rat sequences may be used, as disclosed in U.S. provisional application Serial No. 60/151,250, filed Aug. 27, 1999, incorporated herein by reference. As used herein, the term "between about amino acid 47–50 to about amino acid 260 or 261" will be understood to include sequences between amino acid 45, 46, 48, 49, 51 and 52 or so to about amino acid 257, 258, 259, 260 and 261 or so.

"CD40 ligand nucleic acids" are DNA or RNA coding regions that encode, and under conditions appropriate for expression, encode and express any one or more of the biologically active CD40 ligand protein- and polypeptide-based components described above, including full-length proteins and polypeptides, and active variants, fragments and fusions thereof. Recombinant vectors, viral vectors and recombinant viruses are preferred for use in various embodiments, as described in detail herein.

Therefore, in certain aspects of the invention, the at least a first soluble gp39 protein is encoded by the sequence from between about nucleotide 160–169 to about nucleotide 804 of SEQ ID NO:1. Sequences of from between about nucleotide 151–160 to about nucleotide 792 of the corresponding murine sequence; between about nucleotide 153–162 to about nucleotide 797 of the corresponding bovine sequence; between about nucleotide 143–152 to about nucleotide 784 of the corresponding canine sequence; between about nucleotide 143–152 to about nucleotide 784 of the corresponding feline sequence; or between about nucleotide 139–148 to about nucleotide 780 of the corresponding rat sequence; may be used, as disclosed in U.S. provisional application Serial No. 60/151,250, filed Aug. 27, 1999, incorporated herein by reference.

In other aspects of the present invention, the methods, compositions and uses provide the CD40 ligand to the target bone cells via cell-based delivery. As such, the methods, compositions and uses of the invention include recombinant host cells expressing at least a first CD40 ligand or agonist on the surface of the cell.

Particularly preferred embodiments of the invention are those wherein the at least a first CD40 ligand is a gp39 peptide or protein oligomer, including naturally forming gp39 peptide, polypeptide or protein oligomers, as well as gp39 peptides, polypeptides, proteins (and encoding nucleic acids) that comprise an oligomerization sequence. While oligomers such as dimers, trimers and tetramers are preferred in certain aspects of he invention, in other aspects of the invention larger oligomeric structures are contemplated for use, so long as the oligomeric structure retains the ability to bind to and activate one or more CD40 receptor(s) on a bone cell. Exemplary oligomerization sequences include, but are not limited to, leucine zipper or lung surfactant protein D sequences. In preferred aspects of the invention, the oligomerization sequence has the amino acid sequence of SEQ ID NO:3 or SEQ ID NO:4, with SEQ ID NO:3 being particularly preferred.

In further aspects of the invention, the at least a first CD40 ligand is at least a first gp39 peptide, protein or nucleic acid that comprises a distinct antigenic sequence, exemplified by, but not limited to, antigenic sequences for detection, such as FLAG sequences. Fusion proteins comprising CD40 ligand sequences may also be used.

Other preferred embodiments are those wherein the CD40 agonist is a component other than one based upon the natural, biological ligand. As used herein, the term "CD40 agonist" thus includes proteins, polypeptides, peptides, antibodies, small molecules and other agents that bind to and activate a CD40 receptor on a bone cell. Thus, CD40 "agonists" are operationally similar to CD40 "ligands", although the agonists are not limited to derivatives of CD40 ligands, but rather include all operative species irrespective of the underlying molecular structure. Suitable CD40 agonists are known in the art and can now readily be identified in light of the functional assays provided in the present disclosure.

In certain preferred aspects, the "CD40 agonist" is at least a first agonistic anti-CD40 antibody, or antigen-binding fragment thereof, including, but not limited to, at least a first scFv, Fv, Fab', Fab or F(ab')$_2$ antigen-binding region of an anti-CD40 antibody. In certain aspects of the invention, the at least a first CD40 agonist is at least a first human, humanized or part-human chimeric anti-CD40 antibody or antigen-binding fragment thereof. In other aspects, the at least a first CD40 agonist is at least a first anti-CD40 monoclonal antibody, including, but not limited to, the G28-5, mAb89, EA-5 or S2C6 monoclonal antibody, or an antigen-binding fragment thereof.

In light of the present discoveries, one or more CD40 agonists may now be used in all in vitro and in vivo methods of reducing or preventing bone cell death and/or apoptosis. All that is required is to contact a composition comprising bone cells with a biologically effective amount of at least a first composition comprising at least a first CD40 agonist.

Such methods and uses include the addition of the CD40 agonist composition to bone cells in vitro. Accordingly, the invention provides methods and uses in culturing bone cells invitro and in generating artificial bone tissue ex vivo. The methods and uses generally comprise providing a biologically effective amount of at least a first composition comprising at least a first CD40 agonist to an in vitro or ex vivo biological sample that contains a population of bone cells.

Preferred methods, uses and medicaments of the invention are those in which the CD40 agonist compositions are provided to bone cells in vivo, simply by administering the composition to an animal or patient. The invention thus provides methods and uses of reducing or preventing bone cell death and/or apoptosis, reducing or preventing bone loss or mass and, generally, treating animals and patients with various forms of diseases and conditions associated with adverse effects on bone.

These methods and uses of the invention comprise providing to an animal or patient at least a first composition that comprises at least a first CD40 agonist in an amount effective to reduce or prevent bone cell death and/or apoptosis or reduce or prevent bone loss in the animal or patient. This is the meaning of the terms "biologically and therapeutically effective amounts", as used herein, i.e., amounts effective to reduce or prevent bone cell death and/or apoptosis or to reduce or prevent bone loss or mass when administered to an animal or patient.

The in vivo treatment methods of the invention generally require the administration of pharmaceutically or pharmacologically acceptable formulations of CD40 agonist proteins, nucleic acids, vectors or antibodies. Systemic administration, including intravenous administration, is suitable for use in the invention. More localized delivery to the bone is also contemplated.

Whether CD40 ligands, agonists or antibodies, or combinations thereof, are employed in the methods and uses of the invention, the CD40 agonists may be used alone or in combination. Accordingly, the invention encompasses the use of one, two, three, four, five, six or more CD40 agonists, including a plurality of CD40 agonists. Different CD40 ligands, agonists and/or antibodies may be formulated in combination or separately and used simultaneously or sequentially. One time and repeated uses are contemplated.

The one or more CD40 agonists may also be used in combination with other therapeutic agents. Such combination therapy aspects of the invention generally include the formulation, fabrication and/or use of "biologically or therapeutically combined effective amounts" of CD40 agonists and one or more other therapeutic agents. One, two, three, four, five, six or more other therapeutic agents may be used, including a plurality thereof. Depending on the therapeutic objective, the CD40 agonists and other therapeutic agent(s) may be formulated in combination or separately and administered simultaneously or separately, including in any order of administration.

Exemplary combined therapeutic embodiments include CD40 agonists combined for use with a biologically effective amount of at least a first cytokine, such as IL-4 and/or IL-6. In further embodiments, the CD40 agonists are combined with a biologically effective amount of at least a second, distinct agent used to treat or prevent bone cell death, including second, distinct anti-apoptosis agents. One, two, three, four, five, six or more of such agents may be used, including a plurality thereof.

Second, distinct anti-bone loss agents include anti-apoptosis agents, exemplified by, but not limited to, one or more of transforming growth factor beta (TGF-β), IL-6, estrogen, a bisphosphonate and an agent listed in Table 4. Other second, distinct anti-bone loss agents are anti-osteoporosis agents, exemplified by, but not limited to, selective estrogen receptor modulators, such as tamoxifen or raloxifene, alendronate, calcitonin, calcium, fluoride and/or vitamin D.

A wide range of diseases, disorders and conditions associated with bone loss or damage may be treated by the compositions, kits, formulations, methods, uses and medicaments of the present invention. These include both the treatment and prevention of bone loss in animals and patients, wherein the CD40 agonist compositions administered are given in therapeutically and prophylactically effective amounts, respectively.

In certain aspects of the invention, the bone loss is associated with and/or caused by a disease, including, but not limited to, osteoporosis, osteonecrosis or inflammatory arthritis. In other aspects of the invention, the bone loss is caused by aging, estrogen loss or is associated with surgical intervention. The ability to treat or prevent osteoporosis in animals and patients is a particularly important aspect of the invention, whether using CD40 agonists alone or combination therapy.

As the present invention is generally based upon the surprising finding of CD40 expression on bone cells, the use of CD40 agonists can now be intelligently applied to new group of animals and patients. Accordingly, the invention includes the selection, pre-selection or identification of certain animal or patient groups, such as selecting an animal or patient having or at risk for developing bone cell death or apoptosis, or a disease or condition associated with bone loss. Although confined to only one area of treatment, the identification of an animal or patient not suffering from cancer forms one aspect of the invention. Certain of the selection criteria therefore include the identification of an animal or patient not previously provided with a CD40 agonist for another purpose.

In further aspects of the invention, the bone loss is associated with and/or caused by steroid therapy, i.e., the administration of at least a first steroid to an animal or patient. Animals and patients may again be selected, pre-selected or identified on the basis of having or at being in need of steroid therapy or steroid therapy associated with bone loss. Steroid therapy may be administered to treat a condition or disease in the animal or patient, exemplified by, but not limited to, post-menopausal estrogen loss, estrogen loss due to ovariectomy or total hysterectomy, lupus nephritis, Takayasuds arteritis, Wegeners granulomatosis, anti-glomerular basement membrane nephritis, myositis, scleroderma, idiopathic autoimmune thrombocytopenia, asthma, a chronic obstructive lung disease, nephrotic/nephritic syndrome or even cancer. Steroid therapy may also be used in conjunction with an organ or tissue transplant, such as a bone marrow transplant or a multiple organ transplant. In certain aspects of the invention, the at least a first steroid is administered at a high dose and/or over a long period of time.

The invention thus also provides compositions, kits, formulations, methods, uses and medicaments for application in improved steroid therapy and reduced osteodetrimental steroid therapy. The animal or patient undergoing or in need of steroid therapy is provided with a therapeutically or prophylactically effective amount of at least a first composition comprising at least a first CD40 agonist effective to counteract the side-effects of the steroid, such as reducing the osteodetrimental effects of the steroid. This provides steroid therapy with reduced bone loss, wherein the compositions of the invention are administered in amounts effective to reduce the bone loss associated with the steroid or steroid therapy. The CD40 agonists may be administered before, during or after steroid therapy. When given together with steroids, administration may be sequential or substantially simultaneous.

The present invention is applicable to all animals, particularly humans and valuable or valued animals, such as race horses, pedigree animals, domestic pets, and animals used to produce food for human consumption. In addition to human treatment, exemplary embodiments of the invention therefore include the treatment of horses, dogs, cats and the like; the treatment of cows, pigs, boar, sheep, goat, buffalo, bison, llama, deer, elk, and other large animals, as well as their young, including calves and lambs. The treatment of smaller animals, such as rabbits and hares, is also included. The invention encompasses the treatment of birds, particularly those used to produce food for human consumption, such as chicken, turkey, duck, goose, ostrich, emus, dove, quail, and the like. Bone loss in chickens is a notable economic concern.

Still further embodiments of the invention concern therapeutic kits. The kits comprise, in at least a first suitable container, one or more CD40 agonists in conjunction with written instructions for use in reducing or preventing bone cell death and/or apoptosis or treating bone loss. Pharmaceutical compositions of CD40 agonists are preferred.

Combination therapy kits are also provided, which comprise a combined biologically effective amount of at least a first composition, preferably a pharmaceutically acceptable composition, comprising at least a first CD40 agonist and at least a second, distinct therapeutic agent, such as an anti-bone loss agent or a steroid. In preferred embodiments, the at least a second, distinct anti-bone loss agent is an anti-apoptosis or anti-osteoporosis agent.

In certain aspects, the at least a first CD40 agonist composition and the at least a second, distinct therapeutic agent are comprised within a single composition, preferably a pharmaceutical composition. Exemplary combinations are thus therapeutic cocktails comprising CD40 agonists and/or steroids or distinct anti-bone loss agents. In other embodiments, the CD40 agonist and distinct therapeutic agent compositions are comprised within distinct compositions, preferably pharmaceutical compositions. The kits may also comprise at least a third, fourth, fifth, sixth or a plurality of distinct therapeutic agents, such as steroids or anti-bone loss agents. Combinations of CD40 agonists, distinct anti-apoptosis agents and distinct anti-osteoporosis agents are particularly preferred.

Yet further provided by the present invention is a kit comprising, in at least a first suitable container, a biologically effective amount at least a first steroid and at least a first composition comprising at least a first CD40 agonist. The CD40 agonist is preferably provided in an amount effective to reduce or prevent bone loss associated with administration of the steroid to an animal or patient. Such kits may also comprise at least a second, distinct therapeutic agent, such as another steroid or anti-bone loss agent.

Finally, the invention provides for the use of the CD40 agonist compositions in accordance herewith in the preparation of a variety of medicaments for treating one or more conditions associated with bone loss. Such medicaments include the range of CD40 agonist compositions and combinations described above for the treatment of any such disease, disorder or condition.

BRIEF DESCRIPTION OF THE DRAWINGS

The following drawings form part of the present specification and are included to flurther demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
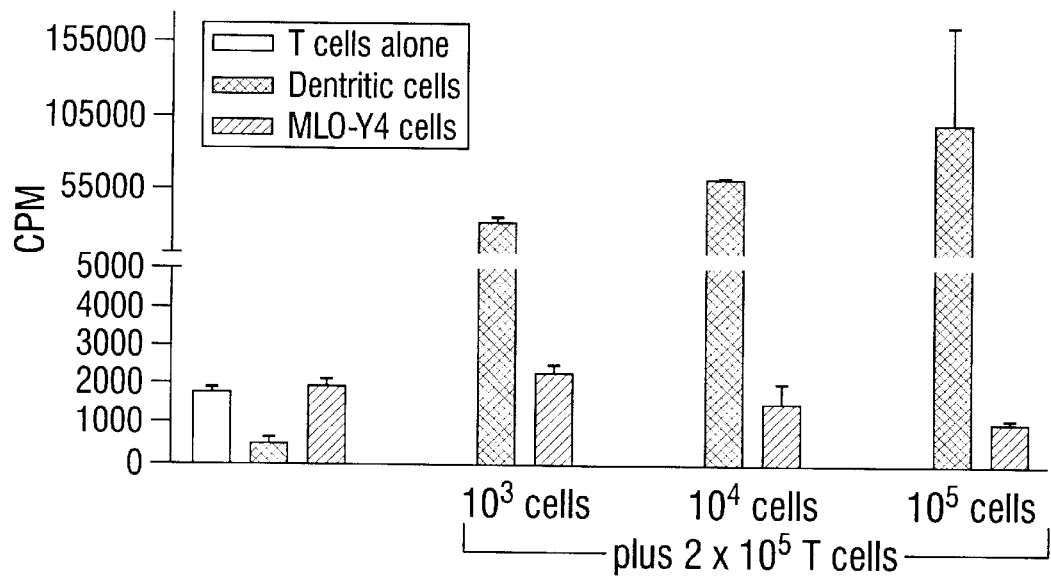
FIG. 1A and FIG. 1B. MLO-Y4 cells do not share antigen-presenting function with dendritic cells (DC). Increasing numbers of antigen presenting cells (dendritic cells or MLO-Y4 cells) were cultured with T cells, and thymidine incorporation assessed at the end of a 72 h culture as described herein. Unstimulated (FIG. 1A) and stimulated (FIG. 1B) MLO-Y4 cells, either alone, or in the presence of TNF or LPS, were unable to induce T lymphocytes to proliferate as measured by increased thymidine incorporation.

Physiological cell death that occurs during normal homeostasis, fails to initiate an inflammatory response, and has unique morphological features is termed apoptosis (Thompson, 1999). Apoptosis is a form of cellular suicide in which the dying cell initiates its own death by activation of endogenous proteases (Raff, 1998). This leads to disruption of structural integrity of the cell cytoskeleton, loss of mitochondrial fimction and the cytoplasm begins to round and shrink. The membrane of the cell begins to bleb, and there is loss of asymmetry of plasma membrane and exposure of phospholipid (phosphatidylserine) to the outside of the membrane. The nucleus becomes shnnken and pyknotic as a result of DNA degradation.

The phenomenon of apoptosis is a common way to regulate the immune system that involves differentiation, proliferation, selection and survival of the unique immune cells which help in recognition of foreign invading pathogens (Cosman, 1994; Cosulich and Clarke, 1996; Laytragoon-Lewin, 1998; Raff, 1998; Schattner and Friedman, 1996; Scott et al., 1996; Wallach, 1996; Ware et al., 1996; Wekerle et al., 1998; Wiley and Harnsen, 1999). Apoptotic cell death can be triggered once the cell has performed its physiological function, outlived its usefulness during development or become senescent. Examples in vivo include T cells that fail to undergo positive or negative selection in the thymus, B cells with low affinity for antigen deleted in the germinal centre during interaction with follicular dendritic cells, and senescent neutrophils and eosinophils.

Most white blood cells in circulation can be divided into the innate arm (neutrophils and macrophages and dendritic cells) and the adaptive arm (T and B lymphocytes). The cells of the innate arm can eliminate and process invading foreign microorganisms into small antigen peptides, and present the antigens of the foreign protein to the adaptive arm. Thus, these cells are often referred to as antigen presenting cells. The adaptive arm has acquired a memory against foreign antigens during development or during previous exposure to the foreign microorganism. The vast majority of peripheral B and T cells in circulation are in a quiescent or resting stage. They continue to receive survival signals from their stromal environment and through the receptor that recognizes the antigen. If they fail to migrate to an appropriate environment or do not have an antigen receptor binding an antigen, they undergo apoptosis (Laytragoon-Lewin, 1998; Schattmer and Friedman, 1996; Kehry, 1996; Tsubata, 1997; Mayumi, 1995, 1996; Osorio and Aguilar-Santelises, 1998).

Once the antigen receptor on the B cell is activated by binding/recognition of the antigen presented by the antigen-presenting cell, it undergoes cell division and growth. This results in large number of the same kind of cells (clonal expansion) that can recognize the same antigen. This part of expansion of the immune system is regulated by cytokine receptors. However, not all the expanded B cells have the same affinity for the antigen, and only the cells with the highest affinity survive.

In multicellular organisms, apoptosis is not limited to T and B cells; various cells are programmed to commit suicide if survival signals are not received from their environment. These survival signals can be provided by the neighboring cells, extracellular matrix or growth factors (Cosman, 1994; Cosulich and Clarke, 1996; Laytragoon-Lewin, 1998; Raff, 1998; Wallach, 1996; Ware et al., 1996). In the absence of these survival signals, the cells undergo apoptosis, which occurs in the absence of new protein synthesis. This suggests that the proteins required to elicit apoptosis are already present in all cells, and to maintain cell viability apoptosis must be actively suppressed.

Apoptosis can be initiated through a number of receptors present on the surface of the cell. These receptors, called cell death receptors, are members of the tumor necrosis factor receptor family. In certain cell types, these receptors include those for TNFα, Fas, CD30 and CD40 (Cosman, 1994; Bachmann et al., 1999; Baker and Reddy, 1998). Conditions of stress, cell regeneration, expansion or selection result in induction of these "cell death" receptors. Receptors from this family act as receptor/ligand pairs in conjunction with ligands such as TNF, Fas ligand, CD30 ligand and CD40 ligand (Cosman, 1994; Bachmann et al., 1999; Inoue, 1997; Akagi et al., 1998; Baker and Reddy, 1998; Banchereau et al., 1997; Buske et al., 1997b; Choi, 1997; Clark and Hynes, 1997; Defrance et al., 1997).

The decision to undergo cell death can be regulated by a number of extrinsic and intrinsic cellular events. Intrinsic factors that can initiate cell death/apoptosis include intracellular events, such as DNA damage or metabolic or cell cycle perturbations caused by stress; or extracellular changes, such as withdrawal of survival signals provided by neighboring cells, growth factors or extracellular matrix, or activation of death receptors by binding their cognate ligand. An exogenous factor that may initiate apoptosis in one cell type may block apoptosis in another cell type. For example, estrogen prevents apoptosis of osteoblastic cells, but induces apoptosis of the bone resorbing cell—the osteoclast (Weinstein et al., 1998; Hughes et al., 1996).

The signaling pathways that follow the activation of the TNF related receptors converge at a common step involving proteases, such as caspases, which upon activation cleave proteins after every aspartic residue, leading to all the morphological features associated with apoptosis (Raff, 1998). The rate at which apoptosis progresses is regulated by a member of the Bcl-2 family of related proteins. They alter the apoptotic cell threshold or sensitivity of the cell to apoptosis.

CD40 is 50 Kd glycoprotein expressed on the surface of B cells, dendritic cells, normal epithelium and some epithelial carcinomas (Cosman, 1994; Laytragoon-Lewin, 1998; Gordon et al., 1994; Jabara et al., 1998; Kehry, 1996; Klaus et al., 1997; Laman et al., 1996; Mach et al., 1997a, 1998a, 1999; Sempowski et al., 1997; Tewari and Dixit, 1996; Tong and Stone, 1996; Briscoe et al., 1998). The ligand for CD40, CD40L, is expressed on activated T lymphocytes, human dendritic cells, human vascular endothelial cells, smooth muscle cells, and macrophages. CD40L exists on such cells as a trimeric structure, which induces oligomerization of its receptor upon binding.

In common with estrogen, CD40L prevents apoptosis in some cells and induces apoptosis in others. Specifically, CD40L induces apoptosis in transformed cells, but has the opposite effect on dendritic cells. Thus, depending on cell types or the stage of differentiation, these receptor ligand signaling pathways may promote cell survival or cell death.

The CD40 receptor then signals by binding to one or more TNF receptor associated factors (TRAF). In the case of CD40, TRAF 2 and TRAF 6 appear to activate the NFκB transcription factor. NFκB can inhibit or promote cell death, depending: on cell type (Thompson, 1999). In addition to its anti-apoptotic role, it regulates numerous genes such as cytokines and adhesion molecules that are critical in initiating, maintaining and resolving an immune/inflammatory response.

Apoptosis is prevented in B lymphocytes with high antigen affinity as these cells express CD40, which binds T-helper CD4+ T lymphocytes expressing CD40L. The mechanism by which CD40 promotes cell survival is by specific and transient upregulation of the Bcl-2-related protein Bcl-X1 (Josien et al., 1999). Lack of CD40 receptor engagement promotes cell death. Co-stimulatory receptors such as CD28 on T lymphocyte, or CD40 receptors on B lymphocytes, promote cell proliferation and play a very important role in preventing cell death in response to growth factor limitation or death receptor signal transduction. However, none of these pathways are dominant and the net survival of the cell in vivo depends on signals integrated from all these signaling pathways. Dendritic cells are the most potent antigen presenting cells known and initiate the adaptive immune response by interacting with naive T cells. Various members of the TNF receptor ligand family have been identified that serve as cell specific survival factors or anti-apoptotic factors for dendritic cells. These include TNFα, CD40L and TRANCE (tumor necrosis factor-related activation associated cytokine). TRANCE, also known as RANK ligand (RANKL, receptor activator of NFκB ligand), was originally described as a dendritic cell specific survival factor expressed by T lymphocytes (Bachmann et al., 1999; Mayumi et al., 1996; Josien et al., 1999; Fuller et al., 1998; Matsuzaki et al., 1998; Nakagawa et al., 1998; Yasuda et al., 1998a, b).

Increasing evidence supports the involvement of CD40/CD40L in autoimmune diseases and atherosclerosis (Durie et al., 1993; Elkon and Marshak-Rothstein, 1996; Mach et al., 1997; 1998a; 1998b; Levy et al., 1997). Blocking of CD40L by using an anti-CD40L antibody limits experimental autoimmune diseases, such as collagen-induced arthritis, lupus nephritis, graft vs. host disease, multiple sclerosis and thyroiditis (Callard et al., 1993; Durie et al., 1993; Ferrans et al., 1997; Flores-Romo et al., 1997; Funakoshi et al., 1997; Hackett and Dickler, 1999; Illei and Klippel, 1998; Lei et al., 1998; Liossis et al., 1997; Mach et al., 1998b; Maloney et al., 1999). CD40/CD40L are connected with the production of inflammatory cytokines, such as TNFα, and related cytokines, such as interleukin 1, which are elevated in conditions such as inflammatory arthritis.

Mutations in the extracellular domain of CD40L in humans results in X-linked hyper IgM syndrome, which is associated with absent IgG, IgA, and IgD immunoglobulin production. The patients who suffer from these mutations are susceptible to recurrent bacterial infections (Levy et al., 1997). CD40L or CD40 deficient mice, or mice treated with anti-CD40L antibodies, show an absence of germinal center formation and impaired development of B cell memory to T dependent antigens. In human keratinocytes, ligation of CD40 inhibits proliferation and induces differentiation.

Aberrant expression of CD40L and CD40 occurs in human atherosclerotic lesions but not normal arterial tissue. Inhibition of CD40 signaling using anti-CD40L antibody in mice susceptible to atherosclerosis (high cholesterol diet fed to mice lacking the low density lipoprotein receptor) resulted in a decrease in atherosclerotic lesions.

Recently an osteocyte-like cell line has been established with the characteristics of primary osteocytes (Kato et al., 1997). The cell line is designated MLO-Y4 (for murine long bone osteocyte) and was established from transgenic mice created using the osteocalcin promoter to drive the large T antigen expression. The cell line has extensive dendritic processes, the morphological feature of osteocytes in bones. They are similar to osteocytes in phenotype such as low expression of collagen type I and alkaline phosphatase and high expression of the bone specific protein, osteocalcin. Interestingly, this cell line does not express an antigen specifically found on early osteoblast progenitors, known as osteoblast specific factor 2 (OSF-2)—or more recently as "periostin" (Takeshita et al., 1993 ;Horiuchi et al., 1999). It is shown herein that although MLO-Y4 cells have a morphology similar to dendritic cells, they do not fimction as dendritic cells.

Prior to the present invention, the expression of CD40, the receptor for CD40L, was thought to be limited to B cells, follicular dendritic cells, epithelial cells, hematopoietic progenitor cells and some carcinomas. However, the present inventors have demonstrated for the first time that CD40 is expressed abundantly on bone cells, such as osteoblasts and osteocytes, as exemplified by the presence of CD40 on primary osteoblasts (PRI OBI), osteoblast cell lines (MC3T3, OCT-1 and 2T3) and an osteocyte cell line (MLO-Y4). The inventors also show that the addition of CD40L prevents glucocorticoid and TNFα induced apoptosis in these cells. These data have important implications in bone biology and treatment of disease, particularly in the treatment and prevention of steroid induced osteoporosis The present discoveries have also allowed the inventors to deduce the function of CD40 in bone physiology based on the present finding of CD40 expression on osteoblasts and osteocytes and, in part, from the function of CD40 as described in other cell types. They have also allowed a better understanding of the role of apoptosis in osteoporosis.

Apoptosis plays an important role in glucocorticoid/steroid-induced osteoporosis, the third most common cause of osteoporosis. This kind of bone loss usually affects the cortical and cancellous bone of the axial skeleton and is believed to be due to decreased bone formation, resulting from higher numbers of apoptotic/dead osteoblasts and osteocytes. Osteoblasts upon becoming embedded in mineralized matrix differentiate into osteocytes. Fewer numbers of these can account for changes seen with glucocorticoid induced bone disease, as is observed due to death/apoptosis in patients with glucocorticoid-induced osteoporosis (Weinstein et al., 1998).

The most common form of osteoporosis is post-menopausal, due to a lack of estrogen. Estrogen has been shown to be a viability factor for osteocytes in both humans and rodents (Tomkinson et al., 1997; Tomkinson et al., 1998). Estrogen has been reported to decrease bone resorbing cytokines, such as TNFα and Interleukin (IL-1) (Pacifici et al., 1991; Rickard et al., 1992). Delivery of both the soluble TNF receptor and an IL-1 receptor antagonist completely blocked bone loss due to ovariectomy in mice (Kimble et al., 1995), showing that a lack of estrogen leads to the increased production of cytokines responsible for bone loss.

Osteocytes are proposed to be the sensory cells in bone that sense and respond to mechanical strain. In addition to glucocorticoid treatment and post-menopausal osteoporosis, osteocyte apoptosis has been described in conditions of bone loss due to immobilization Noble et al., 1997). Clearly, bone accomodates or responds to strain—as was first stated by Julius Wolff in 1892. As with other cell types, osteocytes appear to undergo apoptosis during growth and during remodeling. However, mechanical loading appears to affect the number and distribution of apoptotic osteocytes. In cortical bone, Nobel and coworkers found that loading was associated with a reduction in numbers of apoptotic osteocytes (Noble et al., 1997). Therefore, mechanical strain may be important in maintaining osteocyte viability.

The present invention thus delineates the functions of CD40 in bone physiology as including a role in survival/cell death or apoptosis of osteocytes and osteoblasts; a role in growth and differentiation of osteoblasts to osteocytes; and a role in bone formation and modeling, by inducing matrix degrading enzymes such as metalloproteinases. The third role is supported by the fact that ligation of CD40 in human vascular smooth muscle cells induces the production of matrix degradation enzymes, such as interstitial collagenase (MMP-1), stromelysin (MMP-3), gelatinase B (MMP-9) and gelatinase A (MMP-2) (Mach et al., 1997a, b, 1998a, b, 1999)).

A fourth role of CD40 is in osteoclast formation, shown by the relationship of CD40 to TRANCE/RANKL, a molecule necessary for osteoclast formation (Josien et al., 1999), and in the connection between TRANCE/RANKL and NFκB. TRANCE/RANKL, initially described as a dendritic cell specific survival factor, has independently been reported to act as an osteoclast differentiation factor (Bachmann et al., 1999; Mayumi et al., 1996; Josien et al., 1999; Fuller et al., 1998; Matsuzaki et al., 1998; Nakagawa et al., 1998; Yasuda et al., 1998a, b). Osteoclasts are multinucleated cells that reabsorb bone and develop from hematopoietic cells of monocyte/macrophage lineage. Osteoclast formation is inhibited by osteoprotegerin (member of TNF receptor family) and their differentiation from osteoclast progenitors is induced by TRANCE/RANKL (Fuller et al., 1998; Yasuda et al., 1998a, b). NFκB, involved in the apoptosis pathway, has been reported to regulate genes involved in stimulating bone resorption (Thompson, 1999). Mice that have mutations in NFκB1, NFκB2 and M-CSF develop osteopetrosis because of defects in osteoclast differentiation.

CD40 and TRANCE/RANKL both belong to the TNF receptor/ligand family. The data of the present invention shows the expression of TRANCE/RANKL to be several log fold lower than CD40 expression in the MLO-Y4 cells. The fact that MLO-Y4 cells support osteoclast formation and express abundant CD40 suggests that CD40 plays an important role in osteoclast formation. It has also been shown that osteoprotogerin, an inhibitor of osteoclast formation is increased B cells and dendritic cells by CD40 stimulation (Yun et al., 1998).

The discovery by the inventors of CD40 expression on osteoblasts and osteocytes leads to a number of clinical applications. The administration of one or more of CD40 ligand or CD40 agonist for use in the amelioration or prevention of bone diseases, such as osteoporosis and osteonecrosis in patients who receive high doses of steroids, is now possible. As the administration of glucocorticoids/steroids is the third most common cause of osteoporosis, the new treatment made possible by the present invention is a much sought after development.

All individuals are susceptible to steroid induced bone loss. All patients of all ages, both sexes and all races are susceptible. The rate of bone loss can be rapid and the net loss significant. Such bone loss is due to decreased bone formation that results from higher numbers of apoptotic/dead osteoblasts. Thus, prevention of apoptosis or cell death of the osteoblast and osteocytes, according to the present invention, will ameliorate the bone loss seen with glucocorticoid administration.

The treatment methods of the invention encompass patients with autoimmune diseases, such as lupus nephritis, Takayasu's arteritis, Wegeners granulomatosis, anti-glomerular basement membrane nephritis, myositis, scleroderma and idiopathic autoimmune thrombocytopenia. Further indications are in organ transplantation, including bone marrow transplantation, where the use of prednisone and cyclosporin administered together causes rapid bone loss, chemotherapy regimens containing steroids for hematological and solid organ malignancies, and chronic use of steroids in asthma and chronic obstructive lung diseases. Additionally, the compositions and methods of the present invention can be used in the treatment or prevention of bone diseases and growth retardation in children who are treated with long term steroids. This includes children with those conditions listed above, as well as children with nephrotic/nephritic syndrome.

Osteoporosis occurs most commonly in post-menopausal women and elderly patients. Such individuals are prime candidates for treatment with CD40 ligands and/or agonists according to this invention, thereby counteracting post-menopausal bone loss and bone loss in the elderly. Post menopausal bone loss may be due to increased cytokine production and/or increased osteocyte apoptosis. Estrogen has been shown to be a viability factor for osteocytes in humans. The prevention of osteoblast/osteocyte cell death by CD40L according to the present invention will reduce and/or abrogate the effects of a lack of estrogen. Thus, the invention provides new treatments for the most prevalent forms of osteoporosis.

I. Bone Cells

The three major types of bone cells are osteocytes, osteoblasts and osteoclasts. Osteocytes are by far the most abundant type of bone cells, with approximately ten times more osteocytes than osteoblasts (Parfitt, 1977), and with osteoblasts far more abundant than osteoclasts. Each of these different types of bone cell has a different phenotype, morphology and function. The present invention utilizes the discovery by the inventors that the CD40 receptor is present on cells such as osteocytes and osteoblasts to provide, in a general sense, methods of preventing osteocyte and osteoblast cell apoptosis using CD40 ligands and/or agonists.

A. Osteocytes

Osteocytes are the most abundant cell type in bone (Nijweide et al., 1996). Osteocytes are localized within the mineral matrix at regular intervals, and arise from osteoblasts. During their transition from osteoblasts, osteocytes maintain certain osteoblastic features, but acquire several osteocyte-specific characteristics.

Mature osteocytes are stellate shaped or dendritic cells enclosed within the lacuno-canalicular network of bone. Long, slender cytoplasmic processes radiate from the central cell body, with most of the processes perpendicular to the bone surface. The processes connect the osteocyte to neighboring osteocytes and to the cells lining the bone surface. This is consistent with the currently postulated role of osteocyte network as the main sensor and communication system in bone.

Due to their location in bone, embedded in the mineral matrix, osteocytes were long resistant to isolation and analysis. Van der Plas and Nijweide (1992) were among the first to isolate and characterize osteocytes. However, recently, a number of osteocyte markers have been identified. Among the best markers for osteocytes in vitro are their stellate morphology, which they reacquire in culture (Van der Plas and Nijweide, 1992), and their reaction with osteocyte-specific monoclonal antibodies. A number of monoclonal antibodies specific for avian osteocytes have been described, including OB7.3, OB37.11 and SB5 (Nijweide and Mulder, 1986; Nijweide et al., 1988; Bruder and Caplan, 1990), but the antigen(s) for these antibodies has not been identified, and none of these antibodies cross-react with mammalian cells.

A monoclonal antibody (OB/M) has been reported that reacts with newly embedded human osteocytes, but not with osteocytes present in the heavy-mineralized matrix (Walsh et al., 1994). The antigen for this antibody has not yet been identified, but is known to be intracellular. Markers identified on human osteocytes include CD44, a trans-membrane glycoprotein with cell-cell and cell-matrix adhesion functions (Hughes et al., 1994; Nakamura et al., 1995), integrins, and the parathyroid hormone (PTH), 1,25-dihydroxy vitamin $D_3$ and prostaglandin receptors (Van der Plas et al., 1994; Boivin et al., 1987; Lean et al., 1995).

B. Osteoblasts

Osteoblasts are the skeletal cells responsible for bone formation, and thus synthesize and regulate the deposition and mineralization of the extracellular matrix of bone (Aubin and Liu, 1996). Four maturational stages have been identified in osteoblast development, preosteoblast, osteoblast, osteocyte and bone lining cell. Osteoblasts are postproliferative, cuboidal, strongly alkaline phosphatase positive cells the line the bone matrix at sites of active matrix production. Osteoblasts also synthesize a number of phenotype-specific or phenotype-associated macromolecules, including bone matrix proteins, hormone receptors, cytokines and growth factors.

A number of different markers have been identified in preosteoblasts, osteoblasts and bone lining cells, mainly in rat, mouse and human (Aubin and Liu, 1996). Markers identified in rat include collagen type I, osteopontin, bone sialoprotein, osteocalcin, insulin-like growth factor I, epidermal growth factor receptor, parathyroid hormone receptor, E11 antigen and c-fos. Markers identified in mice include insulin-like growth factor I, insulin-like growth factor II, insulin-like growth factor I receptor, insulin-like growth factor II receptor, bone morphogenetic protein type I receptor, 1,25-dihydroxyvitamin $D_3$ receptor, human X-box-binding protein 1 and TIMP. Markers identified in human include collagen type I, collagen type III, bone sialoprotein, osteocalcin, IL-1β, IL-6, insulin-like growth factor I, insulin-like growth factor II, insulin-like growth factor I receptor, integrins, including $\alpha_4$, $\alpha_v$, $\alpha_5\beta_1$ and $\beta_3\beta_5$, thrombospondin, fibronectin, vitronectin, biglycan, decorin and c-fos. To date, no antibodies specific for osteoblasts have been reported, with the exception of the osteocyte antibodies discussed in the previous section.

C. Osteoclasts

Osteoclasts are multinucleated giant cells with resorbing activity of mineralized bone (Suda et al., 1996). Osteoclast progenitor cells are hemopoietic in origin, traveling to bone from tissues such as bone marrow through the circulating blood. There, the progenitor cells proliferate and differentiate into osteoclasts through cell-cell interaction with osteoblastic stromal cells. The importance of the interaction of the osteoclast progenitor cells with stromal cells was suggested by studies of congenital osteopetrotic mice. While bone disorders in certain congenital mutants can be cured by transplantation of hemopoeitic cells, osteopetrotic (op/op; Marks et al., 1984) and osteosclerotic (oc/oc; Seifert and Marks, 1985) mice cannot be cured by hemopoeitic cells transplantation, implicating osteoblastic stromal cells in osteoclast development.

Signals involved in osteoclast development include 1α,25-dihydroxy vitamin $D_3$ and cAMP mediated signals, and gp 130 mediated signals by cytokines such as IL-11, oncostatin M and leukemia inhibitory factor. Macrophage colony-stimulating factor (M-CSF) and the third component of complement (C3) have also been reported to have a role in osteoclast development. Estrogen also may play a role in the development of osteoclasts.

A number of markers of osteoclasts have been reported (Suda et al., 1996), including tartrate-resistant acid phosphatase (TRAP) and calcitonin receptors, carbonic anhydrase II, α- and α-subunits of vitronectin receptors, vacuolar proton ATPase, $p60^{c-src}$, $\alpha_v\beta_3$ integrin, matrix metalloproteinase 9, an osteoclast-specific cysteine protease (OC-2) and protein phosphatase ε.

D. Bone Cell Lines

The development of bone cell lines has helped to elucidate the function and phenotype of osteoblasts and osteocytes. A number of osteoblast cell lines are known, including MC3T3-E1, which was established from normal mouse calvaria (Franceschi and Iyer, 1992), OCT-1, which was established from osteocalcin promoter driven T-antigen transgenic mouse calvaria (Chen et al., 1995), 2T3 (Ghosh-Choudhury et al., 1996), UMR201 (Ng et al., 1988), RCT1 (Heath et al., 1989), UMR106, ROS 17/2.8, SaOS-2 and MG-63 (Aubin and Liu, 1996).

In addition to the osteoblast cell lines that have been described, an osteocyte cell line, MLO-Y4, has recently been developed (Kato et al., 1997; Bonewald, 1999; each specifically incorporated herein by reference). To date, this is the only known osteocyte cell line.

II. CD40 Ligand and Agonist Compositions

A. CD40 Ligand (gp39) Compositions

CD40 ligand (CD40-L or gp39) is a type II membrane polypeptide having an extracellular region at its C-terminus, a transmembrane region and an intracellular region at its N-terminus. To date, the CD40 ligand has been cloned and sequenced, and nucleic acid and amino acid sequences have been reported from human (GenBank accession numbers Z15017/S49392, D31793-7, X96710, L07414 and X67878/S50586), murine (GenBank accession number X65453), bovine (GenBank accession number Z48469), canine (GenBank accession number AF086711), feline (GenBank accession number AF079105) and rat (GenBank Accession Numbers AF116582, AF013985).

Additional CD40 ligand nucleic acid and amino acid sequences are disclosed in U.S. Pat. Nos. 5,565,321 and 5,540,926, incorporated herein by reference, and mutant CD40 ligand sequences are disclosed in U.S. Pat. No. 5,716,805 and U.S. patent applications, Ser. Nos. 08/484,624 and 09/088,913, each of which is incorporated herein by reference. A preferred mutation is a cysteine to tryptophan mutation at position 194 of SEQ ID NO:1. In other species, this mutation is the same in the bovine sequence; and is at position 193 in the canine and feline sequences. Also contemplated for use in certain aspects of the invention are the human CD40 binding protein, disclosed in Hu et al. (1994; GenBank Accession Number U15637), and high density, membrane bound CD40 ligand, disclosed in U.S. Pat. No. 5,817,516 (incorporated herein by reference). Exemplary CD40 ligand (gp39) and CD40 binding protein nucleic acid and amino acid sequences are listed in Table 1 below. Each of the CD40 ligand nucleic acid and amino acid compositions disclosed herein are contemplated for use in all aspects of the present invention.

TABLE 1

CD40 Ligand Compositions

| Composition | Source | Location |
|---|---|---|
| CD40 Ligand | Human | GenBank Accession Numbers Z15017/S49392, D31793, D31794, D31795, D31796, D31797, X96710, L07414, X67878/S50586 |
| CD40 Ligand | Murine | GenBank Accession Number X65453 |
| CD40 Ligand | Bovine | GenBank Accession Number Z48469 |
| CD40 Ligand | Canine | GenBank Accession Number AF086711 |
| CD40 Ligand | Feline | GenBank Accession Number AF079105 |
| CD40 Ligand | Rat | GenBank Accession Numbers AF116582, AF013985 |
| CD40 Ligand and Mutations in CD40 Ligand | Human | U.S. Pat. No. 5,565,321 |
| CD40 Ligand | Human | U.S. Pat. No. 5,540,926 |
| CD40 Ligand and Mutations in CD40 Ligand | Human, Murine | U.S. Pat. No. 5,716,805 |
| CD40 Binding Protein | Human | GenBank Accession Number U15637 |

The protein sequence of the full length human CD40 ligand extends from between about amino acid 1 and about amino acid 261 in SEQ ID NO:2, and is encoded by the nucleic acid sequence between about nucleotide 22 to about nucleotide 804 of SEQ ID NO:1. The full length protein and encoding nucleic acid sequences of the murine, bovine, canine, feline and rat counterparts of the CD40 ligand extend from between about amino acid 1 to about amino acid 260, encoded by the nucleic acid sequence between about nucleotide 13 to about nucleotide 792; from between about amino acid 1 to about amino acid 261, encoded by the nucleic acid sequence between about nucleotide 15 to about nucleotide 797; from between about amino acid 1 to about amino acid 260, encoded by the nucleic acid sequence between about nucleotide 5 to about nucleotide 784; from between about amino acid 1 to about amino acid 260, encoded by the nucleic acid sequence between about nucleotide 5 to about nucleotide 784; and from between about amino acid 1 to about amino acid 260, encoded by the nucleic acid sequence between about nucleotide 1 to about nucleotide 780, respectively. Such murine, bovine, canine, feline and rat sequences are also disclosed in U.S. provisional application Serial No. 60/151,250, filed Aug. 27, 1999, incorporated herein by reference.

Soluble versions of CD40 ligand can be made from the extracellular region, or a fragment thereof, and a soluble CD40 ligand has been found in culture supernatants from cells that express a membrane-bound version of CD40 ligand, such as EL-4 cells. The protein sequence of the extracellular region of human CD40 ligand extends from between about amino acid 47–50 to about amino acid 261 in SEQ ID NO:2, and is encoded by the nucleic acid sequence between about nucleotide 160–169 to about nucleotide 804 of SEQ ID NO:1. The protein sequence of the extracellular region of murine, bovine, canine, feline and rat CD40 ligand extends from between about amino acid 47–50 to about amino acid 260 or 261 in each case, which are encoded by the nucleic acid sequences of from between about nucleotide 151–160 to about nucleotide 792; about nucleotide 153–162 to about nucleotide 797; about nucleotide 143–152 to about nucleotide 784; about nucleotide 143–152 to about nucleotide 784; and from about nucleotide 139–148 to about nucleotide 780, respectively. Such murine, bovine, canine, feline and rat sequences are also disclosed in U.S. provisional application Serial No. 60/151,250, filed Aug. 27, 1999, incorporated herein by reference.

Additional soluble versions of the CD40 ligand are contemplated for use in the present invention. For example, a soluble version comprising the extracellular region of human CD40 ligand extending from between about amino acid 113–120 to about amino acid 261 in SEQ ID NO:2, encoded by the nucleic acid sequence between about nucleotide 358–379 to about nucleotide 804 of SEQ ID NO:1. The counterpart protein sequences of the murine, bovine, canine, feline and rat CD40 ligands also extend from between about amino acid 113–120 to about amino acid 260 or 261 in each case and are encoded by the nucleic acid sequences from between about nucleotide 349–370 to about nucleotide 792, about nucleotide 351–372 to about nucleotide 797, about nucleotide 341–362 to about nucleotide 784, about nucleotide 341–362 to about nucleotide 784, and about nucleotide 337–358 to about nucleotide 780, respectively. These murine, bovine, canine, feline and rat sequences are also disclosed in U.S. provisional application Serial No. 60/151,250, filed Aug. 27, 1999, incorporated herein by reference.

The soluble CD40 ligand compositions of the present invention are preferably operatively linked together to form oligomers, including, but not limited to, dimers, trimers, tetramers, and even larger oligomers, as long as the anti-apoptotic effect of the CD40 ligand oligomer on bone cells is maintained without significant impairment. The anti-apoptotic effect of the CD40 ligand oligomers on bone cells such as osteocytes and/or osteoblasts can be assessed using any of the apoptosis assays described in detail herein.

The soluble CD40 ligand monomers may be joined using recombinant DNA techniques or synthetic chemistry techniques. Each of these techniques are routinely employed and well known to those of skill in the art, and are further exempted in Example 1 and by the details set forth below.

1. Recombinant Fusion Proteins

In certain embodiments of the present invention, the soluble CD40 ligand compositions of the invention are fusion proteins prepared by molecular biological techniques. Fusion proteins are polypeptides that comprise two or more regions derived from different, or heterologous, proteins or peptides. The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers. Fusion proteins can comprise several sequences, including a leader (or signal peptide) sequence, a linker sequence, an oligomer-forming sequence, such as a leucine zipper sequence (SEQ ID NO:3), the lung surfactant protein D (SPD) trimerization domain (Hoppe et al., 1994; SEQ ID NO:4), a linker sequence, such as one comprising four glycines, a serine, five glycines and a serine, or any of the linker sequences disclosed in U.S. Pat. No. 5,073,627 (incorporated herein by reference), and sequences encoding highly antigenic moieties that provide a means for facile purification or rapid detection of a fusion protein. CD40 ligand-leucine zipper fusion proteins, and methods for making these fusion proteins, are described in detail in U.S. Pat. No. 5,716,805, incorporated herein by reference.

In general, to prepare a fusion protein, one would join at least a first DNA coding region, such as a gene or cDNA, encoding at least a first peptide or polypeptide to at least a second DNA coding region (i.e., gene or cDNA) encoding at least a second peptide or polypeptide. This typically involves preparing an expression vector that comprises, in the same reading frame, a first DNA segment encoding the first peptide or polypeptide operatively linked to a second DNA segment encoding the second peptide or polypeptide. The sequences are attached in a manner such that translation of the total nucleic acid yields the desired fusion proteins of the invention. Expression vectors contain one or more promoters upstream of the inserted DNA regions that act to promote transcription of the DNA and to thus promote expression of the encoded recombinant protein. This is the meaning of "recombinant expression".

When produced via recombinant DNA techniques, the soluble CD40 ligand compounds of the invention that are capable of self-oligomerization are referred to as "fusion proteins". It is to be understood that such fusion proteins contain, at least, a soluble CD40 ligand sequence and an oligomer-forming sequence as defined in this invention, and that these sequences are operatively attached. The fusion proteins may also include additional peptide sequences, such as leader sequences, involved in the secretion of proteins from cells, antigenic sequences, involved in the identification and/or purification of the fusion protein, or peptide spacers, which operatively attach the soluble CD40 ligand and oligomer-forming sequences, so long as such additional sequences do not appreciably affect the activities of the resultant fusion protein.

An exemplary signal peptide is the amino terminal 25 amino acids of the leader sequence of murine interleukin-7 (IL-7; Namen et al., 1988). Other signal peptides may also be employed furthermore, certain nucleotides in the IL-7 leader sequence can be altered without altering the amino acid sequence. Additionally, amino acid changes that do not affect the ability of the IL-7 sequence to act as a leader sequence can be made.

An exemplary antigenic sequence is the Flag® octapeptide (Hopp et al., 1988, specifically incorporated herein by reference), which does not alter the biological activity of fusion proteins, is highly antigenic and provides an epitope reversibly bound by a specific monoclonal antibody, enabling rapid detection and facile purification of the expressed fusion protein. The Flag® sequence is also specifically cleaved by bovine mucosal enterokinase at the residue immediately following the Asp-Lys pairing. Fusion proteins capped with this peptide may also be resistant to intracellular degradation in E. coli. A murine monoclonal antibody that binds the Flag® sequence has been deposited with the ATCC under accession number HB 9259; methods of using the antibody in purification of fusion proteins comprising the Flag® sequence are described in U.S. Pat. No. 5,011,912, incorporated herein by reference.

Non-cleavable peptide linker sequences may be provided to operatively attach the two peptide or polypeptide sequences, if desired. Equally, peptides with unique cleavage sites could be inserted between the two sequences. One advantage of recombinant expression is that the linking regions can be readily manipulated so that, e.g., their length and/or amino acid composition is readily variable. Suitable linker sequences (1) will adopt a flexible extended conformation, (2) will not exhibit a propensity for developing an ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence.

Other near neutral amino acids, such as Thr and Ala, may also be used in the linker sequence. The length of the linker sequence may vary without significantly affecting the biological activity of the fusion protein. Linker sequences are unnecessary where the proteins being fused have non-essential N- or C-terminal amino acid regions that can be used to separate the functional domains and prevent steric interference. Exemplary linker sequences are described in U.S. Pat. Nos. 5,073,627 and 5,108,910, the disclosures of which are incorporated by reference herein.

It will be understood that the recombinant fusion proteins may differ from those oligomeric constructs generated by chemically cross-linking the so-called naturally-produced proteins or peptides. In particular, the degree of post-translational modifications, such as, for example, glycosylation and phosphorylation may be different between recombinant fusions and chemical fusions of the same two proteins. This is not contemplated to be a problem, however, as those of skill in the art will know to confirm that a recombinant fusion protein functions as intended before use in a clinical setting.

When an oligomeric fusion protein is formed from the extracellular portion of a transmembrane protein, a DNA sequence encoding an oligomer-forming domain, such as a leucine zipper domain, is fused to a DNA sequence encoding an extracellular region of the transmembrane protein. The members of the fusion protein are joined such that the oligomer-forming domain of the fusion protein is located in the same orientation relative to the fusion protein as the transmembrane and intracytoplasmic reigns of the native transmembrane protein. An oligomeric fusion protein will be stabilized by the coiled-coil interaction of the leucine zipper domain. Thus, in one example, in a fusion protein comprising an extracellular region derived from the CD40 ligand, a type II transmembrane protein, the oligomer-forming domain, a leucine zipper sequence, is fused to the amino-proximal end of the extracellular region. In a fusion protein derived from a type I transmembrane protein, the oligomer-forming domain would be fused to the carboxy-proximal end of the extracellular region of the type I transmembrane protein. Other transmembrane proteins traverse the cell membrane more than once. Such transmembrane proteins will have two or more different extracellular regions. Soluble, oligomeric fusion proteins may also be prepared from two or more of such different extracellular regions from the same transmembrane protein.

2. Zipper Domains

Leucine zippers were originally identified in several DNA-binding proteins (Landschulz et al., 1988). Zipper domain is a term used to refer to a conserved peptide domain present in these (and other) proteins, which is responsible for oligomerization of the proteins. The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4, a heat-stable DNA-binding protein found in rat liver (C/EBP; Landschulz et al., 1989), and the sterol regulatory element binding protein (SREBP; U.S. Pat. Nos. 5,498,696 and 5,527,690). Two nuclear transforming proteins, fos and jun, also contain zipper domains, as does the gene product of the murine proto-oncogene, c-myc (Landschulz et al., 1988). The products of the nuclear oncogenes fos and jun comprise zipper domains and preferentially form a heterodimer (O'Shea et al., 1989; Turner and Tjian, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, 1989; Britton, 1991; Delwart and Mosialos, 1990). The zipper domains in these fusogenic viral proteins are near the transmembrane region of the proteins, and it has been suggested that the zipper domains could contribute to the oligomeric structure of the fusogenic proteins. Oligomerization of fusogenic viral proteins is involved in fusion pore formation (Spruce et al, 1991). Zipper domains have also been recently reported to play a role in oligomerization of heat-shock transcription factors (Rabindran et al., 1993).

Zipper domains fold as short, parallel coiled coils (O'Shea et al., 1991). The general architecture of the parallel coiled coil has been well characterized, with a "knobs-into-holes" packing as proposed by Crick in 1953. The dimer formed by a zipper domain is stabilized by the heptad repeat, designated $(abcdefg)_n$, according to the notation of McLachlan and Stewart (1975), in which residues a and d are generally hydrophobic residues that line up on the same face of a helix, with d being a leucine. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek et al., 1991). The synthesis of a triple-stranded a-helical bundle has recently been reported (Lovejoy et al., 1993), in which the helices run up-up-down. Studies on this structure confirmed that hydrophobic stabilization energy provides the main driving force for the formation of coiled coils from helical monomers. These studies also indicate that electrostatic interactions contribute to the stoichiometry and geometry of coiled coils.

Several studies have indicated that conservative amino acids may be substituted for individual leucine residues with minimal decrease in the ability to dimerize; multiple changes, however, usually result in loss of this ability (Landschulz et al., 1989; Turner and Tjian, 1989; Hu et al., 1990). Additional studies have reported that a number of different amino residues can be substituted for the leucine residues in the zipper domain of GCN4, and further found that some GCN4 proteins containing two leucine substitutions were weakly active (van Heeckeren et al., 1992). Mutation of the first and second heptadic leucines of the zipper domain of the measles virus fusion protein (MVF) did not affect syncytium formation (a measure of virally-induced cell fusion); however, mutation of all four leucine residues prevented fusion completely (Buckland et al., 1992). None of the mutations affected the ability of MVF to form a tetramer.

Recently, amino acid substitutions in the a and d residues of a synthetic peptide representing the GCN4 zipper domain have been found to change the oligomerization properties of the zipper domain. When all residues at position a are changed to isoleucine, the zipper still forms a parallel dimer. When, in addition to this change, all leucine residues at position d are also changed to isoleucine, the resultant peptide spontaneously forms a trimeric parallel coiled coil in solution. Substituting all amino acids at position d with isoleucine and at position a with leucine results in a peptide that tetramerizes. Peptides containing these substitutions are still referred to as zipper domains since the mechanism of oligomer formation is believed to be the same as that for traditional leucine zipper domains such as those described above.

3. Biochemical Cross-linkers

Cross-linking reagents can also be used to form molecular bridges that tie together functional groups of two different peptides or polypeptides. To link two different peptides or proteins in a step-wise manner, heterobifunctional cross-linkers, such as those disclosed in Ji (1983) and Srinivasachar and Neville (1989), as well as those shown below in Table 2, can be used.

TABLE 2

Heterobifunctional Cross-Linkers

| Linker | Reactive Toward | Advantages and Applications | Spacer Arm Length After Cross-Linking |
| --- | --- | --- | --- |
| SMPT | Primary amines Sulfhydryls | Greater stability | 11.2 Å |
| SPDP | Primary amines Sulfhydryls | Thiolation; Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extended spacer arm; Water-soluble | 15.6 Å |
| SMCC | Primary amines Sulfhydryls | Stable maleimide reactive group; Enzyme-antibody conjugation; Hapten-carrier protein conjugation | 11.6 Å |
| Sulfo-SMCC | Primary amines Sulfhydryls | Stable maleimide reactive group; Water-soluble; Enzyme-antibody conjugation | 11.6 Å |
| MBS | Primary amines Sulfhydryls | Enzyme-antibody conjugation; Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm; Enzyme-antibody conjugation | 14.5 Å |
| Sulfo-SMPB | Primary amines Sulfhydryls | Extended spacer arm; Water-soluble | 14.5 Å |

TABLE 2-continued

Heterobifunctional Cross-Linkers

| Linker | Reactive Toward | Advantages and Applications | Spacer Arm Length After Cross-Linking |
|---|---|---|---|
| EDC/Sulfo-NHS | Primary amines Carboxyl groups | Hapten-Carrier conjugation | 0 |
| ABH | Carbohydrates Nonselective | Reacts with sugar groups | 11.9 Å |

An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein or peptide and through the thiol reactive group, the cross-linker, already tied up to the first protein or peptide, reacts with the cysteine residue (free sulfhydryl group) of the other protein or peptide.

It can therefore be seen that the preferred CD40 ligand polypeptides will generally have, or be derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking.

The spacer arm between the two reactive groups of a cross-linker may have various length and chemical compositions. A longer spacer arm allows for better flexibility of the conjugate components, while some particular components in the bridge (e.g., benzene group) may lend extra stability to the reactive group or an increased resistance of the chemical link to the action of various agents (e.g., disulfide bond resistant to reducing agents). The use of peptide spacers, such as a four amino acid long peptide with alternating leucine and alanine residues, is also contemplated.

It is preferred that a cross-linker having reasonable stability in blood will be employed. Numerous types of disulfide-bond containing linkers are known that can be successfully employed to conjugate CD40 ligand polypeptides and oligomerization sequences. Linkers that contain a disulfide bond that is sterically hindered may prove to give greater stability in vivo, preventing dissociation of the CD40 ligand oligomer prior to binding at the site of action. These linkers are thus one preferred group of linking agents.

A preferred cross-linking reagent is SMPT, which is a bifunctional cross-linker that can be used in the present invention. SMPT contains a disulfide bond that is "sterically hindered" by an adjacent benzene ring and methyl groups. It is believed that steric hindrance of the disulfide bond serves a function of protecting the bond from attack by thiolate anions, such as glutathione, which can be present in tissues and blood, and thereby help in preventing dissociation of the CD40 ligand oligomer prior to the delivery to bone cells.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane. The use of such cross-linkers is well understood in the art.

Once conjugated, the CD40 ligand oligomer will generally be purified to separate the conjugate from unconjugated molecules and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use.

B. CD40 Agonists

Anti-CD40 antibodies have been shown to bind to and activate CD40, in certain aspects in the presence of IL-4 or IL-6 (Clark, 1990), thus preventing apoptosis. In addition to the HM40-3, 3/23 monoclonal antibody described herein below, exemplary anti-CD40 antibodies contemplated for use in the present invention include, but are not limited to, the anti-CD40 monoclonal antibodies mAb89 and EA-5 (Buske et al., 1997a), 17:40 and S2C6 (Bjorck et al., 1994), G28-5 (Ledbetter et al., 1994), G28-5 sFv (Ledbetter et al., 1997), as well as those disclosed in U.S. Pat. Nos. 5,801,227, 5,677,165 and 5,874,082, each incorporated herein by reference. A number of these antibodies are also commercially available, from sources such as Alexis Corporation (San Diego, Calif.) and Pharmingen (San Diego, Calif.).

Other anti-CD40 antibodies can be made, using all or a portion of the human CD40 amino acid sequence, disclosed in U.S. Pat. No. 5,849,898 (incorporated herein by reference), the mouse CD40 amino acid sequence (GenBank Accession number M83312), or the bovine CD40 amino acid sequence (GenBank Accession number U57745), using the techniques described in detail herein below.

III. Nucleic Acid Compositions

Compositions for use in the present invention include isolated DNA segments and recombinant vectors encoding CD40 ligand and/or CD40 agonist proteins, such as gp39 proteins, and recombinant host cells that express CD40 ligand and/or CD40 agonist proteins, using the nucleic acid sequences disclosed herein. DNA segments, recombinant vectors, recombinant host cells and expression methods involving the CD40 ligand and/or CD40 agonist sequences are thus provided. Each of the nucleic acid sequences listed in Table 1 are included within all aspects of the following description.

The present invention concerns the use of DNA segments, isolatable from eukaryotic cells, that are free from total genomic DNA and that are capable of expressing a CD40 ligand and/or CD40 agonist protein or polypeptide. As used herein, the term "DNA segment" refers to a DNA molecule that has been isolated free of total genomic DNA of a particular species. Therefore, for example, a DNA segment encoding a gp39 protein refers to a DNA segment that contains gp39 coding sequences yet is isolated away from, or purified free from, total genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified CD40 ligand and/or CD40 agonist gene refers to a DNA segment including wild-type, polymorphic or mutant CD40 ligand and/or CD40 agonist coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides, domains, peptides, fusion proteins and mutants.

"Isolated substantially away from other coding sequences" means that the gene of interest, for example a CD40 ligand and/or CD40 agonist gene, forms the significant part of the coding region of the DNA segment, and that the DNA segment does not contain large portions of naturally-occurring coding DNA, such as large chromosomal fragments or other functional genes or protein coding regions. Of course, this refers to the DNA segment as originally isolated, and does not exclude genes or coding regions later added to the segment by the hand of man.

In particular embodiments, the invention concerns the use of isolated DNA segments and recombinant vectors incorporating DNA sequences that encode, for example, a CD40 ligand and/or CD40 agonist protein or peptide, that includes within its amino acid sequence a contiguous amino acid sequence in accordance with, or essentially as set forth in, the amino acid sequences disclosed herein.

The term "a sequence essentially as set forth in" means that the sequence substantially corresponds to a portion of the disclosed amino acid sequence, and has relatively few amino acids that are not identical to, or a biologically functional equivalent of, the amino acids of the disclosed amino acid sequence.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or fimctionally equivalent to the amino acids of the disclosed sequences will be sequences that are "essentially as set forth in" the disclosed amino acid sequences, provided the biological activity of the protein is maintained.

In certain other embodiments, the invention concerns the use of isolated DNA segments and recombinant vectors that include within their sequence a nucleic acid sequence essentially as set forth in the nucleic acid sequences disclosed herein. The term "essentially as set forth in" is used in the same sense as described above and means that the nucleic acid sequence substantially corresponds to a portion of the disclosed nucleic acid sequence and has relatively few codons that are not identical, or functionally equivalent, to the codons of the disclosed nucleic acid sequence.

The term "functionally equivalent codon" is used herein to refer to codons that encode the same amino acid, such as the six codons for arginine or serine, and also refers to codons that encode biologically equivalent amino acids (see Table 3).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting flanking regions, and allowing for the degeneracy of the genetic code, sequences that have between about 70% and about 79%; or more preferably, between about 80% and about 89%; or even more preferably, between about 90% and about 99%; of nucleotides that are identical to the nucleotides of the disclosed nucleic acid sequences will be sequences that are "essentially as set forth in" these sequences.

Sequences that are essentially the same as those set forth in the disclosed nucleic acid sequences may also be functionally defined as sequences that are capable of hybridizing to a nucleic acid segment containing the complement of the disclosed nucleic acid sequences under relatively stringent conditions.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Another exemplary, but not limiting, standard hybridization is incubated at 42° C. in 50% formamide solution containing dextran sulfate for 48 hours and subjected to a final wash in 0.5×SSC, 0.1% SDS at 65° C.

The nucleic acid segments for use in the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It will also be understood that this invention is not limited to the use of the particular disclosed nucleic acid and amino acid sequences. Recombinant vectors and isolated DNA segments for use in the present invention may therefore variously include these coding regions themselves, coding regions bearing selected alterations or modifications in the basic coding region, or they may encode larger polypeptides that nevertheless include such coding regions or may encode biologically functional equivalent proteins or peptides that have variant amino acids sequences.

Certain of the DNA segments for use in the present invention encompass biologically functional equivalent proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine DNA binding activity at the molecular level.

One may also prepare fusion proteins and peptides, e.g., where the protein coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length amino acid sequences as set forth in herein.

IV. Protein and Polypeptide Compositions

Compositions for use in the present invention also include purified, and in preferred embodiments, substantially purified, CD40 ligand and/or CD40 agonist proteins, polypeptides and peptides, for example gp39 proteins and peptides. The term "purified CD40 ligand and/or CD40 agonist protein or peptide", for example "purified gp39 protein or peptide" as used herein, is intended to refer to, for example, a wild-type, polymorphic or mutant CD40 ligand and/or CD40 agonist proteinaceous composition, isolatable from mammalian cells or recombinant host cells, wherein the wild-type, polymorphic or mutant CD40 ligand and/or CD40 agonist protein or peptide is purified to any degree relative to its naturally-obtainable state, i.e., relative to its purity within a cellular extract. A purified CD40 ligand and/or CD40 agonist protein or peptide therefore also refers to a CD40 ligand and/or CD40 agonist protein or peptide free from the environment in which it naturally occurs.

Proteins for use in the present invention may be full-length proteins, while in certain aspects of the invention they may also be less then full-length proteins, such as individual domains, regions or even epitopic peptides. Where less than full-length proteins are concerned the most preferred will be those containing predicted immunogenic sites and those containing the functional domains identified herein.

Generally, "purified" will refer to, for example, a CD40 ligand and/or CD40 agonist protein or peptide composition that has been subjected to fractionation to remove various non-wild-type, polymorphic or mutant CD40 ligand and/or CD40 agonist protein or peptide components, and which composition substantially retains its CD40 activation and/or antiapoptotic activity.

Where the term "substantially purified" is used, this will refer to a composition in which the protein or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A polypeptide or protein that is "purified to homogeneity," as applied to the present invention, means that the polypeptide or protein has a level of purity where the polypeptide or protein is substantially free from other proteins and biological components. For example, a purified polypeptide or protein will often be sufficiently free of other protein components so that degradative sequencing may be performed successfully.

Various methods for quantifying the degree of purification the disclosed proteins or peptides will be known to those of skill in the art in light of the present disclosure. These include, for example, determining the number of polypeptides within a fraction by gel electrophoresis. Assessing the number of polypeptides within a fraction by SDS/PAGE analysis will often be preferred in the context of the present invention as this is straightforward.

To purify a protein or peptide, such as a CD40 ligand and/or CD40 agonist protein or peptide, a natural or recombinant composition comprising at least some CD40 ligand and/or CD40 agonist proteins or peptides will be subjected to fractionation to remove various non-CD40 ligand and/or CD40 agonist protein or peptide components from the composition. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, and affinity chromatography; isoelectric focusing; gel electrophoresis; and combinations of such and other techniques.

Another example is the purification of a fusion protein using a specific binding partner. Such purification methods are routine in the art. This is currently exemplified by the generation of a glutathione S-transferase fusion protein, expression in *E. coli*, and isolation to homogeneity using affinity chromatography on glutathione-agarose.

Although preferred for use in certain embodiments, there is no general requirement that the disclosed proteins or peptides always be provided in their most purified state. Indeed, it is contemplated that less substantially purified proteins or peptides, which are nonetheless enriched in, for example, CD40 ligand and/or CD40 agonist protein or peptide compositions, relative to the natural state, will have utility in certain embodiments. Methods exhibiting a lower degree of relative purification may have advantages in total recovery of protein product, or in maintaining the activity of an expressed protein. Inactive products also have utility in certain embodiments, such as, e.g., in antibody generation.

V. Expression Constructs and Recombinant Host Cells

Recombinant vectors are also contemplated for use in certain aspects of the present invention. Particularly useful vectors are contemplated to be those vectors in which the coding portion of a CD40 ligand and/or CD40 agonist DNA segment, whether encoding a full length protein or smaller peptide, is positioned under the control of a promoter. For expression in this manner, one would position the coding sequences adjacent to and under the control of the promoter. It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter.

The promoter may be in the form of the promoter that is naturally associated with a particular CD40 ligand and/or CD40 agonist gene, as may be obtained by isolating the 5' noncoding sequences located upstream of the coding segment, for example, using recombinant cloning and/or PCRT technology, in connection with the compositions disclosed herein. Direct amplification of nucleic acids using the PCRTM technology of U.S. Pat. Nos. 4,683,195 and 4,683,202 (herein incorporated by reference) are particularly contemplated to be useful in such methodologies.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a particular CD40 ligand and/or CD40 agonist gene in its natural environment. Such promoters may include promoters normally associated with other genes, and/or promoters isolated from any bacterial, viral, eukaryotic, or mammalian cell. Naturally, it will be important to employ a promoter that effectively directs the expression of the CD40 ligand and/or CD40 agonist DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides.

It will, of course, be understood that one or more than one genes encoding CD40 ligand and/or CD40 agonist proteins and/or or peptides may be used in the methods and compositions of the invention. The nucleic acid compositions and methods disclosed herein may entail the administration of one, two, three, or more, genes or gene segments. The maximum number of genes that may be used is limited only by practical considerations, such as the effort involved in simultaneously preparing a large number of gene constructs or even the possibility of eliciting a significant adverse cytotoxic effect.

In using multiple genes, they may be combined on a single genetic construct under control of one or more promoters, or they may be prepared as separate constructs of the same of different types. Thus, an almost endless combination of different genes and genetic constructs may be employed. Certain gene combinations may be designed to, or their use may otherwise result in, achieving synergistic effects on formation of an immune response, or the development of antibodies to gene products encoded by such nucleic acid segments, or in the production of treatment protocols for bone loss, and in particular, bone loss associated with estrogen depletion, aging and/or steroid therapy. Any and all such combinations are intended to fall within the scope of the present invention.

Prokaryotic expression of nucleic acid segments of the present invention may be performed using methods known to those of skill in the art, and will likely comprise expression vectors and promoter sequences such as those provided by tac, trp, lac, lacUV5 or T7. Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980).

When expression of the recombinant CD40 ligand and/or CD40 agonist proteins is desired in eukaryotic cells, a number of expression systems are available and known to those of skill in the art. For eukaryotic expression, preferred promoters include those such as CMV, RSV LTR, the SV40 promoter alone, and the SV40 promoter in combination with the SV40 enhancer. Another eukaryotic system contemplated for use in high-level expression is the Pichia expression vector system (Pharmacia LKB Biotechnology). Where eukaryotic expression is contemplated, one will also typically desire to incorporate into the transcriptional unit an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

In connection with expression embodiments to prepare recombinant CD40 ligand and/or CD40 agonist proteins and peptides, it is contemplated that longer DNA segments will most often be used, with DNA segments encoding the entire protein or functional domains, epitopes, ligand binding domains, subunits, etc. being most preferred. However, it will be appreciated that the use of shorter DNA segments to direct the expression of peptides or epitopic core regions, such as may be used to generate antibodies against a selected CD40, CD40 ligand and/or CD40 agonist proteins or peptides, also falls within the scope of the invention. DNA segments that encode peptide antigens from about 15 to about 100 amino acids in length, or more preferably, from about 15 to about 50 amino acids in length are contemplated to be particularly useful.

It is contemplated that virtually any recombinant host cell may be employed for expression of CD40 ligand and/or CD40 agonist gene(s), but certain advantages may be found in using a bacterial host cell such as *E. coli, S. typhimurium, B. subtilis*, or others. Examples of preferred prokaryotic hosts are *E. coli*, and in particular, *E. coli* strains ATCC69791, BL21(DE3), JM101, XL1-Blue™, RR1, LE392, B, X1776 (ATCC No. 31537), and W3110 (F⁻, λ⁻, prototrophic, ATCC273325). Alternatively, other Enterobacteriaceae species such as *Salmonella typhimurium* and *Serratia marcescens*, or even other Gram-negative hosts including various Pseudomonas species may be used in the recombinant expression of the genetic constructs disclosed herein.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* may be typically transformed using vectors such as pBR322, or any of its derivatives (Bolivar et al., 1977). pBR322 contains genes for ampicillin and tetracycline resistance and thus provides easy means for identifying transformed cells. pBR322, its derivatives, or other microbial plasmids or bacteriophage may also contain, or be modified to contain, promoters which can be used by the microbial organism for expression of endogenous proteins. Preferred vectors for cloning the CD40 ligand and/or CD40 agonist constructs, are pBlueScript™, and vectors based on the pET vector series (Novagen, Inc., Madison, Wis.; U.S. Pat. No. 4,952,496, incorporated herein by reference).

In addition, phage vectors containing replicon and control sequences that are compatible with the host microorganism can be used as transforming vectors in connection with these hosts. For example, bacteriophage such as λGEM™-11 may be utilized in making a recombinant vector that can be used to transform susceptible host cells such as *E. coli* LE392.

As used herein, the term "engineered" or "recombinant" cell is intended to refer to a cell into which a recombinant gene, such as a gene encoding a CD40 ligand and/or CD40 agonist protein or peptide, has been introduced. Therefore, engineered cells are distinguishable from naturally occurring cells that do not contain a recombinantly introduced gene. Engineered cells are thus cells having a gene or genes introduced through the hand of man. Recombinantly introduced genes will either be in the form of a single structural gene, an entire genomic clone comprising a structural gene and flanking DNA, or an operon or other functional nucleic acid segment which may also include genes positioned either upstream and/or downstream of the promoter, regulatory elements, or structural gene itself, or even genes not naturally associated with the particular structural gene of interest.

Expression in eukaryotic cells is also contemplated such as those derived from yeast, insect, or mammalian cell lines. *Saccharomyces cerevisiae*, or common bakers' yeast is the most commonly used among eukaryotic microorganisms, although a number of other species may also be employed for such eukaryotic expression systems. For expression in Saccharomyces, the plasmid YRp7, for example, is commonly used (Stinchcomb et al., 1979; Kingsman et al., 1979; Tschumper et al., 1980). This plasmid already contains the trp gene which provides a selection marker for a mutant strain of yeast lacking the ability to grow in tryptophan, for example ATCC No. 44076 or PEP4-1 (Jones, 1977). The presence of the trp lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts in the routine practice of the disclosed methods. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

These recombinant host cells may be employed in connection with "overexpressmg CD40 ligand and/or CD40 agonist proteins, that is, increasing the level of expression over that found naturally in mammalian cells. Many such vectors and host cells are readily available, one particular example of a suitable vector for expression in mammalian cells is that described in U.S. Pat. No. 5,168,050, incorporated herein by reference. However, there is no requirement that a highly purified vector be used, so long as the coding segment employed encodes a protein or peptide of interest, and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various regulatory sequences.

It is further contemplated that the CD40 ligand and/or CD40 agonist proteins or epitopic peptides derived from native or recombinant CD40 ligand and/or CD40 agonist proteins may be "overexpressed", i.e., expressed in increased levels relative to its natural expression, or even relative to the expression of other proteins in a recombinant host cell containing CD40 ligand and/or CD40 agonist protein-encoding DNA segments.

VI. Antibody Production

Also disclosed herein are methods of generating anti-CD40 antibodies. The methods generally involve administering to an animal a pharmaceutical composition comprising an immunologically effective amount of one or more CD40 protein and/or peptide compositions as disclosed herein. Preferred animals include mammals, and particularly humans. Other preferred animals include murines, bovines, equines, porcines, canines, felines and non-human primates.

Compositions for use in generating anti-CD40 antibodies may include partially or significantly purified CD40 protein and/or peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 10 amino acids and about 50 amino acids, between about amino acids and about 25 amino acids in length, or even between about 50 amino acids and about 100 amino acids in length will often be preferred. The antigenic proteins or peptides may also be combined with other agents, such as other CD40 peptide or nucleic acid compositions, if desired.

By "immunologically effective amount" is meant an amount of a CD40 protein or peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in prophylactic or therapeutic embodiments.

Nucleic acid sequences that encode CD40 proteins are useful in generating recombinant protein(s) for administration to a host. Such administration may be useful in the production of therapeutic antibodies. These methods of generating an immune response in an animal generally include administering to an animal, or human subject, a pharmaceutically-acceptable composition comprising an immunologically effective amount of a nucleic acid composition encoding a CD40 protein and/or peptide epitope.

Immunoformulations of this invention, whether intended for treatment or for the generation of antibodies, may comprise native, or synthetically-derived antigenic peptide fragments from these proteins. As such, antigenic functional equivalents of the proteins and peptides described herein also fall within the scope of the present invention. An "antigenically functional equivalent" protein or peptide is one that incorporates an epitope that is immunologically cross-reactive with one or more epitopes derived from any of the particular CD40 proteins disclosed. Antigenically functional equivalents, or epitopic sequences, may be first designed or predicted and then tested, or may simply be directly tested for cross-reactivity.

The identification or design of suitable epitopes, and/or their functional equivalents, suitable for use in immunoformulations, or simply as antigens, is a relatively straight-forward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The methods described in several other papers, and software programs based thereon, can also be used to identify epitopic core sequences. For example, Chou and Fasman (1974a, b; 1978; 1979); Jameson and Wolf (1988); Wolf et al. (1988); and Kyte and Doolittle (1982) all address this subject.

Another method for determining the major antigenic determinants of a polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. The antigenic determinants of the peptides that are initially identified can be further localized by performing subsequent syntheses of smaller peptides with larger overlaps, and by eventually replacing individual amino acids at each position along the immunoreactive peptide. The amino acid sequence of these "epitopic core sequences" may then be readily incorporated into peptides, either through the application of peptide synthesis or recombinant technology.

In other aspects of the present invention, administration of antibodies reactive with CD40 proteins to at-risk subjects will be effective for prophylaxis of, or therapy for, bone loss. Antibodies may be of several types, including those raised in heterologous donor animals or human volunteers immunized with CD40 proteins, monoclonal antibodies (mAbs) resulting from fusions of hybridomas derived from fusions of B cells from immunized animals or humans with compatible myeloma cell lines or so-called "humanized" mAbs resulting from expression of gene fusions of combinatorial determining regions of mAb-encoding genes from heterologous species with genes encoding human antibodies.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. Reference to antibodies throughout the specification includes whole polyclonal and monoclonal antibodies (mAbs), and parts thereof, either alone or conjugated with other moieties. Antibody parts include Fab', Fab, F(ab')$_2$, single domain antibodies (DABs), Fv, scFv (single chain Fv), and the like. The techniques for preparing and using various antibody-based constructs and fragments are well known in the art. The antibodies may be made in vivo in suitable laboratory animals or in vitro using recombinant DNA techniques. In a preferred embodiment, an antibody is a polyclonal antibody.

Means for preparing and characterizing antibodies are well known in the art (See, e.g., Harlow and Lane (1988); incorporated herein by reference). Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Methods for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions. Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC=iantigens may even be used. Exemplary, often preferred adjuvants include complete Freund's adjuvant (a non-specific stimulator of the immune response containing killed *Mycobacterium tuberculosis*), incomplete Freund's adjuvants and aluminum adjuvants.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, N.J.) and cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intranasal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified CD40, CD40 ligand and/or CD40 agonist protein, polypeptide, peptide or domain. The immunizing composition is administered in a manner effective to stimulate antibody producing cells. The methods for generating monoclonal antibodies (MAbs) generally begin along the same lines as those for preparing polyclonal antibodies. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions. The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986, pp. 65–66; Campbell, 1984, pp. 75–83). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically-induced fusion methods is also appropriate (Goding, 1986, pp. 71–74).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like. The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods that include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. Alternatively, monoclonal antibody fragments encompassed by the present invention can be synthesized using an automated peptide synthesizer, or by expression of full-length gene or of gene fragments in *E. coli*.

A. Antibody Fragments

Irrespective of the source of the original anti-CD40 antibody, either the intact antibody, antibody multimers, or any one of a variety of functional, antigen-binding regions of the antibody may be used in the present invention. Exemplary functional regions include scFv, Fv, Fab', Fab and F(ab')$_2$ fragments of the anti-CD40 antibodies. Techniques for preparing such constructs are well known to those in the art and are further exemplified herein.

The choice of antibody construct may be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Fab fragments can be obtained by proteolysis of the whole immunoglobulin by the non-specific thiol protease, papain. Papain must first be activated by reducing the sulphydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

The usual procedure for preparation of F(ab')$_2$ fragments from IgG of rabbit and human origin is limited proteolysis by the enzyme pepsin. The conditions, 100×antibody excess w/w in acetate buffer at pH 4.5, 37° C., suggest that antibody is cleaved at the C-terminal side of the inter-heavy-chain disulfide bond. Rates of digestion of mouse IgG may vary with subclass and it may be difficult to obtain high yields of active F(ab')$_2$ fragments without some undigested or completely degraded IgG. In particular, IgG$_{2b}$ is highly susceptible to complete degradation. The other subclasses require different incubation conditions to produce optimal results, all of which is known in the art.

Digestion of rat IgG by pepsin requires conditions including dialysis in 0.1 M acetate buffer, pH 4.5, and then incubation for four hours with 1% w/w pepsin; IgG$_1$ and IgG$_{2a}$ digestion is improved if first dialyzed against 0.1 M formate buffer, pH 2.8, at 4° C., for 16 hours followed by acetate buffer. IgG$_{2b}$ gives more consistent results with incubation in staphylococcal V8 protease (3% w/w) in 0.1 M sodium phosphate buffer, pH 7.8, for four hours at 37° C.

U.S. Pat. Nos. 5,855,866 and 5,877,289 are specifically incorporated herein by reference for the purposes of even further supplementing the present teachings regarding the preparation and use of functional, antigen-binding regions of antibodies, including scFv, Fv, Fab', Fab and F(ab')$_2$ fragments of the anti-CD40 antibodies.

B. Anti-CD40 Antibodies from Phagemid Libraries

Recombinant technology now allows the preparation of antibodies having the desired specificity from recombinant genes encoding a range of antibodies (Van Dijk et al., 1989). Certain recombinant techniques involve the isolation of the antibody genes by immunological screening of combinatorial immunoglobulin phage expression libraries prepared from RNA isolated from the spleen of an immunized animal (Morrison et al., 1986; Winter and Milstein, 1991).

For such methods, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989). Production of antibodies using the lambda vector involves the cloning of heavy and light chain populations of DNA sequences into separate starting vectors. The vectors are subsequently combined randomly to form a single vector that directs the co-expression of heavy and light chains to form antibody fragments. The heavy and light chain DNA sequences are obtained by amplification, preferably by PCR™ or a related amplification technique, of mRNA isolated from spleen cells (or hybridomas thereof) from an animal that has been immunized with a selected antigen. The heavy and light chain sequences are typically amplified using primers that incorporate restriction sites into the ends of the amplified DNA segment to facilitate cloning of the heavy and light chain segments into the starting vectors.

Another method for the generation and screening of large libraries of wholly or partially synthetic antibody combining sites, or paratopes, utilizes display vectors derived from filamentous phage such as M13, fl or fd. These filamentous phage display vectors, referred to as "phagemids", yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., 1991; Barbas et al., 1991).

This general technique for filamentous phage display is described in U.S. Pat. No. 5,658,727, incorporated herein by reference. In a most general sense, the method provides a system for the simultaneous cloning and screening of preselected ligand-binding specificities from antibody gene repertoires using a single vector system. Screening of isolated members of the library for a pre-selected ligand-binding capacity allows the correlation of the binding capacity of an expressed antibody molecule with a convenient means to isolate the gene that encodes the member from the library.

Linkage of expression and screening is accomplished by the combination of targeting of a fusion polypeptide into the periplasm of a bacterial cell to allow assembly of a functional antibody, and the targeting of a fusion polypeptide onto the coat of a filamentous phage particle during phage assembly to allow for convenient screening of the library member of interest. Periplasmic targeting is provided by the presence of a secretion signal domain in a fusion polypeptide. Targeting to a phage particle is provided by the presence of a filamentous phage coat protein membrane anchor domain (i.e., a cpIII- or cpVIII-derived membrane anchor domain) in a fusion polypeptide.

The diversity of a filamentous phage-based combinatorial antibody library can be increased by shuffling of the heavy and light chain genes, by altering one or more of the complementarity determining regions of the cloned heavy chain genes of the library, or by introducing random mutations into the library by error-prone polymerase chain reactions. Additional methods for screening phagemid libraries are described in U.S. Pat. Nos. 5,580,717; 5,427,908; 5,403,484; and 5,223,409, each incorporated herein by reference.

Another method for the screening of large combinatorial antibody libraries has been developed, utilizing expression of populations of diverse heavy and light chain sequences on the surface of a filamentous bacteriophage, such as M13, fl or fd (U.S. Pat. No. 5,698,426; incorporated herein by reference). Two populations of diverse heavy (Hc) and light (Lc) chain sequences are synthesized by polymerase chain reaction (PCR™). These populations are cloned into separate M13-based vector containing elements necessary for expression. The heavy chain vector contains a gene VIII (gVIII) coat protein sequence so that translation of the heavy chain sequences produces gVIII-Hc fusion proteins. The populations of two vectors are randomly combined such that only the vector portions containing the Hc and Lc sequences are joined into a single circular vector.

The combined vector directs the co-expression of both Hc and Lc sequences for assembly of the two polypeptides and surface expression on M13 (U.S. Pat. No. 5,698,426). The combining step randomly brings together different Hc and Lc encoding sequences within two diverse populations into a single vector. The vector sequences donated from each independent vector are necessary for production of viable phage. Also, since the pseudo gVIII sequences are contained in only one of the two starting vectors, co-expression of functional antibody fragments as Lc associated gVIII-Hc fusion proteins cannot be accomplished on the phage surface until the vector sequences are linked in the single vector.

Surface expression of the antibody library is performed in an amber suppressor strain. An amber stop codon between the Hc sequence and the gVIII sequence unlinks the two components in a non-suppressor strain. Isolating the phage produced from the non-suppressor strain and infecting a suppressor strain will link the Hc sequences to the gVIII sequence during expression. Culturing the suppressor strain after infection allows the coexpression on the surface of M13 of all antibody species within the library as gVIII fusion proteins (gVIII-Fab fusion proteins). Alternatively, the DNA can be isolated from the non-suppressor strain and then introduced into a suppressor strain to accomplish the same effect.

The surface expression library is screened for specific Fab fragments that bind preselected molecules by standard affinity isolation procedures. Such methods include, for example, panning (Parmley and Smith, 1988), affinity chromatography and solid phase blotting procedures. Panning is preferred, because high titers of phage can be screened easily, quickly and in small volumes. Furthermore, this procedure can select minor Fab fragments species within the population, which otherwise would have been undetectable, and amplified to substantially homogenous populations. The selected Fab fragments can be characterized by sequencing the nucleic acids encoding the polypeptides after amplification of the phage population.

Another method for producing diverse libraries of antibodies and screening for desirable binding specificities is described in U.S. Pat. Nos. 5,667,988 and 5,759,817, each incorporated herein by reference. The method involves the preparation of libraries of heterodimeric immunoglobulin molecules in the form of phagemid libraries using degenerate oligonucleotides and primer extension reactions to incorporate the degeneracies into the CDR regions of the immunoglobulin variable heavy and light chain variable domains, and display of the mutagenized polypeptides on the surface of the phagemid. Thereafter, the display protein is screened for the ability to bind to a preselected antigen.

The method for producing a heterodimeric immunoglobulin molecule generally involves (1) introducing a heavy or light chain V region-coding gene of interest into the phagemid display vector; (2) introducing a randomized binding site into the phagemid display protein vector by primer extension with an oligonucleotide containing regions of homology to a CDR of the antibody V region gene and containing regions of degeneracy for producing randomized coding sequences to form a large population of display vectors each capable of expressing different putative binding sites displayed on a phagemid surface display protein; (3) expressing the display protein and binding site on the surface of a filamentous phage particle; and (4) isolating (screening) the surface-expressed phage particle using affinity techniques such as panning of phage particles against a preselected antigen, thereby isolating one or more species of phagemid containing a display protein containing a binding site that binds a preselected antigen.

A further variation of this method for producing diverse libraries of antibodies and screening for desirable binding specificities is described in U.S. Pat. No. 5,702,892, incorporated herein by reference. In this method, only heavy chain sequences are employed, the heavy chain sequences are randomized at all nucleotide positions which encode either the CDRI or CDRIII hypervariable region, and the genetic variability in the CDRs is generated independent of any biological process.

In the method, two libraries are engineered to genetically shuffle oligonucleotide motifs within the framework of the heavy chain gene structure. Through random mutation of either CDRI or CDRIII, the hypervariable regions of the heavy chain gene were reconstructed to result in a collection of highly diverse sequences. The heavy chain proteins encoded by the collection of mutated gene sequences possessed the potential to have all of the binding characteristics of an immunoglobulin while requiring only one of the two immunoglobulin chains.

Specifically, the method is practiced in the absence of the immunoglobulin light chain protein. A library of phage displaying modified heavy chain proteins is incubated with an immobilized ligand to select clones encoding recombinant proteins that specifically bind the immobilized ligand. The bound phage are then dissociated from the immobilized ligand and amplified by growth in bacterial host cells. Individual viral plaques, each expressing a different recombinant protein, are expanded, and individual clones can then be assayed for binding activity.

C. Anti-CD40 Antibodies from Human Lymphocytes

In vitro immunization, or antigen stimulation, may also be used to generate a human anti-CD40 antibody. Such "in vitro immunization" involves antigen-specific activation of non-immunized B lymphocytes, generally within a mixed population of lymphocytes (mixed lymphocyte cultures, MLC). In vitro immunizations may also be supported by B cell growth and differentiation factors and lymphokines. The antibodies produced by these methods are often IgM antibodies (Borrebaeck and Moller, 1986).

Another method has been described (U.S. Pat. No. 5,681,729, incorporated herein by reference) wherein human lymphocytes that mainly produce IgG (or IgA) antibodies can be obtained. The method involves, in a general sense, transplanting human lymphocytes to an immunodeficient animal so that the human lymphocytes "take" in the animal body; immunizing the animal with a desired antigen, so as to generate human lymphocytes producing an antibody specific to the antigen; and recovering the human lymphocytes producing the antibody from the animal. The human lymphocytes thus produced can be used to produce a monoclonal antibody by immortalizing the human lymphocytes producing the antibody, cloning the obtained immortalized human-originated lymphocytes producing the antibody, and recovering a monoclonal antibody specific to the desired antigen from the cloned immortalized human-originated lymphocytes.

The immunodeficient animals that may be employed in this technique are those that do not exhibit rejection when human lymphocytes are transplanted to the animals. Such animals may be artificially prepared by physical, chemical or biological treatments. Any immunodeficient animal may be employed. The human lymphocytes may be obtained from human peripheral blood, spleen, lymph nodes, tonsils or the like.

The "taking" of the transplanted human lymphocytes in the animals can be attained by merely administering the human lymphocytes to the animals. The administration route is not restricted and may be, for example, subcutaneous, intravenous or intraperitoneal. The dose of the human lymphocytes is not restricted, and can usually be $10^6$ to $10^8$ lymphocytes per animal. The immunodeficient animal is then immunized with the desired CD40 antigen.

After the immunization, human lymphocytes are recovered from the blood, spleen, lymph nodes or other lymphatic tissues by any conventional method. For example, mononuclear cells can be separated by the Ficoll-Hypaque (specific gravity: 1.077) centrifugation method, and the monocytes removed by the plastic dish adsorption method. The contaminating cells originating from the immunodeficient animal may be removed by using an antiserum specific to the animal cells. The antiserum may be obtained by, for example, immunizing a second, distinct animal with the spleen cells of the immunodeficient animal, and recovering serum from the distinct immunized animal. The treatment with the antiserum may be carried out at any stage. The human lymphocytes may also be recovered by an immunological method employing a human immunoglobulin expressed on the cell surface as a marker.

By these methods, human lymphocytes mainly producing IgG and IgA antibodies specific to CD40 can be obtained. Monoclonal antibodies are then obtained from the human lymphocytes by immortalization, selection, cell growth and antibody production.

D. Transgenic Mice Containing Human Antibody Libraries

Recombinant technology is now available for the preparation of anti-CD40 antibodies. In addition to the combinatorial immunoglobulin phage expression libraries disclosed above, another molecular cloning approach is to prepare antibodies from transgenic mice containing human antibody libraries. Such techniques are described in U.S. Pat. No. 5,545,807, incorporated herein by reference.

In a most general sense, these methods involve the production of a transgenic animal that has inserted into its germline genetic material that encodes for at least part of an immunoglobulin of human origin or that can rearrange to encode a repertoire of immunoglobulins. The inserted genetic material may be produced from a human source, or may be produced synthetically. The material may code for at least part of a known immunoglobulin or may be modified to code for at least part of an altered immunoglobulin.

The inserted genetic material is expressed in the transgenic animal, resulting in production of an immunoglobulin derived at least in part from the inserted human immunoglobulin genetic material. It is found the genetic material is rearranged in the transgenic animal, so that a repertoire of immunoglobulins with part or parts derived from inserted genetic material may be produced, even if the inserted genetic material is incorporated in the germline in the wrong position or with the wrong geometry.

The inserted genetic material may be in the form of DNA cloned into prokaryotic vectors such as plasmids and/or cosmids. Larger DNA fragments are inserted using yeast artificial chromosome vectors (Burke et al., 1987), or by introduction of chromosome fragments (Richer and Lo, 1989). The inserted genetic material may be introduced to the host in conventional manner, for example by injection or other procedures into fertilized eggs or embryonic stem cells.

In preferred aspects, a host animal that initially does not carry genetic material encoding immunoglobulin constant regions is utilized, so that the resulting transgenic animal will use only the inserted human genetic material when producing immunoglobulins. This can be achieved either by using a naturally occurring mutant host lacking the relevant genetic material, or by artificially making mutants e.g., in cell lines ultimately to create a host from which the relevant genetic material has been removed.

Where the host animal carries genetic material encoding immunoglobulin constant regions, the transgenic animal will carry the naturally occurring genetic material and the inserted genetic material and will produce immunoglobulins derived from the naturally occurring genetic material, the inserted genetic material, and mixtures of both types of genetic material. In this case the desired immunoglobulin can be obtained by screening hybridomas derived from the transgenic animal, e.g., by exploiting the phenomenon of allelic exclusion of antibody gene expression or differential chromosome loss.

Once a suitable transgenic animal has been prepared, the animal is simply immunized with the desired immunogen. Depending on the nature of the inserted material, the animal may produce a chimeric immunoglobulin, e.g. of mixed mouse/human origin, where the genetic material of foreign origin encodes only part of the immunoglobulin; or the animal may produce an entirely foreign immunoglobulin, e.g. of wholly human origin, where the genetic material of foreign origin encodes an entire immunoglobulin.

Polyclonal antisera may be produced from the transgenic animal following immunization. Immunoglobulin-producing cells may be removed from the animal to produce the immunoglobulin of interest. Preferably, monoclonal antibodies are produced from the transgenic animal, e.g., by fusing spleen cells from the animal with myeloma cells and screening the resulting hybridomas to select those producing the desired antibody. Suitable techniques for such processes are described herein.

In an alternative approach, the genetic material may be incorporated in the animal in such a way that the desired antibody is produced in body fluids such as serum or external secretions of the animal, such as milk, colostrum or saliva. For example, by inserting in vitro genetic material encoding for at least part of a human immunoglobulin into a gene of a mammal coding for a milk protein and then introducing the gene to a fertilized egg of the mammal, e.g., by injection, the egg may develop into an adult female mammal producing milk containing immunoglobulin derived at least in part from the inserted human immunoglobulin genetic material. The desired antibody can then be harvested from the milk. Suitable techniques for carrying out such processes are known to those skilled in the art.

The foregoing transgenic animals are usually employed to produce human antibodies of a single isotype, more specifically an isotype that is essential for B cell maturation, such as IgM and possibly IgD. Another preferred method for producing human anti-CD40 antibodies is described in U.S. Pat. Nos. 5,545,806; 5,569,825; 5,625,126; 5,633,425; 5,661,016; and 5,770,429; each incorporated by reference, wherein transgenic animals are described that are capable of switching from an isotype needed for B cell development to other isotypes.

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain. The use of mu or delta constant regions is largely determined by alternate splicing, permitting IgM and IgD to be coexpressed in a single cell. The other heavy chain isotypes (gamma, alpha, and epsilon) are only expressed natively after a gene rearrangement event deletes the C mu and C delta exons. This gene rearrangement process, termed isotype switching, typically occurs by recombination between so called switch segments located immediately upstream of each heavy chain gene (except delta). The individual switch segments are between 2 and 10 kb in length, and consist primarily of short repeated sequences.

For these reasons, it is preferable that transgenes incorporate transcriptional regulatory sequences within about 1–2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. Although a 5' flanking sequence from one switch region can be operably linked to a different switch region for transgene construction, in some embodiments it is preferred that each switch region incorporated in the transgene construct have the 5' flanking region that occurs immediately upstream in the naturally occurring germline configuration. Sequence information relating to immunoglobulin switch region sequences is known (Mills et al., 1990; Sideras et al., 1989).

In the method described in U.S. Pat. Nos. 5,545,806; 5,569,825; 5,625,126; 5,633,425; 5,661,016; and 5,770,429, the human immunoglobulin transgenes contained within the transgenic animal function correctly throughout the pathway of B-cell development, leading to isotype switching. Accordingly, in this method, these transgenes are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encodes the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus consists of approximately 200 V gene segments spanning 2 Mb, approximately 30 D gene segments spanning about 40 kb, six j segments clustered within a 3 kb span, and nine constant region gene segments spread out over approximately 300 kb. The entire locus spans approximately 2.5 Mb of the distal portion of the long arm of chromosome 14. Heavy chain transgene fragments containing members of all six of the known $V_H$ families, the D and J gene segments, as well as the mu, delta, ganma 3, gamma 1 and alpha 1 constant regions are known (Berman et al., 1988). Genomic fragments containing all of the necessary gene segments and regulatory sequences from a human light chain locus is similarly constructed.

The expression of successfully rearranged immunoglobulin heavy and light transgenes usually has a dominant effect by suppressing the rearrangement of the endogenous immunoglobulin genes in the transgenic nonhuman animal. However, in certain embodiments, it is desirable to effect complete inactivation of the endogenous Ig loci so that hybrid immunoglobulin chains comprising a human variable region and a non-human (e.g., murine) constant region cannot be formed, for example by trans-switching between the transgene and endogenous Ig sequences. Using embryonic stem cell technology and homologous recombination, the endogenous immunoglobulin repertoire can be readily eliminated. In addition, suppression of endogenous Ig genes may be accomplished using a variety of techniques, such as antisense technology.

In other aspects of the invention, it may be desirable to produce a trans-switched immunoglobulin. Antibodies comprising such chimeric trans-switched immunoglobulins can be used for a variety of applications where it is desirable to have a non-human (e.g., murine) constant region, e.g., for retention of effector functions in the host. The presence of a murine constant region can afford advantages over a human constant region, for example, to provide murine effector functions (e.g., ADCC, murine complement fixation) so that such a chimeric antibody may be tested in a mouse disease model. Subsequent to the animal testing, the human variable region encoding sequence may be isolated, e.g., by PCR amplification or cDNA cloning from the source (hybridoma clone), and spliced to a sequence encoding a desired human constant region to encode a human sequence antibody more suitable for human therapeutic use.

E. Humanized Anti-CD40 Antibodies

Human antibodies generally have at least three potential advantages for use in human therapy. First, because the effector portion is human, it may interact better with the other parts of the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, the half-life in the human circulation will be similar to naturally occurring human antibodies, allowing smaller and less frequent doses to be given.

Various methods for preparing human anti-CD40 antibodies are provided herein. In addition to human antibodies, "humanized" antibodies have many advantages. "Humanized" antibodies are generally chimeric or mutant monoclonal antibodies from mouse, rat, hamster, rabbit or other species, bearing human constant and/or variable region domains or specific changes. Techniques for generating a so-called "humanized" anti-CD40 antibody are well known to those of skill in the art.

Humanized antibodies also share the foregoing advantages. First, the effector portion is still human. Second, the human immune system should not recognize the framework or constant region as foreign, and therefore the antibody response against such an injected antibody should be less than against a totally foreign mouse antibody. Third, injected humanized antibodies, as opposed to injected mouse antibodies, will presumably have a half-life more similar to naturally occurring human antibodies, also allowing smaller and less frequent doses.

A number of methods have been described to produce humanized antibodies. Controlled rearrangement of antibody domains joined through protein disulfide bonds to form new, artificial protein molecules or "chimeric" antibodies can be utilized (Konieczny et al., 1981). Recombinant DNA technology can also be used to construct gene fusions between DNA sequences encoding mouse antibody variable light and heavy chain domains and human antibody light and heavy chain constant domains (Morrison et al., 1984).

DNA sequences encoding the antigen binding portions or complementarity determining regions (CDR's) of murine monoclonal antibodies can be grafted by molecular means into the DNA sequences encoding the frameworks of human antibody heavy and light chains (Jones et al., 1986; Riechmann et al., 1988). The expressed recombinant products are called "reshaped" or humanized antibodies, and comprise the framework of a human antibody light or heavy chain and the antigen recognition portions, CDR's, of a murine monoclonal antibody.

Another method for producing humanized antibodies is described in U.S. Pat. No. 5,639,641, incorporated herein by reference. The method provides, via resurfacing, humanized rodent antibodies that have improved therapeutic efficacy due to the presentation of a human surface in the variable region. In the method: (1) position alignments of a pool of antibody heavy and light chain variable regions is generated to give a set of heavy and light chain variable region framework surface exposed positions, wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity determining regions of the rodent antibody; and (5) the humanized rodent antibody having binding specificity is produced.

A similar method for the production of humanized antibodies is described in U.S. Pat. Nos. 5,693,762; 5,693,761; 5,585,089; and 5,530,101, each incorporated herein by reference. These methods involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to the CDR's, amino acids from the donor immunoglobulin framework that are capable of interacting with the CDR's to effect binding affinity, such as one or more amino acids that are immediately adjacent to a CDR in the donor immunoglobulin or those within about 3 Å as predicted by molecular modeling. The heavy and light chains may each be designed by using any one, any combination, or all of the various position criteria described in U.S. Pat. Nos. 5,693,762; 5,693,761; 5,585,089; and 5,530,101. When combined into an intact antibody, the humanized immunoglobulins are substantially non-immunogenic in humans and retain substantially the same affinity as the donor immunoglobulin to the original antigen.

An additional method for producing humanized antibodies is described in U.S. Pat. Nos. 5,565,332 and 5,733,743, each incorporated herein by reference. This method combines the concept of humanizing antibodies with the phagemid libraries also described in detail herein. In a general sense, the method utilizes sequences from the antigen binding site of an antibody or population of antibodies directed against an antigen of interest. Thus for a single rodent antibody, sequences comprising part of the antigen binding site of the antibody may be combined with diverse repertoires of sequences of human antibodies that can, in combination, create a complete antigen binding site.

The antigen binding sites created by this process differ from those created by CDR grafting, in that only the portion of sequence of the original rodent antibody is likely to make contacts with antigen in a similar manner. The selected human sequences are likely to differ in sequence and make alternative contacts with the antigen from those of the original binding site. However, the constraints imposed by binding of the portion of original sequence to antigen and the shapes of the antigen and its antigen binding sites, are likely to drive the new contacts of the human sequences to the same region or epitope of the antigen. This process has therefore been termed "epitope imprinted selection" (EIS).

Starting with an animal antibody, one process results in the selection of antibodies that are partly human antibodies. Such antibodies may be sufficiently similar in sequence to human antibodies to be used directly in therapy or after alteration of a few key residues. Sequence differences between the rodent component of the selected antibody with human sequences could be minimized by replacing those residues that differ with the residues of human sequences, for example, by site directed mutagenesis of individual residues, or by CDR grafting of entire loops. However, antibodies with entirely human sequences can also be created. EIS therefore offers a method for making partly human or entirely human antibodies that bind to the same epitope as animal or partly human antibodies respectively. In EIS, repertoires of antibody fragments can be displayed on the surface of filamentous phase and the genes encoding fragments with antigen binding activities selected by binding of the phage to antigen.

Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, each incorporated herein by reference.

VII. Biological Functional Equivalents

As discussed above, modification and changes may be made in the structure of the proteins, polypeptides and peptides for use in the present invention and the DNA segments that encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to Table 3.

For example, certain amino acids may be substituted for other amino acids in a protein structure without appreciable loss of interactive binding capacity with structures such as, for example, the CD40 receptor or antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the protein or peptide sequences of the disclosed compositions, or corresponding DNA sequences which encode said proteins or peptides, without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5);leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

VIII. Mutagenesis

Site-specific mutagenesis is a technique useful in the preparation of individual peptides, or biologically functional equivalent proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to about 10 residues on both sides of the junction of the sequence being altered.

In general, the technique of site-specific mutagenesis is well known in the art, as exemplified by various publications. As will be appreciated, the technique typically employs a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis, which eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylarnine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

The PCR™-based strand overlap extension (SOE) (Ho et al., 1989) for site-directed mutagenesis is particularly preferred for site-directed mutagenesis of the nucleic acid compositions of the present invention. The techniques of PCR™ are well-known to those of skill in the art, as described hereinabove. The SOE procedure involves a two-step PCR™ protocol, in which a complementary pair of internal primers (B and C) is used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into E. coli JM101, XL1-Blue™ (Stratagene, LaJolla, Calif.), JM105, or TG1 (Carter et al., 1985) cells. Clones are isolated and the mutations are confirmed by sequencing of the isolated plasmids.

IX. Combination With Other Agents

In certain embodiments of the present invention, the CD40 ligand and/or CD40 agonist compositions are administered in combination with other biological and/or therapeutic agents, including, but not limited to, other agents that reduce or prevent cell death/apoptosis, and/or agents such as selective estrogen receptor modulators, or other compounds that are useful in the treatment or prevention of osteoporosis.

1. Anti-Apoptosis Agents

Exemplary anti-cell death/anti-apoptosis compounds contemplated for use in combination with the CD40 ligands and/or agonists disclosed herein include transforming growth factor beta, IL-6 (Jilka et al., 1998), bisphosphonates and estrogen (Weinstein et al., 1998; Hughes et al., 1996; Tomkinson et al., 1998; Noble et al., 1997). As estrogen is thought to promote apoptosis of osteoclasts, and inhibit apoptosis of osteoblasts, it is particularly preferred for use in conjunction with the CD40 ligand and/or agonist compositions disclosed herein.

Other exemplary anti-cell death/anti-apoptosis genes and constructs are listed herein in Table 4. Any one or more of the genes listed therein may be used in the combination with the CD40 ligand and/or CD40 agonist compositions disclosed herein. It will be understood that the genes listed in Table 4 are only exemplary of the types of the anti-cell death/anti-apoptosis genetic constructs and elements that may be used in this invention. Further anti-cell death/anti-apoptosis genes and constructs will be known to those of ordinary skill in the art.

TABLE 4

Exemplary Anti-Cell Death/Anti-Apoptosis Agents

| AGENTS | MODE OF ACTION |
|---|---|
| tyrosine kinases, both membrane-associated and cytoplasmic forms, such as Src family, Jak/Stats, Ros, Neu (also known as her2 or erbB-2; GenBank accession numbers M11730, X03363, U02326 and S57296), Fms, Ret, abl, Met serine/threonine kinases: Mos, Raf, protein kinase C, PIM-1 growth factor and receptors: platelet derived growth factor (PDGF), insulin-like growth factor (IGF-1; GeriBank accession number X04434 and M24599), insulin receptor substrate (IRS-1 | perturb signal transduction |

TABLE 4-continued

Exemplary Anti-Cell Death/Anti-Apoptosis Agents

| AGENTS | MODE OF ACTION |
| --- | --- |
| (GenBank accession number S62539) and IRS-2 (Genbank accession number AB000732)), Erb family, epidermal growth factor (EGF), growth hormone, hepatocyte growth factor (HGF; GenBank accession number U11813) basic fibroblast growth factor (bFGF) | |
| small GTPases (G) proteins including the ras family, rab family, and $Gs_\alpha$ (GenBank accession numbers X56009, X04409) receptor-type tyrosine phosphatase IA-2 | |
| cyclin-dependent protein kinases (cdk), classes A–E; members of the cyclin family such as cyclin D (GenBank accession numbers M64349 and M73554) | affect cell cycle |
| Myc family members including c-myc (GenBank accession numbers J00120, K01980, M23541, V00501, X00364), N-myc, and L-myc; Rel family members including NF-kappaB; c-Myb, Ap-1, fos, jun, insulinoma associated cDNA (IA-1), ErbB-1, PAX gene family | alter nuclear transcription |
| telomerase (human TERT GenBank accession numbers: AF018176 and AF015950) | lengthens telomeres of chromosomes |
| bcl-2 (GenBank accession numbers M14745, X06487) and family members including Bcl-x1, Mcl-1, Bak, A1, A20 inhibitors of interleukin-1b-converting enzyme and family members | inhibit apoptosis |
| viral proteins such as SV40 large T antigen (GenBank accession number J02400) and polyoma large T antigen, SV40 temperature sensitive large T antigen, adenovirus E1A and E1B, human papilomavirus E6 (GenBank accession numbers X67160, A06328, V01116, X03321) and E7 (GenBank accession numbers A06328, V01116, X03321) | pleiotropic activities |
| mutant tumor suppressor genes or proteins, including p53 (ovarian (GenBank accession numbers S53545, S62213, S62216); liver (GenBank accession numbers S62711, S62713, S62714, S67715, S72716); gastric (GenBank accession numbers S63157); colon (GenBank accession numbers S63610); bladder (GenBank accession numbers S85568, S85570, S85691); lung (GenBank accession numbers S41969, S41977); and glioma (GenBank accession numbers S85807, S85712, S85713)), retinoblastoma gene (Rb), Wilm's tumor (WT1), bax alpha, interleukin-1b-converting enzyme and family, MEN-1 gene (chromosome 11q13; GenBank accession number U93236), neurofibromatosis, type 1 (NF1), cdk inhibitor p16, colorectal cancer gene (DCC), familial adenomatosis polyposis gene (FAP), multiple tumor suppressor gene (MTS-1), BRCA1, and BRCA2 | failure to promote apoptosis |

2. Anti-Osteoporosis Agents

The use of antiestrogens, such as tamoxifen, as adjuvant chemotherapy for breast cancer in menopausal women and as prophylactic treatment for women at high risk for breast cancer, is associated with improved lipid profiles and increased bone density (Love et al., 1992). These unexpected beneficial effects suggest that certain estrogen analogs such as tamoxifen may function as weak estrogen agonists in specific tissues such as bone, liver, and endometrium. These differences in estrogen activity may be explained in part by the recent discovery of a second type of estrogen receptor, the estrogen beta receptor. Clinical trials are being conducted with other estrogen analogs (now called selective estrogen receptor modulators or SERMs) such as raloxifene to assess their use as an alternative to traditional estrogen replacement therapy.

Raloxifene has been approved by the Food and Drug Administration for the prevention of postmenopausal osteoporosis. A daily dose of 60 mg of raloxifene is currently recommended for osteoporosis prevention. In a prospective randomized multicenter trial of over 600 menopausal women, raloxifene was shown to effectively protect against bone loss and reduce LDL cholesterol levels without inducing endometrial proliferation (Delmas et al., 1997). In contrast to oral estrogens, levels of HDL cholesterol and triglycerides were unchanged during treatment. In this study, there were no significant differences in the proportions of women reporting hot flashes between the group receiving 60 mg of raloxifene daily and those taking placebo (26.3% and 22.7%). Thus, raloxifene would probably not be used in early menopausal women who are more likely to have hot flashes and other hypoestrogenic symptomatology.

Other compounds that have been reported to be effective in preventing bone loss include alendronate, calcium, sodium fluoride (Kleerekoper and Mendlovic, 1993), vitamin D and intranasal use of calcitonin (Reginster et al., 1995).

In addition, estrogen replacement therapy (ERT)/hormone replacement therapy (HRT) and several bisphosphonates are currently approved for the treatment of osteoporosis or are undergoing investigation. The bisphosphonates inhibit resorption and produce an average 6% increase in spinal bone mineral density (Ott, 1993; Pacifici et al., 1988; Chestnut et al., 1995; Rossini et al., 1994). In a prevention trial that compared placebo, 5 mg alendronate, and estrogen (CEE 0.625 mg/day and progestin [MPA] 5 mg/day), women treated with alendronate had a mean increase of 3.5% at the spine and 1.9% at the hip (Hosking et al., 1998). Responses to HRT were 1 to 2 percentage points greater than alendronate. Those who received placebo lost bone mineral density. In a study of approximately 2,000 women randomized to either placebo or alendronate, it was found that significantly fewer women in the alendronate group had vertebra fractures (Black et al., 1996).

X. Apoptosis Assays

Many events occur during the process of apoptosis that can be assayed to determine if cells are undergoing apoptosis and/or the extent of apoptosis. Nuclear matrix proteins (NMP) have been shown to dissociate and solubilize during apoptosis, which likely accounts for certain morphological changes seen in the nucleus of an apoptotic cell. The amount of soluble NMP is a function of cell death, and can be quantitated by detection of soluble NMP (Miller et al., 1993). Additionally, during cell death lamins within the nuclear envelope become substrates for proteases, contributing to the changes seen in cellular morphology (Takahashi et al., 1996). This loss of lamins from the nuclear envelope can be detected by anti-lamin antibodies.

An early event in apoptosis is the collapse of chromatin against the nuclear periphery. Further condensation can lead to many discrete balls of chromatin each surrounded by a nuclear envelope (Earnshaw, 1995). This disruption of the nucleus leads to the degradation of the DNA by endogenous endonucleases. Due to the association of the DNA with the histone proteins to form nucleosomes, the degradation of the DNA produces 180 to 200 bp fragments that can be visualized as a DNA ladder by agarose or acrylamide gel electrophoresis (Bortner et al., 1995). These nucleosomal fragments can also be labeled radioactively, flourescently, or with enzymes that can catalyze a color producing reaction. The fragments that possess free 3' hydroxyl groups (Gavrieli et al., 1992) can be labeled using terminal deoxynucleotidyl transferase, and those lacking the ternminal 3' hydroxyl group can be labeled using the Klenow fragment of $E. coli$ DNA polymerase I.

In addition to nuclear changes, plasma and mitochondrial membrane perturbations occur early in apoptosis. Phosphatidylserine, which is restricted to the inner surface of the plasma membrane bilayer in normal cells, is externalized to the outer plasma membrane where it is recognized and eliminated by macrophages (Fadok et al., 1992). Phosphatidylserine on the outer surface of the plasma membrane can be detected by annexin, which has a high affinity for phosphatidylserine (Martin et al., 1995), or by anti-phosphatidylserine antibodies. Furthermore, certain dyes that are excluded from viable cells, such as trypan blue and propidium iodide, stain apoptotic cells due to these membrane perturbations.

Other assays detect perturbations in the plasma membrane, such as assaying for the release of the cytosolic enzyme lactate dehydrogenase (Wroblewski and LaDue, 1955), or in mitochondrial function, such as the MTT ([3-(4,5-dimethylthiazol-2-yl)2,5-diphenyltetrazolium bromide]) assay, which measures the ability of mitochondria to convert MTT into a colored formazan product that can be measured spectrophotometrically. Recently, the dye XTT has been found to substitute for, and have certain advantages over, MTT (Loo et al., 1993).

Among the assays currently used to monitor apoptosis, the most common are visual methods, such as light or electron microscopy to determine cellular morphology, vital dye exclusion, nuclear staining with fluorescent dyes such as propidium iodide, acridine orange, bisbenzimide (Hoechst 33258 and 33342) and green fluorescent protein (GFP), indirect methods such as fluorescence-activated cell sorting (FACS) of fluorescently labeled cells, assays for the release of the cytosolic enzyme lactate dehydrogenase, the MTT/XTT assay, detection of binding of annexin V or anti-phosphatidylserine antibodies, detection of DNA fragmentation, detection of the release of soluble nuclear matrix proteins, such as nuclear matrix protein A, from cells, detection of the loss of lamins from the nuclear envelope and detection of free nucleosomes. Additionally, in certain instances these assays are combined, such as determining the binding of annexin V or anti-phosphatidylserine antibodies in conjunction of dye exclusion, such as propidium iodide.

A. Dye Exclusion

Staining of cultured cells with vital dyes, such as trypan blue or propidium iodide, is one commonly used approach to quantify cell death. These dyes are available from a number of commercial sources, including Sigma-Aldrich Chemical Company (St. Louis, Mo.). This assay is based on the observation that viable cells with intact membranes exclude specific dyes such as trypan blue and propidium iodide, which can easily be quantified by light (trypan blue) or fluorescence (propidium iodide) microscopy (Loo and Rillema, 1998). The percentage of cells positive for dye staining in various culture conditions is used to calculate cell survival. This method is useful for screening multiple samples or treatment conditions, but can underestimate cell death since membrane integrity can be intact until late in apoptosis. However, vital dye staining, such as trypan blue and propidium iodide, is not specific for apoptosis and will also stain necrotic cells.

B. GFP Nuclear Stain

Visualization of morphological features of apoptosis in the nucleus of the cells such as chromatin condensation and nuclear fragmentation is determined in this assay (Plotkin et al., 1998). Cells are stably transduced with a viral vector carrying green fluorescent protein (GFP) cDNA with a nuclear localization sequence designed to target GFP to the nucleus. The cells are subjected to different culture conditions, counted by phase microscopy, followed by enumeration of the number of cells with apoptotic nuclei using fluorescent microscopy. The GFP allows visualization and quantitation of nuclear morphological changes and blebbing.

C. Binding of Annexin V and/or Anti Phosphatidylserine Antibodies

Phosphatidylserine is a negatively charged phospholipid that is normally restricted to the inner surface of the plasma bilayer (Cullis et al., 1979). In the early stages of apoptosis, cells lose their membrane asymmetry, and translocate phosphatidylserine to the outer leaflet of the plasma membrane, where it can be recognized by macrophages, eventually leading to elimination (Fadok et al., 1992). Extracellular calcium has been shown to be required for the translocation of phosphatidylserine (Hampton et al., 1996). The translocation of phosphatidylserine has been demonstrated in a variety of cell types undergoing apoptosis induced by a number of different stimuli, and has also been shown to precede other apoptotic events (Martin et al., 1995).

Phosphatidylserine can be detected by its high affinity binding to annexin V or anti-phosphatidylserine antibodies (Loo and Rillema, 1998). Annexin V is a calcium-dependent phospholipid-binding protein that has a high affinity for phosphatidylserine (Moss et al., 1991). The binding of annexin V has been shown to coincide with chromatin condensation, an early indicator of apoptosis, in apoptotic B cells (Koopman et al., 1994).

Annexin V labeled with a number of different indicator molecules and anti-phosphatidylserine monoclonal antibodies are available from a variety of sources. Annexin V labeled with either FITC or biotin, as well as a monoclonal anti-phosphatidylserine antibody, are available commercially from Oncogene Research Products (Cambridge, Mass.).

D. Detection of DNA Fragmentation

Cellular apoptosis is characterized morphologically by cell shrinkage, nuclear pyknosis, chromatin condensation and blebbing of the plasma membrane (Kerr et al., 1972). One of the events in apoptosis is the activation of an endogenous endonuclease that cleaves the unprotected DNA between the nucleosomes, while leaving the DNA wrapped around the histone core intact. Since the amount of DNA that is wrapped around the core is fairly constant, about 180 to 200 bp, this produces a ladder of DNA fragments that can be readily detected when separated by electrophoresis (Wyllie, 1980; Arends et al., 1990). Additionally, the DNA fragments produced by the endonuclease cleavage can be labeled with radioactivity, fluorescent dyes or with enzymes, such as alkaline phosphatase or horseradish peroxidase, that catalyze reactions that produce a detectable chromogenic compound.

Kits for the labeling and detection of these DNA fragments are commercially available from sources such as Oncogene Research Products (Cambridge, Mass.).

E. Detection of Release of Soluble Nuclear Matrix Proteins

Nuclear matrix proteins (NMP) form the internal structural framework of the nucleus, and are associated with both DNA and RNA processes (dejong et al., 1990). The nuclear matrix is highly insoluble in the intact nucleus, however, soluble NMP are released from the nucleus of cells undergoing apoptosis (Miller et al., 1994). The breakdown of the nuclear matrix likely accounts for certain morphological changes seen in the nucleus of an apoptotic cell. The amount of soluble NMP is a function of the number of dead and dying cells, and thus quantitation of soluble NMP is another assay for apoptosis (Miller et al., 1992, 1993).

Monoclonal antibodies that bind to various proteins of the nuclear matrix are available from a variety of sources. Four monoclonal antibodies against nuclear matrix proteins, as well as a kit for detecting soluble nuclear matrix proteins, are available commercially from Oncogene Research Products (Cambridge, Mass.).

F. Detection of the Loss of Lamins From the Nuclear Envelope

The nuclear envelope of mammalian cells is composed of numerous different proteins, including the nuclear lamins (McKeon et al., 1986; Franke, 1987). Four types of lamins have been identified to date: lamin A, lamin B1, lamin B2 and lamin C. Lamin A has been shown to be a substrate for capase during apoptosis (Nagata, 1997), and lamin B has been shown to be depleted from apoptotic cells (Miller et al., 1994). Thus, detection of the loss of lamins from the nucleus, for example by using labeled antibodies that specifically bind to one or more lamin protein, is another assay useful for detecting apoptosis.

Anti-lamin antibodies are available from a number of sources. A monoclonal anti-lamin B antibody is available commercially from Oncogene Research Products (Cambridge, Mass).

G. Detection of Free Nucleosomes

When a cell enters the apoptosis pathway, an endonuclease is induced that cleaves the DNA in the linker region between the nucleosomes (Wyllie, 1980; Arends et al., 1990; Bortner et al., 1995). While the histone proteins are not accessible in intact nucleosomes, as the nucleosomes are degraded during apoptosis the histone proteins become accessible, and can be detected with anti-histone antibodies. Thus, detection of the histone proteins from free nucleosomes is another assay of apoptosis.

Anti-histone antibodies are available from a number of sources. A kit for detecting free nucleosomes is available commercially from Oncogene Research Products (Cambridge, Mass.).

XI. Animal Models

A number of different animal models have been described to study osteoporosis (Geddes, 1996). These animals fall into four main classes: the resorption-predominant modeling rat models; the resorption-predominant remodeling animal models; the formation deficit-predominant modeling mouse and rat models, and the formation deficit-predominant remodeling animal models.

A. Resorption-Predominant Modeling Rat Models

Rat models that have been described that fall into this class include: acute post-ovariectomized (Shen et al., 1995); calcium restricted (Stauffer et al., 1973); castrated male (Vanderschueren et al., 1993); calcium restricted ovariectomized (Matsumoto et al., 1985); lactating calcium restricted ovariectomized (Anderson et al., 1990); lactating calcium restricted (Garner et al., 1987); drug-induced rat models, including retinoid (Trechsel et al., 1987), PTH (Russell et al., 1970), heparinized (Monreal et al., 1990), acidified (Barzel, 1976) and thyroid excess (Ongphiphadhanakul et al., 1992); and immobilized rat models, including sciatic denervectomy (Turner and Bell, 1986), tenotomized (Zeng et al., 1993), tail suspended (Globus et al., 1986), bandaged hindlimb (Jee et al., 1991), space flight (Vailas et al., 1992), immobilized ovariectomized (Okumura et al., 1987), and immobilized calcium restricted (Weinreb et al., 1991).

B. Resorption-Predominant Remodeling Animal Models

Animal models from a number of different species have been described that fall into this class, including: lactating pig (Spenser, 1979); ovariectomized dog (Kimmel, 1991); calcium restricted ovariectomized dog (Geusens et al., 1991); ovariectomized ferret (Mackey et al., 1995); calcium restricted rabbit (Wu et al., 1990); ovariectomized monkey (Jerome et al., 1994; Miller et al., 1986); GnRH monkey (Mann et al., 1990) and ovariectomized baboon (Jerome et al., 1986; Thompson et al., 1992).

C. Formation Deficit-Predominant Modeling Mouse and Rat Models

The animal models that have been described that fall into this class include: aged normal mouse (Weiss et al., 1991); aged normal rat (Jee, 1991); senescence-accelerated rat (Matsushita et al., 1986); aged ovariectomized rat (Ibbotson et al., 1992); stroke-prone rat (Yamori et al., 1991); glucocorticoid-treated rat (Simmons and Kunin, 1967); diabetic rat (Sasaki et al., 1991), immobilized rat (Jee et al., 1991) and inflammation-mediated rat (Lempert et al., 1991).

D. Formation Deficit-Predominant Remodeling Animal Models

Animal models from a number of different species have been described that fall into this class, including: aged calcium-restricted ovariectomized pig (Mosekilde et al., 1993); aged dog (Jee et al., 1970); immobilized dog (Waters et al., 1991; Uhthoff and Jaworski, 1978); glucocorticoid dog (Quarles, 1992); glucocorticoid sheep (Chavassieux et al., 1993); aged sheep (Newman et al., 1995); immobilized sheep (Rubin et al., 1988); aged monkey (Pope et al., 1989) and immobilized monkey (Wronski and Morey, 1983).

XII. Pharmaceutical Compositions and Routes of Administration

The present invention also contemplates the use of pharmaceutical compositions that comprise a dosage range of the CD40 ligands or agonists that provide a beneficial prophylactic or therapeutic effect. In preferred embodiments, the CD40 ligand or agonist is administered to the animal at a dose of between about 0.5 µg/kg and about 0.5 mg/kg. "Between about 0.5 µg/kg and about 0.5 mg/kg" will be understood to include all sub-ranges and values within this range, including, but not limited to, doses of between about 1 µg/kg and about 0.5 mg/kg, between about 10 µg/kg and about 0.5 mg/kg, between about 50 µg/kg and about 0.5 mg/kg, between about 100 µg/kg and about 0.5 mg/kg, between about 0.5 µg/kg and about 0.1 mg/kg, between about 0.5 µg/kg and about 0.05 mg/kg, between about 0.5 µg/kg and about 0.01 mg/kg, as well as doses of about 1 µg/kg, about 5 µg/kg, about 10 µg/kg, about 25 µg/kg, about 50 µg/kg, about 100 µg/kg, about 250 µg/kg, and about 0.5 mg/kg.

Among the preferred routes of administration are intravenous and subcutaneous injection. Thus, the active CD40 ligand and/or agonist compositions may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Another suitable treatment method involves the use of nasal solutions or sprays, aerosols or inhalants. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines.

Inhalations and inhalants are pharmaceutical preparations designed for delivering a drug or compound into the respiratory tree of a patient. A vapor or mist is administered to deliver agents into the systemic circulation. Inhalations may be administered by the nasal or oral respiratory routes. Another group of products, also known as inhalations, and sometimes called insufflations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered dose of the inhalation is propelled into the respiratory tract of the patient.

The administration of inhalation solutions is most effective if the droplets are sufficiently fine and uniform in size so that the mist reaches the bronchioles. Particle size is of importance in the administration of this type of preparation. It has been reported that the optimum particle size for penetration into the pulmonary cavity is of the order of 0.5 to 7 µm. Fine mists are produced by pressurized aerosols and hence their use in considered advantageous.

The pharmaceutical compositions disclosed herein may also be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a c binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

XIII. Liposomes and Nanocapsules

In certain embodiments, the inventors contemplate the use of liposomes and/or nanocapsules for the introduction of particular peptides or nucleic acid segments into host cells. Such formulations may be preferred for the introduction of pharmaceutically-acceptable formulations of the nucleic acids, peptides, and/or antibodies disclosed herein. The formation and use of liposomes is generally known to those of skill in the art (see for example, Couvreur et al., 1977, which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Chorn, 1987).

Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles (Couvreur et al., 1977; 1988), which meet these requirements, are contemplated for use in the present invention.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

In addition to the teachings of Couvreur et al. (1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition that markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

XIII. Kits

Therapeutic kits comprising, in a suitable container, one or more CD40 ligand and/or CD40 agonist protein composition of the present invention, in combination with at least a second, distinct anti-bone loss agent and/or one or more steroids, in a pharmaceutically acceptable formulation represent another aspect of the invention. In a preferred embodiment the CD40 ligand and/or CD40 agonist protein compositions are gp39 or anti-CD40 monoclonal antibody compositions. The CD40 ligand and/or CD40 agonist protein compositions may be native CD40 ligand and/or CD40 agonist proteins, truncated CD40 ligand and/or CD40 agonist proteins, site-specifically mutated CD40 ligand and/or CD40 agonist proteins, or CD40 ligand and/or CD40 agonist protein-encoded peptide epitopes, or alternatively antibodies which bind CD40, CD40 ligand and/or CD40 agonist proteins, truncated CD40, CD40 ligand and/or CD40 agonist proteins, site-specifically mutated CD40, CD40 ligand and/or CD40 agonist proteins, or CD40, CD40 ligand and/or CD40 agonist protein-encoded peptide epitopes. In other embodiments, the CD40 ligand and/or CD40 agonist protein compositions may be nucleic acid segments encoding native CD40 ligand and/or CD40 agonist proteins, truncated CD40 ligand and/or CD40 agonist proteins, site-specifically mutated CD40 ligand and/or CD40 agonist proteins, or CD40 ligand and/or CD40 agonist protein-encoded peptide epitopes. Such nucleic acid segments may be DNA or RNA, and may be either native, recombinant, or mutagenized nucleic acid segments.

The kits may comprise a single container that contains the CD40 ligand and/or CD40 agonist protein compositions and the at least a second, distinct anti-bone loss agent and/or one or more steroids. The container may, if desired, contain a pharmaceutically acceptable sterile excipient, having associated with it the CD40 ligand and/or CD40 agonist protein compositions and the at least a second, distinct anti-bone loss agent and/or one or more steroids. The formulation may be in the form of a gelatinous composition, e.g., a collagenous-protein composition, or may even be in a more fluid form that nonetheless forms a gel-like composition upon administration to the body. In these cases, the container means may itself be a syringe, pipette, or other such like apparatus, from which the CD40 ligand and/or CD40 agonist protein compositions and the at least a second, distinct anti-bone loss agent and/or one or more steroids may be applied to a tissue site, skin lesion, wound area, or other desired site application. However, the single container means may contain a dry, or lyophilized, mixture of a CD40 ligand and/or CD40 agonist protein compositions and the at least a second, distinct anti-bone loss agent and/or one or more steroids, which may or may not require pre-wetting before use.

Alternatively, the kits of the invention may comprise a distinct container for each component. In such cases, separate or distinct containers would contain the CD40 ligand and/or CD40 agonist protein compositions and the at least a second, distinct anti-bone loss agent and/or one or more steroids, either as a sterile solution or in a lyophilized form. The kits may also comprise a third container for containing a sterile, pharmaceutically acceptable buffer, diluent or solvent. Such a solution may be required to formulate the CD40 ligand and/or CD40 agonist protein compositions and the at least a second, distinct anti-bone loss agent and/or one or more steroids into a more suitable form for application to the body, e.g, as a topical preparation, or alternatively, in oral, parenteral, or intravenous forms. It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention.

The container(s) will generally be a container such as a vial, test tube, flask, bottle, syringe or other container, into which the components of the kit may placed. The CD40 ligand and/or CD40 agonist protein compositions and the at least a second, distinct anti-bone loss agent and/or one or more steroids may also be aliquoted into smaller containers, should this be desired. The kits of the present invention may also include material for containing the individual containers in close confinement for commercial sale, such as, e.g., injection or blow-molded plastic containers into which the desired vials or syringes are retained. Irrespective of the number of containers, the kits of the invention may also comprise, or be packaged with, an instrument for assisting with the placement of the CD40 ligand and/or CD40 agonist protein compositions and the at least a second, distinct anti-bone loss agent and/or one or more steroids within the body of an animal. Such an instrument may be a syringe, pipette, forceps, or any such medically approved delivery vehicle.

The following example is included to demonstrate preferred embodiments of the invention. It should be appreciated by those of skill in the art that the techniques disclosed in the example that follows represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Expression of CD40 on Osteoblasts and Osteocytes

Prior to the present disclosure, the expression of CD40, the receptor for CD40L, was thought to be limited to B cells, follicular dendritic cells, epithelial cells, hematopoietic progenitor cells and some carcinomas. However, the present Example demonstrates for the first time that CD40 is expressed abundantly on primary osteoblasts (PRI OBI), osteoblast cell lines (MC3T3, OCT-1 and 2T3) and an osteocyte cell line (MLO-Y4).

A. Materials and Methods

1. Monoclonal Antibodies and Reagents

Fluorescent labeled monoclonal antibodies (mAb) against CD40 (clone HM40-3, 3/23), MHC class II (I-A$^b$ haplotype, clone 25-9-3), MHC class I (H-2K$^b$, cloneKH95), CD40L (clone MR1), CD11a (clone 2D7), CD11b (clone M1/70), CD86 (clone GL1), CD54 (ICAM-1 marker, clone 3E2), CD3/CD2 (T cell marker, clone 145-2C11) and B220 (B cell marker, clone RA36B2) and the respective isotype control (hamster IgM, rat IgG2a) were obtained from Pharmingen (San Diego, Calif.). Reagents for apoptosis staining included propidium iodide (Sigma, St. Louis, Mo.) and Annexin V FITC (Pharmingen, San Diego, Calif.). NLDC 145 (rat anti-mouse IgG) was obtained from Chemicon International, Inc. (Temecula, Calif.).

Tissue culture media DMEM and fetal bovine serum was obtained from Life Technologies, Inc. (Gaithersburg, Md.) and calf serum (CS) was from Hyclone Laboratories, Inc (Logan, Utah). Recombinant growth factors GM-CSF, IL-4 and TNFα was obtained from R and D (Minneapolis, Minn.). All other reagents were obtained from Sigma Chemical Co. (St. Louis, Mo.) unless otherwise stated.

2. Cell Lines and Culture Conditions

The establishment of murine long bone osteocyte-Y4 (MLO-Y4) cell line as a osteocyte cell line has been described (Kato et al., 1997). The osteoblastic cell line MC3T3-E1, which was established from normal mouse calvaria, was obtained from Dr Hiroaki Kodama (Ohu University, Fukushima, Japan). The osteoblastic cell line, OCT-1, which was established from osteocalcin promoter driven T-antigen transgenic mouse calvaria, was obtained from Dr. Di Chen (University of Texas Health Science Center at San Antonio, San Antonio, Tex.) (Chen et al., 1995). The osteoblastic cell line 2T3 was obtained from Dr. Steve Harris (University of Texas Health Science Center at San Antonio, San Antonio, Tex.) (Ghosh-Choudhury et al., 1996). Primary osteoblastic cells were isolated from neonatal mouse calvaria by sequential collagenase digestion according to previously described method of Takahashi and co-workers (Takahashi et al., 1988).

Dendritic cells (DCs) were derived from bone marrow as previously described (Inaba et al., 1992a, b; Steinman et al., 1993; Ahuja et al., 1998). The femurs and tibias were flushed with 3 to 5 ml of phosphate-buffered saline (PBS) in 1% bovine serum albumin. Particulate matter was filtered and red blood cells lysed. Bone marrow cells were differentiated into DCs by culturing in RPMI (Life Technologies, Inc., Gaithersburg, Md.) supplemented with 10% FCS, gentamicin (10 μg/ml) and recombinant murine cytokines GM-CSF (50 ng/ml) and IL-4 (1 ng/ml) for 7–10 days. On day 3 and day 5 the nonadherent cells (contaminating granulocytes and lymphocytes) were removed and replaced with fresh medium and growth factors. On day 7 the nonadherent cells were removed and plated in either 24 well or 96 well plates. In several experiments bone marrow-derived DCs were stained and analyzed by FACS for DC, monocytes and lymphocyte cell surface markers. Phenotypically, bone-marrow derived DCs expressed abundant MHC class II, CD80, CD86, CD40, CD11b, DEC 205, and CD11c, and lacked CD3 or B220 (T or B cell markers).

3. Flow Cytometry

For flow cytometric analysis single cell suspensions were washed twice with phosphate buffered saline (PBS) containing 5% fetal calf serum (FCS, Life Technologies Inc., Gaithersburg, Md.) and 0.1% sodium azide (washing solution). Non-specific binding was blocked by incubating cells with PBS containing 5% FCS for 30 minutes at 4° C. Approximately 100,000 to 200,000 cells were aliquoted in 6 ml polypropylene tubes and incubated with the FITC isotype control Ab or FITC CD40 mAb for 30 minutes in the dark. The cells were washed twice and fixed in 0.1–0.2 ml of PBS containing 0.1% formaldehyde prior to analysis. Flow cytometry was done using a FACS Calibur with Simultest analysis software (Becton Dickinson, San Jose, Calif.) (Ahuja et al., 1998).

4. RT-PCR™ for CD40 and CD40L

Total RNA was isolated from cells using RNAzol B (Life Technologies) according to manufacturer's instructions. cDNA was synthesized from 5 μg of total RNA in a 20 μl reaction mixture containing 1×first stand buffer buffer, 500 μM dNTPs, 10 mM DTT, 500 ng oligo (dT) 12–18 primer and 200 U Superscript II reverse transcriptase (Gibco BRL Life Technologies, Baltimore, Md.). One μL cDNA was amplified in a 50 μl PCR™ reaction containing 1×PCR™ buffer (Fischer Scientific, Pittsburgh, Pa., USA), 200 nM of 5' and 3' primer, 200 μM dNTP mixture, 2 mM MgCl$_2$ and 2.5 U of Taq DNA polymerase (Gibco BRL). Amplifications were performed in a DNA thermal cycler (Perkin Elmer) for 25–40 cycles following the reaction profile: 94° C. for 45 secs., 58° C. for CD40 or 54° C. for CD40L for 30 secs., and 72° C. for 45 secs. Aliquots of PCR™ products were run on 1.5% agarose gels and visualized by UV transillumination. Controls included a mouse spleen cDNA (positive for mCD40 and CD40L) and a house keeping gene GAPDH.

5. Treatment of the Cells with Factors

The MLO-Y4 cells were pretreated with CD40L (0.5–1.5 μg/ml) for 15 mins. followed by treatment with either dexamethasone at $10^{-6}$ M ($10^{-7}$M in earlier studies), TNFα at 1 ng/ml or etoposide at 50 μM for 6 hrs. The cells were cultured in 2.5% FBS/2.5% CS in α-MEM, 5% CO$_2$, 37° C.

6. Assays for Cell Death/Apoptosis

Three different assays were used to assess cell death/apoptosis: trypan blue exclusion; green fluorescent protein (GFP) nuclear stain; and FACS staining for annexin V/propidium iodide.

Trypan Blue Exclusion: Staining of cultured cells with vital dyes such as trypan blue is commonly used approach to quantify cell death. This is based on the premise that viable cells with intact membranes will exclude specific dyes such as trypan blue, which can easily be quantified under light microscopy (Rillema, 1998). The percentage of trypan blue positive cells in each culture condition was used to calculate cell survival. This method is usefull for screening multiple samples or treatment conditions, but can underestimate cell death since membrane integrity can be intact until late in apoptosis. Trypan vital dye staining is not specific for apoptosis and will also stain necrotic cells. This was confirmed by additional analysis discussed below.

Apoptosis of MLO-Y4 or calvaria cells was quantified by trypan blue staining (Jilka et al., 1998). Nonadherent cells were combined with adherent cells released from the culture dish using trypsin-EDTA, resuspended in medium containing serum, and collected by centrifugation. Subsequently, 0.04% trypan blue was added and the percentage of cells exhibiting both nuclear and cytoplasmic staining was determined using a hemocytometer. At least 100 cells per condition were counted. Trypan vital dye staining is not specific for apoptosis and will also stain necrotic cells. Apoptosis was confirmed by additional analyses as shown below.

GFP Nuclear Stain: Visualization of morphological features of apoptosis in the nucleus of the cells, such as chromatin condensation and nuclear fragmentation, was determined in this assay. During apoptosis the nucleus becomes shrunken and pyknotic as a result of DNA degradation. MLO-Y4 cells were stably transduced with a retroviral vector carrying the green fluorescent protein (GFP) CDNA with a nuclear localization sequence designed to target the GFP to the nucleus (Plotkin et al., 1998). MLO-Y4 cells stable transduced with nuclear GFP were fixed in neutral buffer formalin for 8 min, and apoptosis was assessed by enumerating cells exhibiting chromatin condensation and nuclear fragmentation under a fluorescent microscope. At least 500 cells from fields selected by systematic random ampling were examined for each condition (Plotkinn et al., 1999; Jilka et al., 1999).

FACS Staining for Annexin V/Propidium Iodide: In early stages of apoptosis the cells lose membrane asymmetry and translocate the membrane phospholipid phosphatidylserine to the outer leaflet of the plasma membrane, where it can be detected by its high affinity binding to annexin V (Rillema, 1998). Annexin V is a calcium-dependent phospholipid-binding protein that has a high affinity for phosphatidylserine. Prolonged apoptosis can cause cell death and these non-viable cells stain positive for vital dye Propidium Iodide (PI) as well as Annexin V. Apoptotic cells stain Annexin V positive and Propidium iodide negative.

The staining protocol includes washing single cell suspension twice with PBS and resuspending in 1×binding buffer (0.1 M HEPES/NaOH, pH 7.4; 1.4 mM NaCl; 25 mM CaCl$_2$) at a concentration of one million cells/ml. The cells are aliquoted (100 μl) in polypropylene tubes, incubated with annexin V FITC (5 μl) and propidium iodide (10 μl) for 15 minutes at 4° C. in the dark, and analyzed by flow cytometry within 1 hour. Flow cytometric analysis was performed on a FACScan flow cytometer using simultest software (Becton Dickinson, Mountain View, Calif.) by analyzing 5,000 to 10,000 cells per sample using wide light scatter gates to include late apoptotic cells.

7. Thymidine Incorporation Assay

Antigen presentation was analyzed in an allogeneic MLR where dendritic cells derived from the Balb/c mouse were cultured with splenocytes derived from C57/B16 (positive control) or MLO-Y4 cells were cultured with splenocytes from the Balb/c mouse. Briefly, varying concentrations of antigen presenting cells (10,000 to 100,000/well) were cultured in triplicate with 100,000 splenocytes for 72 hours. For thymidine incorporation cells were pulsed with 0.5 μCi of tritiated thymidine (New England Nuclear Research Products, Boston, Mass.) in the last 8 h of the 72 h culture (Ahuja et al., 1998). The cells were harvested on glass fiber filters Pharmacia, Uppsala, Sweden) and counted on a B-scintillation counter (LKB, Wallace, OY, Finland).

B. Results

1. Osteocytes Share Phenotypic/Cell Surface Markers With Immune Cells

Since osteocytes are buried deep in the mineralized matrix and are relatively inaccessible, it has been difficult to obtain a relatively homogeneous pure population of primary osteocytes in culture. To this end, the inventors have recently described the establishment of an osteocyte cell line, MLO-Y4 (Kato et al., 1997). As assessed by the morphological appearance of bone marrow derived dendritic cells and osteocyte MLO-Y4 cells in 4 day culture, this cell line produces extensive, complex dendritic processes that are a phenotypic hallmark of dendritic cells. Dendritic cells are long lived antigen presenting cells that differentiate from haematopoitic cells. Dendritic cells form a link between the innate and adaptive arm of the immune system by presenting antigen to lymphocytes. Thus the inventors determined if the murine osteocyte like cell line MLO-Y4 shared any cell surface markers with the murine dendritic cells.

Table 5 shows the cell surface expression of haematopoietic, lymphoid, myeloid and dendritic cell markers on MLO-Y4 cells. MLO-Y4 cells were stained with fluorescent labeled antibodies against cell surface markers characteristic of dendritic cells and analyzed by FACScan. In the right column the signs −, +, ++, +++, and ++++ denote zero, one, two, three, four log increase in fluorescence with a cell surface marker specific monoclonal antibody compared to isotype control antibody. Also shown are the known cell surface distribution of the markers. In addition to Table 5, MLO-Y4 cells were also found to express the E11 antigen (Bonewald et al., 2000), reported to be an osteocyte-specific antigen according to Schulze and co-workers (Schulze et al., 1999).

TABLE 5

MLO-Y4 Cells Are Not Haematopoietic Progenitor Cell Derived Dendritic Cells

| Cell Surface Markers | Known Cell Distribution | MLO-Y4 cells |
| --- | --- | --- |
| CD45 | all haematopoietic cells | − |
| CD3 | T cells | − |
| B220 | B cells | − |
| CD4 | monocytes, lymphocytes | − |
| CD11b | monocytes, macrophages, dendritic cells | − |
| Gr-1 | neutrophils | − |
| CD11c | dendritic cells, monocytes macrophages | − |
| DEC205 | dendritic cells | − |
| MHC-class I | all nucleated cells | +++ |
| MHC-class II | all haematopoietic cells | − |
| CD40L | T cells, vascular smooth muscle cells | − |
| CD40 | B cells, vascular smooth muscle cells, | ++++ |

Analysis of MLO-Y4 cells by FACS revealed that they did not express CD45, which is a marker present in abundance on all hematopoietic cells. Markers for T and B lymphocytes (CD3 and B220), granulocytes (Gr-1), monocytes/macrophages (CD4, CD11b, CD11c) and dendritic cells (DEC 205, CD11c, MHC class II, CD86, CD80) were absent. However the MLO-Y4 cells did express abundant MHC-class I molecule that is expressed by all cells in the body, but lacked MHC class II and CD45 which is expressed by all haematopoietic cells.

2. MLO-Y4 Cells Do Not Have Antigen Presenting Function

Both the mesenchymal cell derived osteoblasts differentiating into mature osteocytes and the haematopoietic progenitor cells differentiating into dendritic cells originate in the bone marrow (Stein, 1996). The long complex dendritic processes and abundant expression of gap junction protein connexin 43 suggest that the MLO-Y4 cells have features important for cell to cell communication. Dendritic cells by their very name have long dendritic processes and communicate to the adaptive arm of the immune cells (lymphocytes). They process foreign proteins into small peptides and present it in the groove of the MHC complex so that it can be recognized by lymphocytes.

Figure 1B:
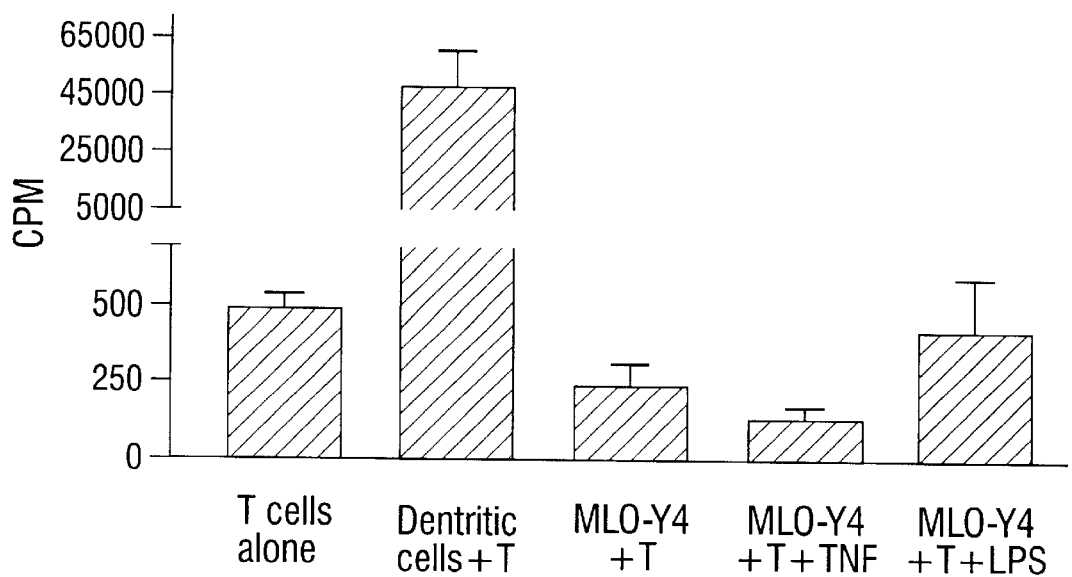

Dendritic cell mediated T cell proliferation was compared with that of MLO-Y4 cells in a mixed lymphocytic reaction. In contrast to dendritic cells used as a control, both unstimulated and MLO-Y4 cells stimulated with TNF or LPS were unable to induce T cell proliferation (FIG. 1A and FIG. 1B). This confirmed that the MLO-Y4 cells did not express any cell surface markers suggestive of dendritic cells, did not present antigen like dendritic cells, and did not derive from hematopoietic progenitor cells.

3. Osteocytes Share TNF Receptor/Ligands with Immune Cells

Several members of the TNF receptor/ligand family have been identified to play important roles in survival or apoptosis of immune cells, especially dendritic cells and B lymphocytes. The cell surface expression of CD40, RANKL/TRANCE and MHC class I on MLO-Y4 cells was investigated and the data reviewed as histograms of cell numbers vs. log fluorescence intensity. Background staining was distinguished using an isotype control antibody for each cell line, allowing any shift in fluorescence with the specific monoclonal antibodies against CD40, RANKL and MHC class I, respectively, to be determined. Results from these studies showed, surprisingly, that MLO-Y4 cells expressed abundant CD40 and moderate amounts of RANKL/TRANCE, but lacked CD40L. Expression of mRNA transcripts for CD40 and absence of CD40L was also confirmed by RT-PCR™ using specific primers.

CD40 /CD40L and TRANCE/RANKL belong to a large family of TNF receptor/ligand pairs that play a crucial role in B cells and dendritic cell survival/death by modulating apoptosis. CD40, the receptor for CD40L, is expressed on follicular dendritic cells, B cells, epithelial cells, haematopoietic progenitor cells and some carcinomas, whereas expression of its ligand, CD40L, is limited to activated T cells, dendritic cells, vascular smooth muscle cells, vascular endothelial cells and macrophages. Recently TRANCE/RANKL was also identified independently as a dendritic cell specific survival factor and as an osteoclast differentiation factor. This seems to suggest that the MLO-Y4 cells were unlikely to be haematopoietic in origin, but did share the expression of survival proteins with the long lived antigen presenting immune cells (dendritic cells and B lymphocytes).

4. Bone cells do not Express mRNA for CD40L

Using primers specific for CD40 and CD40L, the presence of mRNA transcripts for CD40, and the absence of transcripts CD40L, was confirmed by RT-PCR™ in primary osteoblasts, the osteoblast OCTI cell line and the osteocyte MLO-Y4 cell line. RT-PCR™ for CD40 showed abundant expression in primary osteoblasts, the OCT-1 cells and the MLO-Y4 cells (as compared to mouse spleen as a positive control), whereas no bands were detectable for CD40L (although this is abundant in the mouse spleen cell control). The GAPDH housekeeping gene was used as an overall control.

5. CD40 Expression in Bone is Not Limited to Osteocytes

CD40 expression in primary osteoblasts; the osteoblast cell lines MC3T3, OCT-1 and 2T3; and the osteocyte cell line MLO-Y4 was determined by flow cytometry. The data was analyzed as histograms of cell numbers against log fluorescence intensity. The background staining for each cell line was determined using an isotype-matched, control antibody, allowing any shift in fluorescence with the CD40 antibody to be determined.

These studies showed that the primary osteoblast, the osteoblast cell lines (MC3T3, OCT-1, 2T3) and the osteocyte cell line (MLO-Y4) all have abundant expression of CD40 as determined by FACS analysis using an antibody that binds to the surface of CD40. By plotting the mean log fluorescent intensity of the fluorescent-labeled anti-CD40 antibody as a histogram on the horizontal axis against the cell number on the vertical axis, the shift of the histogram to the right using the test antibody (as compared to the isotype-matched, control antibody) indicates a log fold increase in fluorescence when the cells are incubated with the anti-CD40 antibody. This suggests that these cells express abundant CD40. Primary osteoblasts as well as the MLO-Y4 cells seem to have two populations of cells with different fluorescent intensity. Morphologically, two populations of cells can be identified in the MLO-Y4 cells, which suggests that the expression of CD40 may be influenced by either differentiation or cell cycle.

6. CD40L Prevents Apoptosis in Osteocytes

Studies in mice administered glucocorticoids suggest that the effects of long term administration of steroids on the bone is due to decreased bone formation, which results from higher numbers of apoptotic/dead osteoblasts (Weinstein et al., 1998). Lesser number of these cells could account for changes seen with glucocorticoid induced bone disease. A decrease in osteoblast and osteocyte cell number due to death/apoptosis has also been demonstrated in patients who have glucocorticoid-induced osteoporosis (Weinstein et al., 1998). Bone loss can also occur due to the production of inflammatory cytokines, such as TNFα, which induce apoptosis and are elevated in conditions such as inflammatory arthritis and post-menopausal osteoporosis (Pacifici et al., 1991; Rickard et al., 1992; Kimble et al., 1995). Thus, it was hypothesized that administration of CD40L may affect apoptosis in osteocytes induced by steroids or TNFα.

There are a large number of assays to analyze apoptotic cell death. As the cells undergo apoptosis there are many processes occurring simultaneously, but it is not clear which of these processes is crucial to the outcome of apoptosis. An assay may measure only one critical component of the apoptotic process. Hence, in a new system, it is important to evaluate the apoptotic process by more than one technique.

Figure 2:
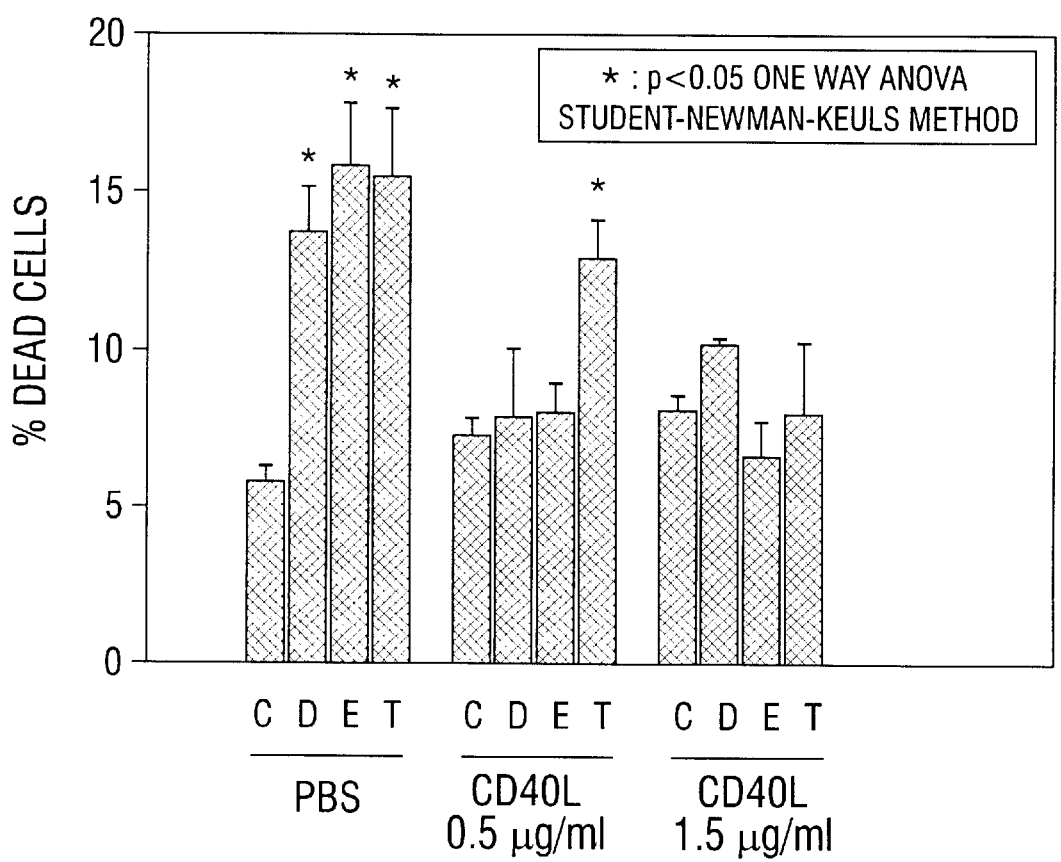
FIG. 2. Effect of CD40L on apoptosis induced by different agents on MLO-Y4 osteocytic cell line, as measured by trypan blue uptake. Cells were pretreated with PBS, CD40L (0.5–1.5 $\mu$g/ml), followed by no treatment control (C), dexamethasone (D) at $10^{-6}$M ($10^{-7}$ M in initial studies), TNFα (T) at 1 ng/ml or etoposide (E) at 50 $\mu$M. The percentage of apoptotic cells is shown on the Y-axis. In each treatment, the percentage of apoptotic cells was significantly lower in cells that had been pretreated with CD40L (*p<0.05 significantly different from controls one way anova). Controls included no treatment, CD40L alone, dexamethasone at $10^{-6}$M ($10^{-7}$ M), TNFα at 1 ng/ml and etoposide at 50 μM alone.

The inventors have therefore used three different assays to evaluate cell death/apoptosis. Soluble, trimeric CD40L was prepared as described in U.S. Pat. No. 5,716,805, incorporated herein by reference. Trypan blue exclusion was used as a measure of cell death in cells pretreated with CD40L (0.5–1.5 μg/ml) followed by dexamethasone at $10^{-6}$ M ($10^{-7}$ M in early studies), TNFα at 1 ng/ml and etoposide at 50 μM (FIG. 2; Table 6). In each treatment, the percentage of apoptotic cell was significantly lower in cells that had been pretreated with CD40L. Controls included no treatment, CD40L alone, dexamethasone at $10^{-6}$ M ($10^{-7}$ M in early studies), TNFα at 1 ng/ml and etoposide at 50 μM alone.

The terminal stage of apoptosis is characterized by chromatin condensation along the nuclear margin that also coincides with DNA cleavage into small fragments. MLO-Y4 cells were stably transfected with nuclear green fluorescent protein and incubated with CD40L (0.5–1.5 μg/ml) followed by dexamethasone ($10^{-7}$ M), TNFα (1 ng/ml) and etoposide (50 μM) (Table 6). In each treatment group, the percentage of apoptotic cells was significantly lower in cells that had been pretreated with CD40L. Controls included no treatment, CD40L alone, dexamethasone alone, TNFα alone and etoposide alone.

The cell membrane changes due to apoptosis were analyzed by Annexin V staining. Similar to the data seen with the methods described above, the percentage of apoptotic cells identified by Annexin V staining cells were lower in the cells treated with CD40L 0.5–1.5 μg/ml followed by dexamethasone ($10^{-6}$ M or $10^{-7}$ M) and TNFα (1 ng/ml or 10 ng/ml). The data from these types of assays are summarized in Table 6.

Table 6 shows a comparison of the three apoptosis assays. MLO-Y4 cells were pretreated with CD40L (0.5 g/ml or 1 μg/ml) for 15 minutes followed by dexamethasone ($10^{-6}$M, or $10^{-7}$M in earlier studies), TNFα (1 nM) or etoposide (50 μM) for 6 hours. They were then analyzed for cell survival by trypan blue exclusion assay, and apoptosis by GFP transfected MLO-Y4 assay and Annexin V staining by FACS as described herein. The results are expressed as percent positive cells, which are dead (trypan blue positive) or are apoptotic (GFP or Annexin V positive). * for Annexin V and trypan-blue, $p<0.05$ significantly different from controls using one way anova, for GFP $p<0.07$ significantly different from controls; for GFP #$p<0.025$ significantly different from the pro-apoptotic agent alone using chi square test.

TABLE 6

CD40L Inhibits Apoptosis Mediated By Dexamethasone

| | Assay (percent positive cells) | | |
|---|---|---|---|
| | Trypan Blue | GFP | Annexin V |
| Control | 5.7 ± 0.4 | 11.3 | 10.7 ± 1.4 |
| CD40L | 7.2 ± 0.5 | 8.7 | 11.5 ± 1.1 |
| Dex | 13.7 ± 1.4* | 24.0* | 23.7 ± 1.6* |
| Dex + CD40L | 7.8 ± 2.2 | 9.9# | 13.7 ± 0.7 |
| TNF | 15.4 ± 2.3 | 17.5* | 18.1 ± 1.2* |
| TNF + CD40L | 12.9 ± 1.3 | 15.0* | 13.9 ± 0.9 |
| Etoposide | 15.8 ± 2.0 | 15.9* | not determined |
| Etoposide + CD40L | 7.9 ± 1.0 | 8.4# | not determined |

*statistically significant compared to controls
significantly different from apoptotic agent The inventors have described various new and surprising findings: first, the conclusive demonstration that the MLO-Y4 osteocyte-like cells do not function as nor express markers of dendritic cells; second, CD40 is expressed abundantly in bone cells, such as osteocytes, primary osteoblasts derived from mouse calvarium, osteoblast cell lines (MC3T3, OCT-1, 2T3) and an osteocyte cell line (MLO-Y4 cells); third, that the ligation of CD40 by CD40L inhibits dexamethasone- and TNFα-induced apoptosis. The role of CD40, a member of the TNF ligand family, in bone biology has not previously been described. This data has important implications in reducing or preventing apoptosis of bone cells, and in clinical applications including, but not limited to, steroid-induced bone loss.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Ahuja, Mummidi, Malech, Ahuja, "Human dendritic cell (DC)-based anti-infective therapy: engineering DCs to secrete functional IFN-gamma and IL-12," *J. Immunol.,* 161:868–876, 1998.

Akagi, Yoshino, Kondo, "The Fas antigen and Fas-mediated apoptosis in B-cell differentiation," *Leuk Lymphoma.,* 28:483–489, 1998.

Allen and Choun, "Large Unilamellar Liposomes with Low Uptake into the Reticuloendothelial System," *FEBS Lett.,* 223:42–46, 1987.

Anderson et al., "The ovariectomized, lactating rat as an experimental model for osteopenia: Calcium metabolism and bone changes," *Bone Miner.* 11:43–53, 1990.

Arends et al., "Apoptosis. The role of the endonuclease," *Am. J. Path.* 136:593–608, 1990.

Aubin and Liu, "The osteoblast lineage," in *Principles of Bone Biology* (Bilezikian, Riasz and Rodan, eds.), Academic Press, New York, N.Y., pp. 51–67, 1996.

Bachmann, Wong, Josien, Steinman, Oxenius, Choi, "TRANCE, a tumor necrosis factor family member critical for CD40 ligand-independent T helper cell activation [see comments]," *J. Exp. Med.,* 189:1025–1031, 1999.

Baker and Reddy, "Modulation of life and death by the TNF receptor superfamily," *Oncogene,* 17:3261–3270, 1998.

Banchereau, Galibert, Arpin, Burdin, Liu, Garrone, "Positive and negative selection of human B lymphocytes in vitro," *Ann. N.Y. Acad. Sci.,* 815:237–245, 1997.

Barbas, Kang, Lerner and Benkovic, "Assembly of combinatorial antibody libraries on phage surfaces: the gene III site," *Proc. Natl. Acad. Sci., USA,* 88(18):7978–7982, 1991.

Barzel, "Acid-induced osteoporosis: An experimental model of human osteoporosis," *Calcif. Tissue Res.* 21:417–422, 1976.

Berman, Mellis, Pollock, Smith, Suh, Heinke, Kowal, Surti, Chess, Cantor, et al., "Content and organization of the human Ig VH locus: definition of three new VH families and linkage to the Ig CH locus," *EMBO J.,* 7(3):727–738, 1988.

Bjorck et al., "Antibodies to distinct epitopes on the CD40 molecule co-operate in stimulation and can be used for the detection of soluble CD40," *Immunology* 83:430–437, 1994.

Black et al., "Randomised trial of effect of alendronate on risk of fracture in women with existing vertebral fractures. Fracture Intervention Trial Research Group," *Lancet* 348:1535–1541, 1996.

Boivin et al., "Ultrastructural immunocytochemical localization of endogenous 1,25-dihydroxyvitamin D3 and its receptors in osteoblasts and osteocytes from neonatal mouse and rat calvaria," *Bone Miner.* 3:125–136, 1987.

Bolivar et al., "Construction and characterization of new cloning vehicles. II. A multipurpose cloning system," *Gene,* 2:95–113, 1977.

Bonewald, "Establishment and characterization of an osteocyte-like cell line, MLO-Y4," *J. Bone Miner. Metab.* 17:61–65, 1999.

Bonewald, Zhao, Zhang, "Expression of the osteocyte-specific antigen, E11, in MLO-Y4 cells and mineralizing osteoblasts", *J. Bone Min Res* 15 suppl 1, S502, Abs. M193, 2000.

Borrebaeck and Moller, "In vitro immunization. Effect of growth and differentiation factors on antigen-specific B cell activation and production of monoclonal antibodies to autologous antigens and weak immunogens," *J. Immunol.,* 136(10):3710–3715, 1986.

Bortner et al., *Trends Cell Biol.* 5:21–26, 1995.

Briscoe, Alexander and Lichtman, "Interactions between T lymphocytes and endothelial cells in allograft rejection," *Curr. Opin. Immunol.* 10:525–531, 1998.

Britton, "Coronavirus motif," *Nature* 353:394, 1991.

Bruder and Caplan, "Terminal differentiation of osteogenic cells in the embryonic chick tibia is revealed by a monoclonal antibody against osteocytes," *Bone* 111:189–198, 1990.

Buckland and Wild, "Leucine zipper motif extends," *Nature* 338:547,1989.

Buckland et al., "A leucine zipper structure present in the measles virus fusion protein is not required for its tetramerization but is essential for fusion," *J. Gen. Virol.* 73:1703, 1992.

Burke et al., "Cloning of large segments of exogenous DNA into yeast by means of artificial chromosome vectors", *Science,* 236, 806–812, 1987.

Buske et al., "In vitro activation of low-grade non-Hodgkin's lymphoma by murine fibroblasts, IL-4, anti-CD40 antibodies and the soluble CD40 ligand," *Leukemia* 11:1862–1867, 1997a.

Buske, Gogowski, Schreiber, Rave-Frank, Hiddemann, Wormann, "Stimulation of B-chronic lymphocytic leukemia cells by murine fibroblasts, IL-4, anti-CD40 antibodies, and the soluble CD40 ligand," *Exp. Hematol.,* 25:329–337, 1997b.

Callard, Armitage, Fanslow and Spriggs, "CD40 ligand and its role in X-linked hyper-IgM syndrome," *Immunol. Today* 14:559–564, 1993.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Carter et al., "Improved oligonucleotide site-directed mutagenesis using M13 vectors," *Nucl. Acids Res.,* 13:4431–4443, 1985.

Chang et al., "Phenotypic expression in *E. coli* of a DNA sequence coding for mouse dihydrofolate reductase," *Nature,* 275:617–624, 1978.

Chavassieux et al., "Glucocorticoid-induced inhibition of osteoblastic bone formation in ewes: A biochemical and histomorphometric study," *Osteoporosis Int.* 3:97–102, 1993.

Chen, Feng, Feng, Harris, Mahy, Mundy, Harris, "Sequence and expression of bone morphogenetic protein 3 mRNA in prolonged cultures of fetal rat calvarial osteoblasts and in rat prostate adenocarcinoma PA III cells," *DNA Cell Biol.,* 14:235–239, 1995.

Chestnut et al., *Am. J. Med.* 99:144–152, 1995.

Choi, "Differentiation and apoptosis of human germinal center B-lymphocytes," *Immunol. Res.,* 16:161–174, 1997.

Chou and Fasman, "Prediction of Protein Conformation," Biochemistry, 13:222–245, 1974a.

Chou and Fasman, "Conformational Parameters for Amino Acids in Helical, .beta.-Sheet, and Random Coil Regions Calculated from Proteins," Biochemistry, 13:211–222, 1974b. Chou and Fasman, "Empirical Predictions of Protein Conformation," Ann. Rev. Biochem., 47:251–276, 1978.

Chou and Fasman, "Prediction of β-Turns," Biophys. J., 26:367–384, 1979.

Clark, "CD40: A cytokine receptor in search of a ligand," Tissue Antigens 35:33–36, 1990.

Clark and Hynes, "1997 keystone symposium on signal transduction by cell adhesion receptors," Biochim. Biophys. Acta., 1333:R9–16, 1997.

Cosman, "A family of ligands for the TNF receptor superfamily," Stem Cells, 12:440–455, 1994.

Cosulich and Clarke, "Apoptosis: does stress kill?" Curr. Biol., 6:1586–1588, 1996.

Couvreur et al., "Nanocapsules, a New Lysosomotropic Carrier," FEBS Lett., 84:323–326, 1977.

Couvreur, "Polyalkyleyanoacrylates as Colloidal Drug Carriers," Crit. Rev. Ther. Drug Carrier Syst., 5:1–20, 1988.

Crick, Acta Crystallogr. 6:689, 1953.

Cullis et al., "Lipid polymorphism and the functional roles of lipids in biological membranes," Biochem. Biophys. Acta 559:399–420, 1979.

de Jong et al., "Principles of nuclear organization," Cell Biol. Int. Rep. 14:1051–1074, 1990.

Defrance, Billian, Kramner, Lagresle, "Fas-dependent and Fas-independent mechanisms for selection of the mature human B cell repertoire," Ann. N.Y. Acad. Sci., 815:67–74, 1997.

Delmas et al., "Effects of raloxifene on bone mineral density, serum cholesterol concentrations, and uterine endometrium in postmenopausal women," N. Engl. J. Med. 337:1641–1647, 1997.

Delwart and Mosialos, "Retroviral envelope glycoproteins contain a "leucine zipper"-like repeat," AIDS Research and Human Retroviruses 6:703, 1990.

Durie, Fava, Foy, Aruffo, Ledbetter, Noelle, "Prevention of collagen-induced arthritis with an antibody to gp39, the ligand for CD40," Science, 261:1328–1330, 1993.

Earnshaw, "Nuclear changes in apoptosis," Curr. Opin. Cell Biol. 7:337–343, 1995.

Ebeling et al., "Bone turnover markers and bone density across the menopausal transition," J. Clin. Endocrinol. Metab. 81:3366–3371, 1996.

Elkon, and Marshak-Rothstein, "B cells in systemic autoimmune disease: recent insights from Fas-deficient mice and men." Curr. Opin. Immunol., 8:852–859, 1996.

Fadok et al., "Exposure of phosphatidylserine on the surface of apoptotic lymphocytes triggers specific recognition and removal by macrophages," J. Immunol. 148:2207–2216, 1992.

Ferrans, Clark, Zhang, Yu and Herman, "Pathogenesis and prevention of doxorubicin cardiomyopathy," Tsitologiia 39:928–937, 1997.

Fiers et al., "Complete nucleotide sequence of SV40 DNA," Nature, 273:113–120, 1978.

Flores-Romo, Bjorck, Duvert, van Kooten, Saeland and Banchereau, "CD40 ligation on human cord blood CD34+ hematopoietic progenitors induces their proliferation and differentiation into functional dendritic cells," J. Exp. Med. 185:341–349, 1997.

Franke, "Nuclear lamins and cytoplasmic intermediate filament proteins: a growing multigene family," Cell 48:3–15, 1987.

Fuller, Wong, Fox, Choi, Chambers, "TRANCE is necessary and sufficient for osteoblast-mediated activation of bone resorption in osteoclasts," J. Exp. Med., 188:997–1001, 1998.

Funakoshi, Taub, Anver, Raziuddin, Asai, Reddy, Rager, Fanslow, Longo and Murphy, "Immunologic and hematopoietic effects of CD40 stimulation after syngeneic bone marrow transplantation in mice," J. Clin. Invest. 99:484–491, 1997.

Gabizon and Papahadjopoulos, "Liposomes formulations with prolonged circulation time in blood and enhanced uptake by tumors," Proc. Natl. Acad. Sci. USA, 85:6949–6953, 1988.

Garner et al., "Increase in serum parathyroid hormone concentration in the lactating rat: Effects of dietary calcium and lactational intensity," J. Bone Miner. Res. 2:347–352, 1987.

Garnero et al., "Increased bone turnover in late postmenopausal women is a major determinant of osteoporosis," J. Bone Min. Res. 11:337–349, 1996.

Gavrieli et al., "Identification of programmed cell death in situ via specific labeling of nuclear DNA fragmentation," J. Cell Biol. 119:493–501, 1992.

Geddes, "Animal Models of Bone Disease," in Principles of Bone Biology (Bilezikian, Riasz and Rodan, eds.), Academic Press, New York, N.Y., pp. 1343–1354, 1996.

Gefter et al., "A simple method for polyethylene glycol-promoted hybridization of mouse myeloma cells," Somatic Cell Genet. 3:231–236, 1977.

Ghosh-Choudhury et al., "Immortalized murine osteoblasts derived from BMP 2-T-antigen expressing transgenic mice," Endocrinilogy 137:331–339, 1996.

Globus et al., "Skeletal response to dietary calcium in a rat model simulating weightlessness," J. Bone Miner. Res. 1:191–197, 1986.

Goding, "Monoclonal Antibodies: Principles and Practice," pp. 60–74. 2nd Edition, Academic Press, Orlando, Fla., 1986.

Goeddel et al., "Direct expression in Escherichia coli of a DNA sequence coding for human growth hormone," Nature, 281:544–548, 1979.

Goeddel et al., "Synthesis of human fibroblast interferon by E. coli," Nucl. Acids Res., 8:4057–4074, 1980.

Gordon, Katira, Holder, MacDonald and Pound, "Central role of CD40 and its ligand in B lymphocyte responses to T-dependent antigens," Cell. Mol. Biol. (Noisy-le-grand) 40:1–13, 1994.

Guesens et al., "Calcium-deficient diet in ovariectomized dogs limits the effects of 17 beta-estradiol and nandrolone decanoate on bone," J. Bone Miner. Res. 6:791–797, 1991.

Hackett and Dickler, "Immunologic tolerance for immune system-mediated diseases," J. Allergy Clin. Immunol. 103:362–370, 1999.

Hampton et al., "Involvement of extracellular calcium in phosphatidylserine exposure during apoptosis," FEBS Lett. 399:277–282, 1996.

Harlow and Lane, "Antibodies: a Laboratory Manual," Cold Spring Harbor Laboratory, Cold Spring Harbor, N.Y. 1988.

Heath et al., "Rat calvarial cell lines immortalized by SV-40 large T-antigen—Constitutive and retinoic acid-inducible expression of osteoblastic features," Endocrinology 124:3060–3068, 1989.

Henry-Michelland et al., "Attachment of Antibiotics to Nanoparticles; Preparation, Drug-Release and Antimicrobial Activity in vitro," Int. J. Pharm., 35:121–127, 1987.

Hess et al., *J. Adv. Enzyme Reg.*, 7:149, 1968.

Hitzeman et al., "Isolation and characterization of the yeast 3-phosphoglycerokinase gene (PGK) by an immunological screening technique," *J. Biol. Chem.*, 255:12073–12080, 1980.

Ho et al., "Site-Directed Mutagenesis by Overlap Extension Using the Polymerase Chain Reaction," *Gene*, 77:51–59, 1989.

Holland et al., "Isolation and identification of yeast messenger ribonucleic acids coding for enolase, glyceraldehyde-3-phosphate dehydrogenase, and phosphoglycerate kinase," *Biochemistry*, 17:4900–4907, 1978.

Hopp et al., *Bio/Technology* 6:1204, 1988.

Hoppe et al., "A parallel three stranded alpha-helical bundle at the nucleation site of collagen triple-helix formation," *FEBS Lett.* 344:191–195, 1994.

Horiuchi, Amizuka, Takeshita, Takamatsu, Katsuura, Ozawa, Toyama, Bonewald, Kudo, "Identification and characterization of a novel protein, periostin, with restricted expression to periosteum and periodontal ligament and increased expression by transforming growth factor beta [In Process Citation]," *J. Bone Miner Res.*, 14:1239–1249, 1999.

Horowitz and Lorenzo, "Local Regulators of Bone," In Principles of Bone Biology. J. P. Bilezilian, L. G. Raisz, G. A. Rodan, eds. Academic Press, San Diego. 687–691, 1996.

Hosking et al., "Prevention of Bone Loss with Alendronate in Postmenopausal Women under 60 Years of Age," *N. Engl. J. Med* 338:485–492, 1998.

Hu et al., "Sequence requirements for coiled-coils: analysis with lambda repressor-GCN4 leucine zipper fusions," *Science* 250:1400, 1990.

Hu et al., "A novel RING finger protein interacts with the cytoplasmic domain of CD40," *J. Biol. Chem.* 269:30069–30072, 1994.

Hughes et al., "CD44 expression in human bone: A novel marker of osteocytic differentiation," *J. Bone Miner. Res.* 9:39–44, 1994.

Hughes, Dai, Tiffee, Li, Mundy, Boyce, "Estrogen promotes apoptosis of murine osteoclasts mediated by TGF-beta," *Nat. Med.*, 2:1132–1136,1996.

Huse, Sastry, Iverson, Kang, Alting-Mees, Burton, Benkovic and Lemer, Science, "Generation of a large combinatorial library of the immunoglobulin repertoire in phage lambda," 246(4935):1275–1281, 1989.

Ibbotson et al., "Contrasting effects of parathyroid hormone and insulin-like growth factor I in an aged ovariectomized rat model of postmenopausal osteoporosis," *J. Bone Miner. Res.* 7:425–432, 1992.

Illei and Klippel, "Novel approaches in the treatment of lupus nephritis," *Lupus* 7:644–648, 1998.

Inaba, Inaba, Romani, Aya, Deguchi, Ikehara, Muramatsu, Steinman, "Generation of large numbers of dendritic cells from mouse bone marrow cultures supplemented with granulocyte/macrophage colony-stimulating factor," *J. Exp. Med.*, 176:1693–1702, 1992a.

Inaba, Steinman, Pack, Aya, Inaba, Sudo, Wolpe, Schuler, "Identification of proliferating dendritic cell precursors in mouse blood," *J. Exp. Med.*, 175:1157–1167, 1992b.

Inoue, "[The TRAF family protein-mediated B cell proliferation signal and the mechanism of LMP 1-induced B cell transformation]," *Nippon Rinsho.*, 55:299–304, 1997.

Itakura et al., "Expression in *Escherichia coli* of a chemically synthesized gene for the hormone somatostatin," *Science*, 198:1056–1063, 1977.

Jabara, Buckley, Roberts, Lefranc, Loiselet, Khalil and Geha, "Role of JAK3 in CD40-mediated signaling," *Blood* 92:2435–2440, 1998.

Jameson and Wolf, "The antigenic index: a novel algorithm for predicting antigenic determinants," *Compu. Appl. Biosci.*, 4:181–186, 1988.

Jee et al., "Bone structure," In *"The Beagle as an Experimental Animal"* (A. C. Anderson, ed.), pp 162–188, Iowa State University Press, Ames, Iowa, 1970.

Jee et al., "The skeletal adaptation to mechanical usage in the rat," In *"The Aged Rat Model for Bone Biology Studies"* (W. S. S. Jee, ed.), *Cells Mater. pp.*131–141, Scanning Microscopy International, Chicago, Ill., 1991.

Jerome et al., "Effects of ovariectomy on iliac trabecular bone in baboons (*Papio anubis*)," *Calcif. Tissue Int.* 39:206–208, 1986.

Jerome et al., "Bone functional changes in intact, ovariectomized, and ovariectomized, hormone-supplemented adult cynomolgus monkeys (*Macaca fascicularis*) evaluated by serum markers and dynamic histomorphometry," *J. Bone Miner. Res.* 9:527–540, 1994.

Ji, "Bifunctional reagents," *Meth. Enzymol.* 91:580–609, 1983.

Jilka, Weinstein, Bellido, Parfitt, Manolagas, "Osteoblast programmed cell death (apoptosis): Modulation by growth factors and cytokines," *J. Bone Miner. Res.*, 13:793–802, 1998.

Jilka, Weinstein, Bellido, Roberson, Parfitt, Manolagas, "Increased bone formation by prevention of osteoblast apoptosis with PTH," *J. Clin. Invest.*, 104:439–446, 1999.

Jones, "Proteinase mutants of Saccharomyces cerevisiae," Genetics, 85:23–33 1977.

Jones, Dear, Foote, Neuberger and Winter, "Replacing the complementarity-determining regions in a human antibody with those from a mouse," *Nature*, 321(6069):522–525, 1986.

Josien, Wong, Li, Steinman, Choi, "TRANCE, a TNF family member, is differentially expressed on T cell subsets and induces cytokine production in dendritic cells," *J. Immunol.*, 162:2562–2568, 1999.

Kang, Barbas, Janda, Benkovic and Lerner, "Linkage of recognition and replication functions by assembling combinatorial antibody Fab libraries along phage surfaces," *Proc. Natl. Acad. Sci., U.S.A,* 88(10):4363–4366, 1991.

Kato, Windle, Koop, Mundy, Bonewald, "Establishment of an osteocyte-like cell line, MLO-Y4," *J. Bone Miner Res.*, 12:2014–2023, 1997.

Kehry, "CD40-mediated signaling in B cells. Balancing cell survival, growth, and death," *J. Immunol.* 156:2345–2348, 1996.

Kerr et al., "Apoptosis: a basic biological phenomenon with wide-ranging implications in tissue kinetics," *Br. J. Cancer* 26:239–257, 1972.

Kimble, Matayoshi, Vannice, Kung, Williams, Pacifici, "Simultaneous block of interleukin-1 and tumor necrosis factor is required to completely prevent bone loss in the early postovariectomy period," *Endocrinology*, 136:3054–3061, 1995.

Kimmel, "The oophorectomized beagle as an experimental model for estrogen-depletion bone loss in the adult human," In *"The Aged Rat Modelfor Bone Biology Studies"* (W. S. S. Jee, ed.), *Cells Mater.* pp.75–84, Scanning Microscopy International, Chicago, Ill., 1991.

Kingsman et al., "Replication in *Saccharomyces cerevisiae* of plasmid pBR313 carying DNA from the yeast trpl region," *Gene,* 7:141–152, 1979.

Klaus, Choi, Lam, Johnson-Leger and Cliff, "CD40: a pivotal receptor in the determination of life/death decisions in B lymphocytes," *Int. Rev. Immunol.* 15:5–31, 1997.

Kleerekoper and Mendlovic, "Sodium fluoride therapy of postmenopausal osteoporosis," *Endocr. Rev.* 14:312–323, 1993.

Kohler and Milstein, "Continuous cultures of fused cells secreting antibody of predefined specificity," *Nature*, 256:495–497, 1975.

Kohler and Milstein, "Derivation of specific antibody-producing tissue culture and tumor lines by cell fusion," *Eur. J. Immunol.*, 6:511–519, 1976.

Konieczny, Bobrzecka, Laidler and Rybarska, "The combination of IgM subunits and proteolytic IgG fragment by controlled formation of interchain disulphides," *Haematologia*, 14(1):95–99, 1981.

Koopman et al., "Annexin V for flow cytometric detection of phosphatidylserine expression on B cells undergoing apoptosis," *Blood* 84:1415–1420, 1994.

Krystek et al., "Stabilities of leucine zipper dimers estimated by an empirical free energy method," *Int. J. Peptide Res.* 38:229, 1991.

Kuby, "Immunology" 2nd Edition. W. H. Freeman & Company, New York, 1994.

Kyte and Doolittle, "A simple method for displaying the hydropathic character of a protein," *J. Mol. Biol.*, 157:105–132, 1982.

Laman, Claassen, Noelle, "Functions of CD40 and its ligand, gp39 (CD40L)," *Crit. Rev. Immunol.*, 16:59–108, 1996.

Landschulz et al., "The leucine zipper: a hypothetical structure common to a new class of DNA binding proteins," *Science* 240:1759, 1988.

Landschulz et al., "The DNA binding domain of the rat liver nuclear protein C/EBP is bipartite," *Science* 243:1681, 1989.

Laytragoon-Lewin, "Programmed cell death: the influence of CD40, CD95 (Fas or Apo-I) and their ligands," *Med. Oncol.*, 15:15–19, 1998.

Lean et al., "Increased insulin-like growth factor I mRNA expression in rat osteocytes in response to mechanical stimulation," *Am. J. Physiol.* 268:E318–E327, 1995.

Ledbetter et al., "Agonistic and antagonistic properties of CD40 mAb G28-5 are dependent on binding valency," *Circ. Shock* 44:67–72, 1994.

Ledbetter et al., "Agonistic activity of a CD40-specific single-chain Fv constructed from the variable regions of mAb G28-5," *Crit. Rev. Immunol.* 17:427–435, 1997.

Lei, Ohkawara, Stampfli, Mastruzzo, Marr, Snider, Xing and Jordana, "Disruption of antigen-induced inflammatory responses in CD40 ligand knockout mice," *J. Clin. Invest.* 101:1342–1353. 1998.

Lempert et al., "Inflammation-mediated osteopenia (IMO): No change in bone resorption during its development," *Calcif. Tissue Int.* 48:291–292, 1991.

Levy, Espanol-Boren, Thomas, Fischer, Tovo, Bordigoni, Resnick, Fasth, Baer, Gomez, Sanders, Tabone, Plantaz, Etzioni, Monafo, Abinun, Hammarstrom, Abrabamsen, Jones, Finn, Klemola, DeVries, Sanal, Peitsch, Notarangelo, "Clinical spectrum of X-linked hyper-IgM syndrome [see comments]," *J. Pediatr.*, 131:47–54, 1997.

Liossis, Vassilopoulos, Kovacs and Tsokos, "Immune cell biochemical abnormalities in systemic lupus erythematosus," *Clin. Exp. Rheumatol.* 15:677–684, 1997.

Loo et al., "Apoptosis is induced by beta-amyloid in cultured central nervous system neurons," *Proc. Natl. Acad. Sci. USA* 90:7951–7955, 1993.

Loo and Rillema, "Measurement of Cell Death," *Meth. Cell Biol.* 57:251–264, 1998.

Lorenzo, "Local regulators of Bone," In Principles of Bone Biology (Bilezikian, ed.), Academic Press, San Diego, pp. 687–691, 1996.

Love et al., "Effects of tamoxifen on bone mineral density in postmenopausal women with breast cancer," *N. Engl. J. Med.* 326:852–856, 1992.

Lovejoy et al., "Crystal structure of a synthetic triple-stranded alpha-helical bundle," *Science* 259:1288, 1993.

Mach, Schonbeck, Sukhova, Bourcier, Bonnefoy, Pober and Libby, "Functional CD40 ligand is expressed on human vascular endothelial cells, smooth muscle cells, and macrophages: implications for CD40-CD40 ligand signaling in atherosclerosis," *Proc. Natl. Acad. Sci. USA* 94:1931–1936, 1997a.

Mach, Schonbeck, Bonnefoy, Pober and Libby, "Activation of monocyte/macrophage functions related to acute atheroma complication by ligation of CD40: induction of collagenase, stromelysin, and tissue factor," *Circulation* 96:396–399, 1997b.

Mach, Schonbeck, Libby, "CD40 signaling in vascular cells: a key role in atherosclerosis?" *Atherosclerosis*, 137 Suppl:S89–95, 1998a.

Mach, Schonbeck, Sukhova, Atkinson, Libby. "Reduction of atherosclerosis in mice by inhibition of CD40 signalling," *Nature*, 394:200–203, 1998b.

Mach, Schonbeck, Fabunmi, Murphy, Atkinson, Bonnefoy, Graber, Libby, "T lymphocytes induce endothelial cell matrix metalloproteinase expression by a CD40L-dependent mechanism: implications for tubule formation," *Am. J. Pathol.*, 154:229–238, 1999.

Mackey et al., "The ferret as a small model with BMU-based remodeling for skeletal research," *Bone* 17:191S-196S, 1995.

Maloney, Donovan and Hamblin, "Antibody therapy for treatment of multiple myeloma," *Semin. Hematol.* 36:30–33, 1999.

Maloy, et al., "Microbial Genetics" 2nd Edition. Jones and Bartlett Publishers, Boston, Mass., 1994.

Maniatis et al., "Molecular Cloning: a Laboratory Manual," Cold Spring Harbor Laboratory, Cold Spring Harbor, N.Y., 1982.

Mann et al., "A potential primate model for bone loss resulting from medical oophorectomy or menopause," *J. Clin. Endocrinol. Metab.* 71:105–110, 1990.

Marks et al., "Congenitally osteopetrotic (op/op) mice are not cured by transplants of spleen or bone marrow cells from normal littermates," *Metab. Bone Dis. Rel. Res.* 5:183–186, 1984.

Martin et al., "Early redistribution of plasma membrane phosphatidylserine is a general feature of apoptosis regardless of the initiating stimulus: inhibition by overexpression of Bcl-2 and Abl," *J. Exp. Med* 182:1545–1556, 1995.

Matsumoto et al., "Effect of vitamin D metabolites on bone metabolism in a rat model of post-menopausal osteoporosis," *J. Nutr. Sci. Vitaminol.* 31:S61–S65, 1985.

Matsushita et al., "Age related changes in bone mass in the senescence-accelerated mouse (SAM). SAM-R/3 and SAM-P/6 as new murine models for senile osteoporosis," *Am. J. Pathol.* 25:276–283, 1986.

Matsuzaki, Udagawa, Takahashi, Yamaguchi, Yasuda, Shima, Morinaga, Toyama, Yabe, Higashio and Suda, "Osteoclast differentiation factor (ODF) induces osteoclast-like cell formation in human peripheral blood mononuclear cell cultures," *Biochem. Biophys. Res. Commun.* 246:199–204, 1998.

Mayumi, Ohshima, Hata, Kim, Heike, Katamura and Furusho, "IgM-mediated B cell apoptosis," *Crit. Rev. Immunol.* 15:255–269, 1995.

Mayumi, Sumimoto, Kanazashi, Hata, Yamaoka, Higaki, Ishigami, Kim, Heike and Katamura, "Negative signaling in B cells by surface immunoglobulins," *J. Allergy Clin. Immunol.* 98:S238–247, 1996.

McKeon et al., "Homologies in both primary and secondary structure between nuclear envelope and intermediate filament proteins," *Nature* 319:463–468, 1986.

McLachlan and Stewart, "Tropomyosin coiled-coil interactions: evidence for an unstaggered structure," *J. Mol. Biol.* 98:293, 1975.

Miller et al., "Effects of ovariectomy on vertebral trabecular bone in the cynomolgus monkey (*Macaca fascicularis*)," *Calcif. Tissue Int.* 38:62–65, 1986.

Miller et al., "Detection of nuclear matrix proteins in serum from cancer patients," *Cancer Res.* 52:422–427, 1992.

Miller et al., "Death-induced changes to the nuclear matrix: The use of anti-nuclear matrix antibodies to study agents of apoptosis," *Biotechniques* 15:1042–1047, 1993.

Miller et al., *Curr. Comm. Cell Mol. Biol.* 8:357–376, 1994.

Mills, Brooker and Camerini-Otero, "Sequences of human immunoglobulin switch regions: implications for recombination and transcription," *Nucl. Acids Res.,* 18:7305–7316, 1990.

Monreal et al., "Heparin-related osteoporosis in rats. A comparative study between unfractionated heparin and a low molecular-weight heparin," *Haemostasis* 20:204–207, 1990.

Morrison, Johnson, Herzenberg and Oi, "Chimeric human antibody molecules: mouse antigen-binding domains with human constant region domains," *Proc. Natl. Acad. Sci. USA,* 81(21):6851–6855, 1984.

Morrison, Wims, Kobrin and Oi, "Production of novel immunoglobulin molecules by gene transfection," *Mt. Sinai J. Med.,* 53(3):175, 1986.

Mosekilde et al., "Evaluation of the skeletal effects of combined mild dietary restriction and ovariectomy in Sinclair S-1 minipigs: A pilot study," *J. Bone Miner. Res.* 8:1311–1321, 1993.

Moss et al., in *Novel Calcium Binding Proteins, Springer Verlag,* p. 535, 1991.

Nagata, "Apoptosis by death factor," *Cell* 88:355–365, 1997.

Nakagawa, Kinosaki, Yamaguchi, Shima, Yasuda, Yano, Morinaga and Higashio, "RANK is the essential signaling receptor for osteoclast differentiation factor in osteoclastogenesis," *Biochem. Biophys. Res. Commun.* 253:395–400, 1998.

Nakamura et al., "Localization of CD44, the hyaluronidate receptor, on the plasma membrane of osteocytes and osteoblasts in rat tibiae," *Cell Tissue Res.* 280:225–233, 1995.

Namen et al., "Stimulation of B-cell progenitors by cloned murine interleukin-7," *Nature* 333:571, 1988.

Newman et al., "The potential of sheep for the study of osteopenia: Current status and comparison with other animal models," *Bone* 16:277S–284S, 1995.

Ng et al., "Regulation of alkaline phosphatase expression in a neonatal rat calvarial cell strain by retinoic acid," *J. Bone Miner. Res.* 3:53–61, 1988.

Nijweide and Mulder, "Identification of osteocytes in osteoblast-like cultures using a monoclonal antibody specifically directed against osteocytes," *Histochemistly* 84:343–350, 1986.

Nijweide et al., "Osteoblastic differentiation," in *Cell and Molecular Biology of Vertebrate Hard Tissues,* (Evered and Harnett, eds.), Ciba Foundation Symposium 136, pp. 61–77, John Wiley & Sons, Chichester, 1988.

Nijweide, Burger, Nulend and Van der Plas, "The osteocyte," in *Principles of Bone Biology* (Bilezikian, Riasz and Rodan, eds.), Academic Press, New York, N.Y., pp. 115–126, 1996.

Noble, Stevens, Loveridge, Reeve, "Identification of apoptotic changes in osteocytes in normal and pathological human bone," *Bone,* 20:273–282, 1997.

Okumura et al., "26,27-Hexafluoro-1,25-dihydroxyvitamin $D_3$ ($F_6$-1,25(OH)$_2D_3$) prevents osteoporosis induced by immobilization combined with ovariectomy in the rat," *Bone Miner.* 9:101–109, 1987.

Ongphiphadhanakul et al., "Excessive L-thyroxine therapy decreases femoral bone mineral densities in the male rat: Effect of hypogonadism and calcitonin," *J. Bone Miner. Res.* 7:1227–1231, 1992.

O'Shea et al., "Preferential heterodimer formation by isolated leucine zippers from fos and jun," *Science* 245:646, 1989.

O'Shea et al., "X-ray structure of the GCN4 leucine zipper, a two-stranded, parallel coiled coil," *Science* 254:539, 1991.

Osorio and Aguilar-Santelises, "Apoptosis in B-chronic lymphocytic leukaemia," *Med. Oncol.* 15:234–240, 1998.

Ott, "Clinical effects of bisphosphonates in involutional osteoporosis," *J. Bone Min. Res.* 8:S597–S606, 1993.

Pacifici et al., "Coherence therapy does not prevent axial bone loss in osteoporotic women: a preliminary comparative study," *J. Clin. Endocrinol. Metab.* 66:747–753, 1988.

Pacifici, Brown, Puscheck, Friedrich, Slatopolsky, Maggio, McCracken, Avioli, "Effect of surgical menopause and estrogen replacement on cytokine release from human blood mononuclear cells," *Proc. Natl. Acad. Sci. U.S.A.,* 88:5134–5138, 1991.

Parfitt, "The cellular basis of bone turnover and bone loss," *Clin. Orthop. Rel. Res.* 127:236–247, 1977.

Parmley and Smith, "Antibody-selectable filamentous fd phage vectors: affinity purification of target genes," *Gene,* 73(2):305–318, 1988.

Plotkin, Bellido, Bonewald, Papapoulos, Jilka, Manolagas, "Biphosphonates prevent glucocorticoid-induced apoptosis of osteocytes in vitro: a putative mechanism influencing mechanosensing," In American Society of Bone and mineral Research. Vol. 23:5. D. M K, editor. Elsevier, San Francisco. S157, 1998.

Plotkin, Weinstein, Parfitt, Roberson, Manolagass, Bellido, "Prevention of osteocyte and osteoblast apoptosis by bisphosphonates and calcitonin," (Submitted), 1999.

Pope et al., "Effects of age and sex on bone density in the rhesus monkey," *Bone* 10:109–112, 1989.

Prestwood et al., "The short term effects of conjugated estrogen on bone turnover in older women," *J. Clin. Endocrinol. Metab.* 79:366–371, 1994.

Prokop and Bajpai, "Recombinant DNA Technology I" Ann. N.Y. Acad. Sci., Vol. 646, 1991.

Quarles, "Predisone-induced osteopenia in beagles: Variable effects mediated by differential suppression of bone formation," *Am. J. Physiol.* 263:E136–E141, 1992.

Rabindran et al., "Regulation of heat shock factor trimer formation: role of a conserved leucine zipper," *Science* 259:230, 1993.

Raff, "Cell suicide for beginners [news]," *Nature,* 396:119–122, 1998.

Reginster et al., "A double-blind, placebo-controlled, dose-finding trial of intermittent nasal salmon calcitonin for prevention of postmenopausal lumbar spine bone loss," *Am. J. Med.* 98:452–458, 1995.

Richer and Lo, "Introduction of human DNA into mouse eggs by injection of dissected human chromosome fragments", *Science* 245, 175–177, 1989.

Rickard, Russell, Gowen, "Oestradiol inhibits the release of tumour necrosis factor but not interleukin 6 from adult human osteoblasts in vitro," *Osteoporos. Int.,* 2:94–102, 1992.

Riechmann, Clark, Waldmann and Winter, "Reshaping human antibodies for therapy," *Nature,* 332(6162):323–327, 1988.

Rillema, "Measurement of Cell Death," In Methods in Cell Biology: Animal Cell Culture Methods. Vol. 57. J. M. a. D. barnes, editor. Academic press, San Diego. 251–278, 1998.

Rossini et al., "Long-term effects of a treatment course with oral alendronate of postmenopausal osteoporosis," *J. Bone Min. Res.* 9:1833–1837, 1994.

Rubin et al., "Ultrasonic measurement of immobilization-induced osteopenia: An experimental study in sheep," *Calcif. Tissue Int.* 42:30–312, 1988.

Russell et al., "The influence of pyrophosphate, condensed phosphates, phosphonates, and other phosphate compounds on the dissolution of hydroxyapatite in vitro and on bone resorption induced by parathyroid hormone in tissue culture and in thyroparathyroidectomised rats," *Calcif. Tissue Res.* 6:183–196, 1970.

Sambrook, Fritsch and Maniatis, *Molecular Cloning—A Laboratory Manual,* Cold Spring Harbor Laboratory Press, 1989.

Sasaki et al., "Tetracycline administration restores osteoblast structure and function during experimental diabetes," *Anat. Rec.* 231:25–34, 1991.

Schattner and Friedman, "Fas expression and apoptosis in human B cells," *Immunol. Res.* 15:246–257, 1996.

Schulze et al., *Histochem. Cell. Biol.,* 11:61–69, 1999.

Scott, Grdina and Shi, "T cells commit suicide, but B cells are murdered!," *J. Immunol.* 156:2352–2356, 1996.

Segal, "Biochemical Calculations" 2nd Edition. John Wiley and Sons, New York, 1976.

Sempowski, Chess and Phipps, "CD40 is a functional activation antigen and B7-independent T cell costimulatory molecule on normal human lung fibroblasts," *J. Immunol.* 158:4670–4677, 1997.

Sempowski, Rozenblit, Smith and Phipps, "Human orbital fibroblasts are activated through CD40 to induce proinflammatory cytokine production," *Am. J. Physiol.* 274:C707–714, 1998.

Shen et al., "Short-term changes in histomorphometic and biochemical turnover markers and bone mineral density in estrogen- and/or dietary calcium-deficient rats," *Bone* 16:146–156, 1995.

Sideras, Mizuta, Kanamori, Suzuki, Okamoto, Kuze, Ohno, Doi, Fukuhara, Hassan, et al., "Production of sterile transcripts of C gamma genes in an IgM-producing human neoplastic B cell line that switches to IgG-producing cells," *Intl. Immunol.,* 1(6):631–642, 1989.

Siefert and Marks, "Morphological evidence of reduced bone resorption in the osteosclerotic (oc) mouse," *Am. J. Anat.* 172:141–153, 1985.

Simmons and Kunin, "Autoradiographic and biochemical investigations of the effect of cortisone on the bones of the rat," *Clin. Orthop.* 55:201–215, 1967.

Spenser, "Pregnancy and lactational osteoporosis. Animal model: Porcine lactational osteoporosis," *Am. J. Pathol.* 95:277–280, 1979.

Spruce et al, "The first milliseconds of the pore formed by a fusogenic viral envelope protein during membrane fusion," *Proc. Natl. Acad. Sci. U.S.A.* 88:3623, 1991.

Srinivasachar and Neville, "New protein cross-linking reagents that are cleaved by mild acid," *Biochemistry* 28:2501–2509, 1989.

Stauffer et al., "Decreased bone formation, mineralization, and enhanced resorption in calcium-deficient rats," *Am. J. Pathol.* 225:269–276, 1973.

Stein, "Osteoblast Biology," In Osteoporosis. F. D. a. J. K. Markus R, editor. Academic Press, San Diego. 23–33, 1996.

Steinman, Witmer-Pack, Inaba, "Dendritic cells: antigen presentation, accessory function and clinical relevance," *Adv. Exp. Med. Biol.,* 329:1–91993.

Stinchcomb et al., "Isolation and characterisation of a yeast chromosomal replicator," *Nature,* 282:39–43, 1979.

Suda, Udagawa and Takahashi, "Cells of bone: Osteoclast generation," in *Principles of Bone Biology* (Bilezikian, Riasz and Rodan, eds.), Academic Press, New York, N.Y., pp. 87–102, 1996.

Takahashi, Akatsu, Udagawa, Sasaki, Yamaguchi, Moseley, Martin, Suda, "Osteoblastic cells are involved in osteoclast formation," *Endocrinology,* 123:2600–2602, 1988.

Takahashi et al., "Cleavage of lamin A by Mch2 alpha but not CPP32: multiple interleukin 1 beta-converting enzyme-related proteases with distinct substrate recognition properties are active in apoptosis," *Proc. Natl. Acad. Sci. U.S.A.* 93:8395–8400, 1996.

Takeshita, Kikuno, Tezuka, Amann, "Osteoblast-specific factor 2: cloning of a putative bone adhesion protein with homology with the insect protein fasciclin I," *Biochem. J.,* 294:271–278, 1993.

Tewari and Dixit, "Recent advances in tumor necrosis factor and CD40 signaling," *Curr. Opin. Genet. Dev.* 6:39–44, 1996.

Thompson et al., "The bisphosphonate, alendronate, prevents bone loss in ovariectomized baboons," *J. Bone Miner. Res.* 7:951–960, 1992.

Thompson, "Apoptosis. In Fundamental Immunology. W. Paul, editor. Lippincott-Raven, New York, 813–830, 1999.

Tomkinson, Reeve, Shaw, Noble, "The death of osteocytes via apoptosis accompanies estrogen withdrawal in human bone," *J. Clin. Endocrinol. Metab.,* 82:3128–3135, 1997.

Tomkinson, Gevers, Wit, Reeve, Noble, "The role of estrogen in the control of rat osteocyte apoptosis," *J. Bone Miner Res.,* 13:1243–1250, 1998.

Tong and Stone, "CD40 and the effect of anti-CD40-binding on human multiple myeloma clonogenicity," *Leuk. Lymphoma* 21:1–8, 1996.

Trechsel et al., "Hypercalcemia induced with an arotinoid in thyroparathyroidectomised rats: A new model to study bone resorption in vivo," *J. Clin. Invest.* 80:1679–1686, 1987.

Tschumper et al., "Sequence of a yeast DNA fragment containing a chromosomal replicator and the TRP1 gene," *Gene,* 10:157, 1980.

Tsubata, "Regulatory mechanisms for B lymphocyte apoptosis," *Seikagaku* 69:299–310, 1997.

Turner and Bell, "The effects of immobilization on bone histomorphometry in rats," *J. Bone Miner. Res.* 1:300–407, 1986.

Turner and Tjian, "Leucine repeats and an adjacent DNA binding domain mediate the formation of functional cFos-cJun heterodimers," *Science* 243:1689, 1989.

Uhthoff and Jaworski, "Bone loss in response to long-term immobilisation," *J. Bone Joint Surg.* 60:420–429, 1978.

Vailas et al., "Adaptations of young adult rat cortical bone to 14 days of spaceflight," *J. Appl. Physiol.* 73:4S-9S, 1992.

Van der Plas and Nijweide, "Isolation and purification of osteocytes," *J. Bone Miner. Res.* 7:389–396, 1992.

Van der Plas et al., "Characteristics and properties of osteocytes in culture," *J. Bone Miner. Res.* 9:1697–1704, 1994.

van Dijk, Waraar, van Eendenburg, Thienpont, Braakman, Boot, Fleuren and Bolhuis, "Induction of tumor-cell lysis by bi-specific monoclonal antibodies recognizing renal-cell carcinoma and CD3 antigen," *Int. J. Cancer,* 43:344–349, 1989.

van Heeckeren et al., "Role of the conserved leucines in the leucine zipper dimerization motif of yeast GCN4," *Nucl. Acids Res.* 20:3721, 1992.

Vanderschueren et al., "Bone and mineral metabolism in aged male rats: Short and long term effects of androgen deficiency," *Endocrinology* 130:2906–2916, 1993.

Wallach, "Suicide by order: some open questions about the cell-killing activities of the TNF ligand and receptor families," *Cytokine Growth Factor Rev.,* 7:211–221, 1996.

Walsh et al., "Monoclonal antibodies with selective reactivity against osteoblasts and osteocytes in human bone," *J. Bone Miner. Res.* 9:1687–1704, 1994.

Ware, VanArsdale, VanArsdale, "Apoptosis mediated by the TNF-related cytokine and receptor families," *J. Cell Biochem.,* 60:47–55, 1996/

Waters et al., "Effect of tamoxifen citrate on canine immobilization (disuse) osteoporosis," *Vet-Surg.* 20:392–396, 1991.

Weinreb et al., "Immobilization-related bone loss in the rat is increased by calcium deficiency," *Calcif. Tissue Int.* 48:93–100, 1991.

Weinstein, Jilka, Parfitt, Manolagas, "inhibition of osteoblastogenesis and promotion of apoptosis of osteoblasts and osteocytes by glucocorticoids. Potential mechanisms of their deleterious effects on bone," *J. Clin. Invest.,* 102:274–282, 1998.

Weiss et al., "Structural changes in aging bone: Osteopenia in the proximal femurs of female mice," *Bone* 12:165–172, 1991.

Wekerle, Sayegh, Hill, Zhao, Chandraker, Swenson, Zhao and Sykes, "Extrathymic T cell deletion and allogeneic stem cell engraftment induced with costimulatory blockade is followed by central T cell tolerance," *J. Exp. Med.* 187:2037–2044, 1998.

Wiley and Harmsen, "Bone marrow-derived cells are required for the induction of a pulmonary inflammatory response mediated by CD40 ligation," *Am. J. Pathol.* 154:919–926, 1999.

Winter and Milstein, "Man-made antibodies," *Nature,* 349:293–299, 1991.

Wolf et al., "An integrated family of amino acid sequence analysis programs," *Compu. Appl. Biosci.,* 4:187–91, 1988.

Wroblewski and LaDue, "Lactic dehydrogenase activity in blood," *Proc. Soc. Exp. Biol. Med.* 90:210–213, 1955.

Wronski and Morey, "Inhibition of cortical and trabecular bone formation in the long bones of immobilized monkeys," *Clin. Orthop.* 181:269–276, 1983.

Wu et al., "Regional patterns of bone loss and altered bone remodeling in response to calcium deprivation in laboratory rabbits," *Calcif. Tissue Int.* 47:18–23, 1990.

Wyllie, "Glucocorticoid-induced thymocyte apoptosis is associated with endogenous endonuclease activation," *Nature* 284:555–556, 1980.

Yamori et al., "Stroke-prone SHR (SHRSP) as a model for osteoporosis," *Clin. Exp. Hypertension* 13:755-762, 1991.

Yasuda, Shima, Nakagawa, Mochizuki, Yano, Fujise, Sato, Goto, Yamaguchi, Kuriyama, Kanno, Murakami, Tsuda, Morinaga and Higashio, "Identity of osteoclastogenesis inhibitory factor (OCIF) and osteoprotegerin (OPG): a mechanism by which OPG/OCIF inhibits osteoclastogenesis in vitro," *Endocrinology* 139:1329–1337, 1998b.

Yasuda, Shima, Nakagawa, Yamaguchi, Kinosaki, Mochizuki, Tomoyasu, Yano, Goto, Murakami, Tsuda, Morinaga, Higashio, Udagawa, Takahashi and Suda, "Osteoclast differentiation factor is a ligand for osteoprotegerin/osteoclastogenesis-inhibitory factor and is identical to TRANCE/RANKL," *Proc. Natl. Acad. Sci. USA* 95:3597–3602, 1998a.

Yun, Chaudhary, Shu, Frazer, Eqings, Schwartz, Pascual, Hood, Clark, "OPG/FDCR-1, a TNF receptor family member, is expressed in lymphoid cells and is up-regulated by ligating CD40," *J. Immunol i,* 6113–6121, 1998

Zeng et al., "S-ketoprofen inhibits tenotomy-induced bone loss and dynamics in weanling rats," *Bone Miner.* 21:203–208, 1993.

What is claimed is:

1. A method of preventing bone cell death, comprising contacting a bone cell with a biologically effective amount of at least a first composition comprising an oligomeric CD40 ligand that functions as a CD40 agonist.

2. The method of claim 1, wherein said bone cell is an osteoblast.

3. The method of claim 1, wherein said bone cell is an osteocyte.

4. The method of claim 1, wherein said composition comprises an oligomeric CD40 ligand that comprises a CD40 ligand selected from the group consisting of:

(a) a polypeptide comprising amino acids 47–261 of SEQ ID NO:2;

(b) a polypeptide comprising amino acids 50–261 of SEQ ID NO:2; and (c) apolypoptide comprising amino acids 113–261 of SEQ ID NO:2.

5. The method of claim 1, wherein said composition comprises an oligomeric CD40 ligand tat comprises a CD40 ligand polypeptide comprising a leucine zipper polypeptide.

6. The method of claim 1, wherein said bone cell is comprised within an animal and said at least a first composition is administered to said animal.

7. A method of treating or preventing bone loss in an animal having or at risk of developing bone loss, the method comprising administering to said animal a therapeutically effective amount of at least a first composition comprising an oligomeric CD40 ligand that functions as a CD40 agonist.

8. The method of claim 7, wherein said composition comprises an oligomeric CD40 ligand that comprises a CD40 ligand polypeptide selected from the group consisting of:

(a) a polypeptide comprising amino acids 47–261 of SEQ ID NO:2;

(b) a polypeptide comprising amino acids 50–261 of SEQ ID NO:2; and (a) a polypeptide comprising amino acids 113–261 of SEQ ID NO:2.

9. The method of claim 7, wherein said composition comprises an oligomeric CD40 ligand that comprises a CD40 ligand polypeptide comprising a leucine zipper polypeptide.

10. The method of claim 9, wherein said leucine zipper polypeptide comprises the amino acid sequence of SEQ ID NO:3.

11. The method of claim 7, wherein said composition comprises an oligomeric CD40 ligand that comprises CD40 ligand polypeptides operatively attached via a peptide linker sequence.

12. The method of claim 7, wherein said composition comprises an oligomeric CD40 ligand that comprises CD40 ligand polypeptides linked via a biochemical cross-linker.

13. The method of claim 7, wherein said composition comprises a trimeric CD40 ligand.

14. The method of claim 7, wherein said composition further comprises at least a first cytokine.

15. The method of claim 14, wherein said composition further comprises the cytokine IL-4 or IL-6.

16. The method of claim 7, wherein said composition further comprises at least a second, distinct agent used to prevent bone cell death or treat bone loss.

17. The method of claim 7, wherein said animal has or is at risk of developing osteoporosis, osteonecrosis or inflammatory arthritis, or wherein said animal is being treated or is scheduled for treatment with a steroidal therapeutic.

18. The method of claim 7, wherein said animal is a human subject.

19. A method of reducing bone loss in patient afflicted with a disease or condition associated with bone loss, the method comprising administering to said patient a therapeutically effective amount of at least a first composition comprising an oligomeric CD40 ligand that functions as a CD40 agonist.

20. The method of claim 19, wherein said patient is afflicted with osteoporosis or osteonecrosis.

21. The method of claim 19, wherein said patient is afflicted with inflammatory arthritis.

22. The method of claim 19, wherein said patient exhibits bone loss associated with the administration of at least a first steroid to said patient.

23. The method of claim 22, wherein said at least a first steroid is administered to said patient to treat postmenopausal estrogen loss, estrogen loss due to ovariectomy or total hysterectomy, lupus nephritis, Takayasu's arteritis, Wegeners granulomatosis, anti-glomerular basement membrane nephritis, myositis, scleroderma, idiopathic autoimmune thrombocytopenia, asthmna, a chronic obstructive lung disease, nephrotic/nephritic syndrome or cancer.

24. The method of claim 22, wherein said at least a first steroid is administered in conjunction with an organ transplant or a bone marrow transplant.

25. The method of claim 19, further comprising simultaneously or sequentially administering to said patient at least a second, distinct anti-bone loss agent.

26. The method of claim 25, wherein said second anti-bone loss agent is selected from the group consisting of an anti-apoptosis agent, estrogen, a bisphosphonate, a selective estogen receptor modulator, alendronate, calcitonin, calcium, fluoride and vitamin D.

27. A method of treating a patient afflicted with a disease characterized by bone cell death, bone cell apoptosis or bone loss, comprising administering to said patient a therapeutically effective amount of composition comprising an oligomeric CD40 ligand polypeptide that functions as a CD40 agonist.

28. The method of claim 27, wherein said composition comprises an oligomeric CD40 ligand that comprises a CD40 ligand polypeptide comprising amino acids 47–261 of SEQ ID NO:2, amino acids 50–261 of SEQ ID NO:2 or amino acids 113–261 of SEQ ID NO:2.

29. A method of preventing bone cell death in a patient afflicted with a disease associated with bone death, the method of comprising administering to said patient a combined therapeutically effective amount of at least a first composition comprising an oligomeric CD40 ligand that functions as a CD40 agonist, and at least a second, distinct therapeutic agent used to treat or prevent bone cell death.

30. The method of claim 29, wherein a single composition comprising said oligomeric CD40 ligand and said at least a second, distinct therapeutic agent is administered to said patient.

31. A method of treating or preventing osteoporosis in a patient having or at risk of developing osteoporosis, comprising administering to said patient a therapeutically effective amount of at least a first composition comprising an oligomeric CD40 ligand that functions as a CD40 agonist.

32. The method of claim 31, further comprising administering to said patient at least a second, distinct anti-osteoporosis agent.

33. A method of steroid therapy, comprising administering to a patient in need of steroid therapy a therapeutically effective amount of a composition comprising an oligomeric CD40 ligand that functions as a CD40 agonist.

34. A method of reducing the osteodetrimental side effects of steroid therapy, comprising administering to a patient undergoing steroid therapy a composition comprising an oligometic CD40 ligand that functions as a CD40 agonist in an amount effective to reduce the osteodetrimental side effects of said steroid therapy.

* * * * *

UNITED STATES PATENT AND TRADEMARK OFFICE
CERTIFICATE OF CORRECTION

PATENT NO.    : 6,482,411 B1
DATED         : November 19, 2002
INVENTOR(S)   : Seema S. Ahuja and Lynda F. Bonewald It is certified that error appears in the above-identified patent and that said Letters Patent is hereby corrected as shown below:

<u>Title page,</u>
Item [*], delete "71 days" and insert -- 135 days -- therefor.
Item [75], Inventor, delete "Seema A. Ahuja" and insert -- Seema S. Ahuja -- therefor.

<u>Column 93,</u>
Line 1, delete "apolypoptide" and insert -- a polypeptide -- therefor.
Line 4, delete "tat" and insert -- that -- therefor.

Signed and Sealed this

Thirteenth Day of May, 2003

JAMES E. ROGAN
*Director of the United States Patent and Trademark Office*